(12) United States Patent
Faustman

(10) Patent No.: US 8,697,077 B2
(45) Date of Patent: *Apr. 15, 2014

(54) METHODS AND COMPOSITIONS FOR TREATING AUTOIMMUNE DISEASES

(75) Inventor: Denise L. Faustman, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/462,160

(22) Filed: May 2, 2012

(65) Prior Publication Data

US 2012/0213731 A1 Aug. 23, 2012

Related U.S. Application Data

(60) Continuation of application No. 12/632,452, filed on Dec. 7, 2009, now Pat. No. 8,173,129, which is a division of application No. 10/358,664, filed on Feb. 5, 2003, now Pat. No. 7,628,988.

(60) Provisional application No. 60/392,687, filed on Jun. 27, 2002.

(51) Int. Cl.
| | |
|---|---|
| *A61K 35/26* | (2006.01) |
| *A61K 35/28* | (2006.01) |
| *A61K 39/40* | (2006.01) |
| *A61K 39/395* | (2006.01) |

(52) U.S. Cl.
USPC .................. 424/139.1; 424/142.1; 424/154.1; 424/577

(58) Field of Classification Search
None
See application file for complete search history.

(56) References Cited

U.S. PATENT DOCUMENTS

| | | | |
|---|---|---|---|
| 4,309,418 A | 1/1982 | Green | |
| 4,457,916 A | 7/1984 | Hayashi et al. | |
| 4,495,282 A | 1/1985 | Ohnishi et al. | |
| 4,677,063 A | 6/1987 | Mark et al. | |
| 4,677,064 A | 6/1987 | Mark et al. | |
| 4,681,760 A | 7/1987 | Fathman | |
| 4,791,101 A | 12/1988 | Adolf | |
| 4,816,567 A | 3/1989 | Cabilly et al. | |
| 4,879,226 A | 11/1989 | Wallace et al. | |
| 4,963,354 A | 10/1990 | Shepard et al. | |
| 4,985,241 A | 1/1991 | Zimmerman et al. | |
| 5,002,876 A | 3/1991 | Sreekrishna et al. | |
| 5,059,530 A | 10/1991 | Oshima et al. | |
| 5,139,481 A | 8/1992 | Faustman et al. | |
| 5,215,743 A | 6/1993 | Singh et al. | |
| 5,283,058 A | 2/1994 | Faustman | |
| 5,288,852 A | 2/1994 | Yamada et al. | |
| 5,370,870 A | 12/1994 | Wong | |
| 5,487,984 A | 1/1996 | Allet et al. | |
| 5,538,854 A | 7/1996 | Faustman | |
| 5,560,908 A | 10/1996 | Satoh et al. | |
| 5,593,698 A | 1/1997 | Weiner et al. | |
| 5,783,216 A | 7/1998 | Faustman | |
| 5,821,337 A | 10/1998 | Carter et al. | |
| 5,843,425 A | 12/1998 | Sachs et al. | |
| 5,843,452 A | 12/1998 | Wiedmann et al. | |
| 5,874,306 A | 2/1999 | Beattie et al. | |
| 5,919,452 A | 7/1999 | Le et al. | |
| 6,046,031 A | 4/2000 | Ni et al. | |
| 6,056,952 A | 5/2000 | Rosenberg | |
| 6,159,461 A | 12/2000 | Besmer et al. | |
| 6,165,737 A | 12/2000 | Wang et al. | |
| 6,284,879 B1 | 9/2001 | Faustman | |
| 6,414,218 B1 | 7/2002 | Faustman et al. | |
| 6,420,139 B1 | 7/2002 | Classen | |
| 6,491,908 B1 | 12/2002 | Rosenberg | |
| 6,599,710 B1 | 7/2003 | Faustman | |
| 6,617,171 B2 | 9/2003 | Faustman et al. | |
| 6,660,487 B2 | 12/2003 | Faustman | |
| 6,773,705 B1 | 8/2004 | Faustman et al. | |
| 6,844,011 B1 | 1/2005 | Faustman | |
| 6,866,843 B2 | 3/2005 | Habener et al. | |
| 6,923,959 B2 | 8/2005 | Habener et al. | |
| 6,984,380 B1 | 1/2006 | Faustman | |
| 7,015,037 B1 | 3/2006 | Furcht et al. | |
| 7,438,902 B2 | 10/2008 | Habener et al. | |
| 7,485,293 B1 | 2/2009 | Faustman | |
| 7,510,877 B2 | 3/2009 | Yilmaz et al. | |
| 7,537,756 B2 | 5/2009 | Habener et al. | |
| 7,582,313 B2 | 9/2009 | Faustman | |
| 7,628,988 B2 * | 12/2009 | Faustman ................... | 424/139.1 |
| 8,173,129 B2 * | 5/2012 | Faustman ................... | 424/139.1 |

(Continued)

FOREIGN PATENT DOCUMENTS

| | | |
|---|---|---|
| WO | WO-92/04033 A1 | 3/1992 |
| WO | WO-95/24914 A1 | 9/1995 |

(Continued)

OTHER PUBLICATIONS

Kaufman et al., J of Immunol. 1997, V.158, pp. 2435-2442.*

(Continued)

*Primary Examiner* — Michail Belyavskyi
(74) *Attorney, Agent, or Firm* — Clark & Elbing LLP; Todd Armstrong

(57) ABSTRACT

The invention features methods for increasing or maintaining the number of functional cells of a predetermined type, for example, insulin producing cells of the pancreas, blood cells, spleen cells, brain cells, heart cells, vascular tissue cells, cells of the bile duct, or skin cells, in a mammal (e.g., a human patient) that has injured or damaged cells of the predetermined type.

22 Claims, 28 Drawing Sheets

(56) References Cited

U.S. PATENT DOCUMENTS

| | | |
|---|---|---|
| 2002/0106689 A1 | 8/2002 | Faustman et al. |
| 2002/0123472 A1 | 9/2002 | Faustman |
| 2002/0187548 A1 | 12/2002 | Keller et al. |
| 2003/0005469 A1 | 1/2003 | Faustman et al. |
| 2003/0031657 A1 | 2/2003 | Habener et al. |
| 2004/0028658 A1 | 2/2004 | Faustman |
| 2004/0031066 A9 | 2/2004 | Faustman et al. |
| 2004/0229785 A1 | 11/2004 | Faustman |
| 2005/0158288 A1 | 7/2005 | Faustman |
| 2005/0158302 A1 | 7/2005 | Faustman et al. |
| 2005/0244386 A1 | 11/2005 | Habener et al. |
| 2006/0062769 A1 | 3/2006 | Habener et al. |
| 2007/0116688 A1 | 5/2007 | Faustman |
| 2008/0102054 A1 | 5/2008 | Faustman |
| 2010/0068177 A1 | 3/2010 | Faustman |

FOREIGN PATENT DOCUMENTS

| | | |
|---|---|---|
| WO | WO-95/25533 A1 | 9/1995 |
| WO | WO-97/08328 A1 | 3/1997 |
| WO | WO-97/21802 A1 | 6/1997 |
| WO | WO-00/53209 A1 | 9/2000 |
| WO | WO-02/26819 A2 | 4/2002 |
| WO | WO-2004/003164 A2 | 1/2004 |

OTHER PUBLICATIONS

Feldman et al., Transplant. Proc. 1998, 30, 4126-4127.*
Mestas et al J. of Immunology, 2004, 172, pp. 2731-238.*
Corbett et al. (Proc Natl Acad Sci U S A. Mar. 1, 1993 ;90(5): 1731-5.*
Couzin Science, 2006, V.311, p. 1694.*
Fischer et al., "A TNF receptor 2 selective agonist rescues human neurons from oxidative stress-induced cell death," PloS One. 6(11):e27621(1-11) (2011).
Loetscher et al., "Human tumor necrosis factor α (TNF α) mutants with exclusive specificity for the 55-kDa or 75-kDa TNF receptors," J Biol Chem. 268(35):26350-26357 (1993).
Van Zee et al., "A human tumor necrosis factor (TNF) alpha mutant that binds exclusively to the p55 TNF receptor produces toxicity in the baboon," J Exp Med. 179(4):1185-1191 (1994).
Welborn et al., "A human tumor necrosis factor p75 receptor agonist stimulates in vitro T cell proliferation but does not produce inflammation or shock in the baboon," J Exp Med. 184(1):165-171 (1996).
Creasey et al., "Biological effects of recombinant human tumor necrosis factor and its novel muteins on tumor and normal cell lines," Cancer Res. 47(1):145-9 (1987).
Tavernier et al., "Analysis of the structure-function relationship of tumour necrosis factor. Human/mouse chimeric TNF proteins: general properties and epitope analysis," J Mol Biol. 21 1(2):493-501 (1990).
Al-Awquati et al., "Stem cells in the kidney," Kidney Int. 61:387-395 (2002).
Aldrich et al., "Positive selection of self- and alloreactive CD8+ T cells in *Tap-1* mutant mice," Proc Natl Acad Sci USA. 91:6525-6528 (1994).
Alison et al., "Hepatocytes from non-hepatic adult stem cells," Nature. 406:257 (2000).
Allen et al., "Effect of *Bacillus* calmette-guerin vaccination on new-onset Type 1 Diabetes," Diabetes Care. 22(1):1703-1707 (1999).
Altomonte et al., "Serum levels of interleukin-1b, tumour necrosis factor-a and interleukin-2 in rheumatoid arthritis. Correlation with disease activity," Clin Rheumatol. 11(2):202-205 (1992).
Anderson et al., "The NOD mouse: A model of immune dysregulation," Annu Rev Immunol. 23:447-485 (2005).
Anderson et al., "Can stem cells cross lineage boundaries?," Nat Med. 7:393-395 (2001).
Anderson et al., "Studies on the cytophilic properties of human β2 microglobulin," J Immunol. 114:997-1000 (1975).
Aristarkhov et al., " E2-C, a cyclin-selective ubiquitin carrier protein required for the destruction of mitotic cyclins," Proc Natl Acad Sci USA. 93:4294-4299 (1996).
Aranda et al., "Analysis of intestinal lymphocytes in mouse colitis mediated by transfer of CD4+, CD45RBhigh T Cells to SCID recipients," J Immunol. 158(7):3464-3473 (1997).
Ashton-Rickardt et al., "Peptide contributes to the specificity of positive selection of CD8+ T Cells in the thymus," Cell. 73:1041-1049 (1993).
Ashton-Rickardt et al., "Evidence for a differential avidity model of T Cell selection in the thymus," Cell . 76:651-663 (1994).
Atkinson et al., "The NOD mouse model of Type 1 Diabetes: As good as it gets?," Nat Med. 5(6):601-604 (1999).
Baeuerle et al, "NF-kB: Ten years after," Cell. 87:13-20 (1996).
Baeza et al., "Pancreatic regenerating gene overexpression in the nonobese diabetic mouse during active diabetogensis," Diabetes. 45(1):67-70 (1996).
Baeza et al., "Reg protein: a potential beta-cell-specific growth factor?," Diabetes Metab. 22:229-234 (1996).
Baeza et al., "Specific reg II gene overexpression in the non-obese diabetic mouse pancreas during active diabetogenesis," FEBS Letters. 416:364-368 (1997).
Baik et al., "BCG vaccine prevents insulitis in low dose streptozotocin-induced diabetic mice," Diabetes Res. and Clin. Pract. 46: 91-97, 1999.
Baldwin, "The $NF_{-k}B$ and $I_kB$ proteins: new discoveries and insights," Ann. Rev. Immunol. 14:649-683 (1996).
Ban et al., "Selective death of autoreactive T Cells in human diabetes by TNF or TNF receptor 2 agonism," Proc. Natl. Acad. Sci. USA 105: 13644-13649, 2008.
Barres, "A new role for glia: generation of neurons!," Cell 97: 667-670, 1999.
Baxter et al., "Mycobacteria precipitate an SLE-like syndrome in diabetes-prone NOD mice," Immunology. 83:227-231 (1994).
Beg et al., "An essential role for NF-KB in preventing TNF-α-induced cell death," Science. 274:782-784 (1996).
Bernabeu et al., "β2 -microglobulin from serum associates with MHC class I antigens on the surface of cultured cells," Nature. 308:642-645 (1984).
Bendelac et al., "Syngeneic transfer of autoimmune diabetes from diabetic NOD mice to healthy neonates," J. Exp. Med. 166:823-832 (1987).
Bill et al, "Use of soluble MHC class II/peptide multimers to detect antigen-specific T cells in human disease," Arthritis Res. 4:261-265 (2002).
Bjornson et al., "Turning brain into blood: A hematopoietic fate adopted by adult neural stem cells in vitro," Science. 283:534-537 (1999).
Boches et al, "Role for the adenosine triphosphate-dependent proteolytic pathway in reticulocyte maturation," Science. 215:978-980 (1982).
Brás et al., "Diabetes-prone NOD mice are resistant to *Mycobacterium avium* and the infection prevents autoimmune disease," Immunology. 89:20-25 (1996).
Brayer et al., "Alleles from chromosomes 1 and 3 of NOD mice combine to influence Sjögren's syndrome-like autoimmune exocrinopathy, " J. Rheumatol. 27(8):1896-1904 (2000).
Brazelton et al., "From marrow to brain: expression of neuronal phenotypes in adult mice," Science. 290:1775-1779 (2000).
Brod et al., "Ingested interferon α suppresses Type I diabetes in non-obese diabetic mice," Diabetologia. 41:1227-1232 (1998).
Brodbeck et al., "Genetic determination of nephrogenesis: the pax/eya/six gene network," Pediatr. Nephrol. 19:249-255 (2004). (Abstract Only).
Bunting et al., "Enforced P-glycoprotein pump function in murine bone marrow cells results in expansion of side population stem cells in vitro and repopulating cells in vivo," Blood. 96(3):902-909 (2000).
Cavallo et al., "BCG vaccine with and without nicotinamide in recent onset IDDM: a multicenter randomized trial," Autoimmunity 24(Suppl.1):A063 (1996).

(56) References Cited

OTHER PUBLICATIONS

Caetano et al., "Effect of methotrexate (MTX) on NAD(P)+ dehydrogenases of HeLa cells: malic enzyme, 2- oxoglutarate and isocitrate dehydrogenases," Cell Biochem Funct. 15(4):259-264 (1997).
Chatenoud et al., "CD3 antibody-induced dominant self tolerance in overtly diabetic NOD mice," J Immunol. 158(6):2947-2954 (1997).
Choi et al., "Prevention of Encephalomyocarditis virus-induced diabetes by live recombinant *Mycobacterium bovis Bacillus* Calmette-Guérin in susceptible mice," Diabetes. 49:1459-1467 (2000).
Cole et al., "Two ParaHox genes, SpLox and SpCdx, interact to partition the posterior endoderm in the formation of a functional gut," Development. 136:541-549 (2009).
Colucci et al., "Programmed cell death in the pathogenesis of murine IDDM: resistance to apoptosis induced in lymphocytes by cyclophosphamide," J Autoimmunity 9:271-276 (1996).
Corbett et al., "Nitric oxide mediates cytokine-induced inhibition of insulin secretion by human islets of langerhans" Proc Natl Acad Sci USA. 90(5):1731-1735 (1993).
Coux et al., "Enzymes catalyzing ubiquitination and proteolytic processing of the p105 precursor of nuclear factor $_\kappa$B1," J Biol Chem. 273(15):8820-8828 (1998).
Couzin, "Diabetes studies conflict on power of spleen cells," Science. 311:1694 (2006).
Darzynkiewicz et al., "Use of flow and laser scanning cytometry to study mechanisms regulating cell cycle and controlling cell death," Clinics in Laboratory Medicine. 21:857-873 (2001).
Dear et al., "The Hox11 gene is essential for cell survival during spleen development," Development. 121:2909-2915 (1995).
Declaration of Dr. Denise Faustman from U.S. Appl. No. 10/358,644, filed on May 15, 2009.
Dieguez-Acuna et al., "Characterization of mouse spleen cells by subtractive proteomics," Mol Cell Proteomics. 4(10):1459-1470 (2005).
Dieguez-Acuña et al., "Proteomics identifies multipotent and low oncogenic risk stem cells of the spleen," Int J Biochem Cell Biol. 42:1651-1660 (2009).
Dilts et al., "Autoimmune diabetes: The involvement of benign and malignant autoimmunity," J Autoimmun. 12:229-232 (1999).
Dinarello, "Interleukin-1, Interleukin-1 receptors and Interleukin-1 receptor antagonist," Intern Rev Immunol. 16:457-499 (1998).
Driscoll et al., "The proteasome (multicatalytic protease) is a component of the 1500-kDa proteolytic complex which degrades ubiquitin-conjugated proteins," J Biol Chem. 265:4789-4792 (1990).
Durand et al., "Mesenchymal lineage potentials of Aorta-Gonad-Mesonephros stromal clones," Heamatologica. 91:1172-1179 (2006).
Eglitis et al., "Hematopoietic cells differentiate into both microglia and macroglia in the brains of adult mice," Proc Natl Acad Sci USA. 94:4080-4085 (1997).
Elliott et al., "Effect of Bacille Calmette-Guérin vaccination on C-Peptide secretion in children newly diagnosed with IDDM," Diabetes Care. 21(10):1691-1693 (1998).
Eytan et al., "ATP-dependent incorporation of 20S protease into the 26S complex that degrades proteins conjugated to ubiquitin," Proc Natl Acad Sci USA. 86:7751-7755 (1989).
Fan et al., "Generation of p50 subunit of NF-KB by processing of p105 through an ATP-dependent pathway," Nature. 354:395-398 (1991).
Faustman et al., "Abnormal T-lymphocyte subsets in Type I Diabetes," Diabetes. 38:1462- 1468 (1989).
Faustman et al., "Linkage of faulty major histocompatibility complex class I to autoimmune diabetes," Science. 254:1756-1761 (1991).
Faustman et al., "Murine pancreatic β-Cells express H-2K and H-2D but not Ia Antigens," J Exp Med. 151:1563-1568 (1980).
Faustman et al., "Prevention of xenograft rejection by masking donor HLA class I antigens," Science. 252:1700-1702 (1991).
Faustman et al., "T-lymphocyte changes linked to autoantibodies. Association of insulin autoantibodies with CD4+CD45R+ lymphocyte subpopulation in prediabetic subjects," Diabetes. 40:590-597 (1991).
Feldman et al., "Anti-TNFα therapy is useful in rheumatoid arthritis and Crohn's disease: Analysis of the mechanism of action predicts utility in other diseases," Transplant Proc. 30(8):4126-4127 (1998).
Ferrando et al., "Adult T-Cell ALL patients whose lymphoblasts express the HOX11 oncogene have an excellent prognosis when treated with chemotherapy and are not candidates for allogeneic bone marrow transplantation in first remission," Blood. 11:154A (2002).
Fischer et al., "An improved flow cytometric assay for the determination of cytotoxic T lymphocyte activity," J Immunol Methods. 259:159-169 (2002).
Foulis, "C.L. Oakley lecture (1987). The pathogenesis of beta cell destruction in Type I (insulin-dependent) diabetes mellitus," J Pathol. 152(3):141-148 (1987).
Fu et al., "Antigen processing and autoimmunity: Evaluation of mRNA abundance and function of HLA-Linked genes," Ann NY Acad Sci. 842:138-155 (1998).
Fu et al., "Defective major histocompatibility complex class I expression on lymphoid cells in autoimmunity," J Clin Invest. 91:2301-2307 (1993).
Fukada et al., "Two signals are necessary for cell proliferation induced by a cytokine receptor gp130: Involvement of STAT3 in anti-apoptosis," Immunity. 5:449-460 (1996).
Gage, "Mammalian neural stem cells," Science. 287:1433-1438 (2000).
Gage et al., "Multipotent progenitor cells in the adult dentate gyrus," J Neurobiol. 36:249-266 (1998).
Ganoth et al., "A multicomponent system that degrades proteins conjugated to ubiquitin. Resolution of factors and evidence for ATP-dependent complex formation," J Biol Chem. 263(25):12412-12419 (1988).
Gaur et al., "Induction of islet allotolerance in nonhuman primates," Ann NY Acad Sci. 958:199-203 (2002).
Gazda et al., "Diabetes results from a late change in the autoimmune response of NOD mice," J Autoimmun. 10:261-270 (1997).
Gazda et al., "Regulation of autoimmune diabetes: characteristics of non-islet-antigen specific therapies," Immunol Cell Biol. 74: 401-407 (1996).
Genestier et al., "Immunosuppressive properties of methotrexate: Apoptosis and clonal deletion of activated peripheral T Cells," J Clin Invest. 102(2):322-328 (1998).
Gerich et al., "Advances in diabetes for the millenium: Understanding insulin resistance," MedGenMed. 6(Suppl): 11:1-9 (2004).
Ghosh et al., "Activation in vitro of NF-$_\kappa$B by phosphorylation of its inhibitor I$_\kappa$B," Nature. 344:678-682 (1990).
Glas et al., "The CD8+ T Cell repertoire in β2-microglobulin-deficient mice is biased towards reactivity against self-major histocompatibility class I," J Exp Med. 179(2):661-672 (1994).
Goldberg, "Functions of the proteasome: The lysis at the end of the tunnel," Science. 268:522-523 (1995).
Goldberg, "The mechanism and functions of ATP-dependent proteases in bacterial and animal cells," Eur J Biochem. 203:9-23 (1992).
Gottlieb et al., "Cell acidification in apoptosis: Granulocyte colony-stimulating factor delays programmed cell death in neutrophils by up-regulating the vacuolar H$^+$-ATPase," Proc Natl Acad Sci USA. 92:5965-5968 (1995).
Graves et al., "Lack of association between early childhood immunizations and β-Cell autoimmunity," Diabetes Care 22:1694-1967 (1999).
Grewal et al., "Local expression of transgene encoded TNFα in islets prevents autoimmune diabetes in nonobese diabetic (NOD) mice by preventing the development of auto-reactive islet-specific T Cells," J Exp Med. 184:1963-1974 (1996).
Grilli et al., "Neuroprotection by aspirin and sodium salicylate through blockade of NF-kB activation," Science. 274:1383-1385 (1996).
Gronostajski et al., "The ATP dependence of the degradation of short- and long-lived proteins in growing fibroblasts," J Biol Chem. 260(6):3344-3349 (1985).

(56) References Cited

OTHER PUBLICATIONS

Gueckel et al., "Mutations in the yeast proteasome B-Type subunit Pre3 uncover position-dependent effects on proteasomal peptidase activity and in vivo function," J Biol Chem. 273(31): 19443-19452 (1998).

Gupta, "Molecular steps of tumor necrosis factor receptor-mediated apoptosis," Curr Mol Med. 1(3):317-324 (2001).

Haas et al., "Pathways of ubiquitin conjugation," FASEB J. 11:1257-1268 (1997).

Hao et al., "Effect of mycophenolate mofetil on islet allografting to chemically induced or spontaneously diabetic animals," Transplant Proc. 24(6): 2843-2844 (1992).

Harada et al., "Prevention of overt diabetes and insulitis in NOD mice by a single BCG vaccination," Diabetes Res Clin Pract. 8:85-89 (1990).

Hartwell et al., "Aberrant cytokine regulation in macrophages from young autoimmune-prone mice: Evidence that the intrinsic defect in MRL macrophage IL-1 expression is transcriptionally controlled," Mol Immunol. 32(10):743-751 (1995).

Hayashi et al., "Essential role of human leukocyte antigen-encoded proteasome subunits in NF-kB activation and prevention of tumor necrosis Factor-α-induced apoptosis," J Biol Chem. 275(7):5238-5247 (2000).

Hayashi et al., "NOD mice are defective in proteasome production and activation of NF-KB," Mol Cell Biol. 19(12):8646-8659 (1999).

Hershko et al., "The ubiquitin system for protein degradation," Annu Rev Biochem. 61: 761-807 (1992).

Hostikka et al., "The mouse hoxc11 gene: genomic structure and expression pattern," Mech Dev. 70:133-145 (1998). (Abstract Only).

Hester et al., "Studies on the cytophilic properties of human β2-microglobulin. II. The role of histocompatibility antigens," Scand J Immunol. 9(2):125-134 (1979).

Horsfall et al., "Characterization and specificity of B-cell responses in lupus induced by Mycobacterium bovis in NOD/Lt mice," Immunology 95:8-17 (1998).

Horwitz et al., "Recombinant baccillus calmette-guérin (BCG) vaccines expressing the Mycobacterium Tuberculosis 30-kDa major secretory protein induce greater protective immunity against Tuberculosis than conventional BCG vaccines in a highly susceptible animal model," Proc Natl Acad Sci USA. 97:13853-13858 (2000).

Hsu et al., "TRADD-TRAF2 and TRADD-FADD interactions define two distinct TNF receptor 1 signal transduction pathways," Cell. 84:299-308 (1996).

Humphreys-Behr et al., "New concepts for the development of autoimmune exocrinopathy derived from studies with the NOD mouse model," Arch Oral Biol. 44:S21-S25 (1999). (Abstract Only).

Hyafil et al., "Dissociation and exchange of the $\beta_2$-micoglobulin subunit of HLA-A and HLA-B antigens," Proc Natl Acad Sci USA. 76(11):5834-5838 (1979).

Hymowitz et al., "Toward small-molecule agonists of TNF receptors," Nat Chem Biol. 1(7):353-354 (2005).

Jackson et al., "Hematopoietic potential of stem cells isolated from murine skeletal muscle," Proc Natl Acad Sci USA. 96(25):14482-14486 (1999).

Jacob et al., "Monoclonal anti-tumor necrosis factor antibody renders non-obese diabetic mice hypersensitive to irradiation and enhances insulitis development," Int Immunol. 4(5):611-614 (1992).

Jacob et al., "Prevention of diabetes in nonobese diabetic mice by tumor necrosis factor (TNF): Similarities between TNF-α and interleukin 1," Proc Natl Acad Sci USA. 87:968-972 (1990).

Jacob et al., "Tumour necrosis factor-α in murine autoimmune 'lupus' nephritis," Nature. 331:356-358 (1988).

Jakubowski et al., "Phase I trial of intramuscularly administered tumor necrosis factor in patients with advanced cancer," J Clin Oncol. 7(3):298-303 (1989).

Jiang et al., "Pluripotency of mesenchymal stem cells derived from adult marrow," Nature. 418:41-49 (2002).

Johansson et al' "Identification of a neural stem cell in the adult mammalian central nervous system," Cell. 96:25-34 (1999).

Juang et al., "Beneficial influence of glycemic control upon the growth and function of transplanted islets," Diabetes 43:1334-1339 (1994).

Kaijzel et al., "Functional analysis of a human tumor necrosis factor α (TNF-α) promoter polymorphism related to joint damage in rheumatoid arthritis," Mol Med. 4:724-733 (1998).

Kanzler et al, "Hox11 acts cell autonomously in spleen development and its absence results in altered cell fate of mesenchymal spleen precursors," Devel Biol. 234:231-243 (2001).

Kaufman et al., "Patterns of hemopoietic reconstitution in nonobese diabetic mice: dichotomy of allogeneic resistance versus competitive advantage of disease-resistant marrow," J Immunol. 158(5):2435-2442 (1997).

Kawaski et al., "Prevention of type 1 diabetes: from the view point of β cell damage," Diabetes Res Clin Pract. 66:S27-S32 (2004).

Kieran et al., "The DNA binding subunit of NF-KB is identical to factor KBF1 and homologous to the rel oncogene product," Cell 62:1007-1018 (1990).

Klingensmith et al., "Vaccination with BCG at diagnosis does not alter the course of IDDM," abstract presented at the 31st research symposium on prevention of type I diabetes in general population. American Diabetes Association, Estes Park, Colorado, 27-29 (1996).

Koarada et al., "B Cells lacking RP105, A novel B cell antigen, in systemic lupus erythematosus," Arthritis & Rheumatism 42(12):2593-2600 (1999).

Kodama et al., "Islet regeneration during the reversal of autoimmune diabetes in NOD mice," Science. 302:1223-1227 (2003).

Kodama et al., "Regenerative medicine: A radical reappraisal of the spleen," Trends Mol Med. 11(6):271-276 (2005).

Kodama et al., "The therapeutic potential of tumor necrosis factor for autoimmune disease: A mechanically based hypothesis," Cell Mol Life Sci. 62:1850-1862 (2005).

Kopp and Ghosh, "Inhibition of NF-KB by sodium salicylate and aspirin," Science. 265:956-959 (1994).

Kouskoff et al., "Organ-specific disease provoked by systemic autoimmunity," Cell. 87:811-822 (1996) (Abstract Only).

Koyama et al., "Hox11 genes establish synovial joint organization and phylogenetic characteristics in developing mouse zeugopod skeletal elements," Development. 137: 3795, 2010 (Abstract Only).

Krause et al., "Multi-organ, multi-lineage engraftment by a single bone marrow-derived stem cell," Cell. 105:369-377 (2001).

Kuehnle and Goodell, "The therapeutic potential of stem cells from adults," BMJ. 325:372-376 (2002).

Kwon et al., "Evidence for involvement of the proteasome complex (26S) and NFKB in IL-1β-induced nitric oxide and prostaglandin production by rat islets and RINm5F Cells" Diabetes. 47:583-591 (1998).

Kwon et al., "Interleukin-1β -induced nitric oxide synthase expression by rat pancreatic β-cells: Evidence for the involvement of nuclear factor $_{k}B$ in the signaling mechanism," Endocrinology. 136(11):4790-4795 (1995).

Laakko et al., "Versatility of merocyanine 540 for the flow cytometric detection of apoptosis in human and murine cells," J Immunol Methods. 261:129-139 (2002).

Lahav-Baratz et al., "Reversible phosphorylation controls the activity of cyclosome-associated cyclin-ubiquitin ligase," Proc Natl Acad Sci USA 92:9303-9307 (1995).

Lakey et al., "BCG immunotherapy prevents recurrence of diabetes in islet grafts transplanted into spontaneously diabetic NOD mice," Transplantation. 57(8):1213-1217 (1994).

Lammert et al., "Induction of pancreatic differentiation by signals from blood vessels," Science. 294:564-567 (2001).

Lanza et al., "Transplantation of encapsulated canine islets into spontaneously diabetic BB/Wor rats without immunosuppression," Endocrinology. 131:637-642 (1992).

Lapchak et al., "Tumor necrosis factor production is deficient in diabetes-prone BB rats and can be corrected by complete Freund's adjuvant: A possible immunoregulatory role of tumor necrosis factor in the prevention of diabetes," Clin Immunol Immunopathol. 65(2):129-134 (1992).

Lawrence et al., "Differential hepatocyte toxicity of recombinant Apo2L/TRAIL versions," Nat Med. 7(4):383-385 (2001).

(56) References Cited

OTHER PUBLICATIONS

Lewis et al., "Integrins regulate the apoptotic response to DNA damage through modulation of p53" Proc Natl Acad Sci USA. 99(6):3627-3632 (2002).

Li and Faustman, "Use of donor β2-microglobulin-deficient transgenic mouse liver cells for isografts, allografts, and xenografts," Transplantation. 55(4):940-946 (1993).

Li et al., "Abnormal class I assembly and peptide presentation in the nonobese diabetic mouse," Proc Natl Acad Sci USA. 91:11128-11132 (1994).

Li et al., "Reduced expression of peptide-loaded HLA class I molecules on multiple sclerosis lymphocytes," Ann Neurol. 38:147-154 (1995).

Ljunggren et al., "MHC class I expression and CD8+ T cell development in TAP1/β2-microglobulin double mutant mice," Int Immunol. 7(6):975-984 (1995).

Macchi et al., "Impaired apoptosis in mitogen-stimulated lymphocytes of patients with multiple sclerosis," NeuroReport. 10:399-402 (1999).

Mak et al., "Signaling for survival and apoptosis in the immune system," Arthritis Res. 4(Suppl 3):S243-S252 (2002).

Markiewicz et al., "Long-term T cell memory requires the surface expression of self-peptide/major histocompatibility complex molecules," Proc Natl Sci USA. 95:3065-3070 (1998).

Markmann et al., "Indefinite survival of MHC class I-deficient murine pancreatic islet allografts," Transplantation. 54:1085-1089 (1992).

Marriott, "TNF-α antagonists: Monoclonal antibodies, soluble receptors, thalidomide and other novel approaches," Expert Opin Investig Drugs. 6(8):1105-1108 (1997).

Matsumoto et al., "Liver organogenesis promoted by endothelial cells prior to vascular function," Science. 294:559-563 (2001).

Mayer-Proschel et al., "Isolation of lineage-restricted neuronal precursors from multipotent neuroepithelial stem cells," Neuron. 19:773-785 (1997).

McGuire et al., "An enzyme related to the high molecular weight multicatalytic proteinases, macropain, participates in a ubiquitin-mediated, ATP-stimulated proteolytic pathway in soluble extracts of BHK 21/C13 fibroblasts," Biochim Biophys Acta. 967:195-203 (1988).

McInerney et al., "Prevention of insulitis and diabetes onset by treatment with complete Freund's adjuvant in NOD mice," Diabetes. 40:715-725 (1991).

McKay et al., "Mammalian deconstruction for stem cell reconstruction," Nat Med. 6:747-748 (2000).

Mercurio et al., "p105 and p98 precursor proteins play an active role in NF-Kappa B-mediated signal transduction," Genes Dev. 7:705-718 (1993).

Mestas et al., "Of mice and not Men: Differences between mouse and human immunology," J Immunol. 172:2731-2738 (2004).

Mezey et al., "Turning blood into brain: Cells bearing neuronal antigens generated in vivo from bone marrow," Science. 290: 1779-1782 (2000).

Miller et al., "Both the Lyt-2+ and L3T4+ T cell subsets are required for the transfer of diabetes in nonobese diabetic mice," J Immunol. 140:52-58 (1988).

Mittleman et al., "A phase I pharmacokinetic study of recombinant human tumor necrosis factor administered by a 5-day continuous infusion," Invest New Drugs. 10(3):183-190 (1992).

Miyazaki et al., "Predominance of T lymphocytes in pancreatic islets and spleen of pre-diabetic non-obese diabetic (NOD) mice: A longitudinal study," Clin Exp Immunol. 60:622-630 (1985).

Morrison, "Stem cell potential: Can anything make anything?" Curr Biol. 11:R7-R9 (2001).

Nomikos et al., "Combined treatment with nicotinamide and desferrioxamine prevents islet allograft destruction in NOD mice," Diabetes. 35:1302-1304 (1986).

Murthi et al., "Novel homeobox genes are differentially expressed in placental microvascular endothelial cells compared with macrovascular cells," Placenta. 29:624-630 (2008). (Abstract Only).

Offield et al., "PDX-1 is required for pancreatic outgrowth and differentiation of the rostral duodenum," Development. 122:983-995 (1996).

Ono et al., "IDDM in BB rats. Enhanced MHC Class I heavy-chain gene expression in pancreatic islets," Diabetes. 37:1411-1418 (1988).

Orlowski, "The multicatalytic proteinase complex, a major extralysosomal proteolytic system," Biochemistry. 29(45):10289-10297 (1990).

Osorio et al., "Beta-2 microglobulin gene disruption prolongs murine islet allograft survival in NOD mice," Transplant Proc. 26(2):752 (1994).

Palombella et al., "The ubiquitin-proteasome pathway is required for processing the NF-$_K$B1 precursor protein and the activation of NF-$_K$B," Cell. 78:773-785 (1994).

Pestano et al., "Inactivation of misselected CD8 T cells by CD8 gene methylation and cell death," Science. 284:1187-1191 (1999).

Petersen et al., "Bone marrow as a potential source of hepatic oval cells," Science. 284:1168-1170 (1999).

Pozzilli, "BCG vaccine in insulin-dependent diabetes mellitus," Lancet. 349:1520-1521 (1997).

Paolillo et al., "The effect of bacille calmette-guérin on the evolution of new enhancing lesions to hypointense T1 lesions in relapsing remitting MS," J Neurol. 250:247-248 (2003).

Pontesilli et al., "Circulating lymphocyte populations and autoantibodies in non-obese diabetic (NOD) mice: A longitudinal study," Clin Exp Immunol. 70:84-93 (1987).

Prieto et al., "Apoptotic rate: A new indicator for the quantification of the incidence of apoptosis in cell cultures," Cytometry. 48:185-193 (2002).

Qin et al., "Complete Freud's adjuvant-induced T cells prevent the development and adoptive transfer of diabetes in nonobese diabetic mice," J Immunol. 150:2072-2080 (1993).

Qin et al., "BCG vaccination prevents insulin-dependent diabetes mellitus (IDDM) in NOD mice after disease acceleration with cyclophosphamide," J Autoimmun.10:271-278 (1997).

Quintana et al., "Experimental autoimmune myasthenia gravis in naïve non-obese diabetic (NOD/LtJ) mice: Susceptibility associated with natural IgG antibodies to the acetylcholine receptor," Intl Immunol. 15:11-16 (2003).

Raab et al., "In vitro evaluation of methotrexate and azathioprine for antipsoriatic activity," Arch Derm Res. 253:77-84 (1975).

Rabinovitch et al., "TNF-α down-regulates type 1 cytokines and prolongs survival of syngeneic islet grafts in nonobese diabetic mice," J Immunol. 159:6298-6303 (1997).

Rabinovitch et al., "Tumor necrosis factor mediates the protective effect of freund's adjuvant against autoimmune diabetes in BB rats," J Autoimmun. 8:357-366 (1995).

Rajagopalan et al., "Pathogenic anti-DNA autoantibody-inducing T helper cell lines from patients with active lupus nephritis: Isolation of CD4-8- T helper cell lines that express the γδ T-cell antigen receptor," Proc Natl Acad Sci USA. 87:7020-7024 (1990).

Raju et al., "Characterization and developmental expression of Tlx-1, the murine homolog of HOX11," Mech Dev. 44:51-64 (1993).

Ramiya et al., "Reversal of insulin-dependent diabetes using islets generated in vitro from pancreatic stem cells," Nat Med. 6(3):278-282 (2000).

Rath el al., "TNF-induced signaling in apoptosis," J Clin Immuno1. 19(6):350-364 (1999).

Rechsteiner, "Ubiquitin-mediated pathways for intracellular proteolysis," Annu Rev Cell Biol. 3:1-30 (1987).

Rietze et al., "Purification of a pluripotent neural stem cell from the adult mouse brain," Nature. 412:736-739 (2001).

Ristori et al., "Use of Bacille Calmette-Guérin (BCG) in multiple sclerosis," Neurology. 53:1588-1589 (1999).

Roberts et al., "Hox11 controls the genesis of the spleen," Nature. 368:747-749 (1994).

Robertson et al., "Preservation of insulin mRNA levels and insulin secretion in HIT cells by avoidance of chronic exposure to high glucose concentrations," J Clin Invest. 90:320-325 (1992).

Roberts et al., "Developmental expression of Hox11 and specification of splenic cell fate," Am J Pathol. 146:1089-1101 (1995).

(56) References Cited

OTHER PUBLICATIONS

Robinson et al., "Elevated levels of cysteine protease activity in salive and salivary glands of the non obese diabetic (NOD) mouse model for Sjögren Syndrome," Proc Natl Acad Sci USA. 94:5767-5771 (1997).
Robinson et al., "A novel NOD-derived murine model of primary Sjogren's Syndrome," Arth Rheum. 41:150-156 (1998).
Rolfe et al., "The ubiquitin-mediated proteolytic pathway as a therapeutic area," J Mol Med. 75:5-17 (1997).
Rosenthal, "Prometheus's vulture and the stem-cell promise," n. Engl J Med. 349:67-274 (2003).
Ryu et al., "Reversal of established autoimmune diabetes by restoration of endogenous β cell function," J Clin Invest. 108:63-72 (2001).
Sadelan et al., "Prevention of type I diabetes in NOD mice by adjuvant immunotherapy," Diabetes. 39:583-589 (1990).
Sarin et al., "Cytotoxic effect of TNF and lymphotoxin on T lymphoblasts," J Immunol. 151:3716-3718 (1995).
Satoh et al., "Inhibition of type I diabetes in BB rats with recombinant human tumor necrosis factor-α ," J Immunol. 145(5):1395-1399 (1990).
Satoh et al., "Recombinant human tumor necrosis factor α suppresses autoimmune diabetes in non obese diabetic mice," J Clin Invest. 84:1345-1348 (1989).
Schatz et al., "Defective inducer T-cell function before the onset of insulin-dependent diabetes mellitus," J Autoimmun. 4:125-136 (1991).
Schmidt et al., "Interspecies exchange of β2-microglobulin and associated MHC and differentiation antigens," Immunogenetics. 13(6):483-49 (1981).
Schuppan, "Current concepts of Celiac Disease pathogenesis," Gastroenterology. 119:234- 242 (2000).
Sears et al., "NF-kB p105 processing via the ubiquitin-proteasome pathway," J Biol Chem. 273:1409-1419 (1998).
Serrano et al., "Non-HLA associations with autoimmune diseases," Autoimmun Rev. 5:209- 214 (2006).
Serup, "Panning for pancreatic stem cells," Nat Genet. 25:134-135 (2000).
Serup et al., "Islet and stem cell transplantation for treating diabetes," BMJ. 322:29-32 (2001).
Serreze et al., "Th1 to Th2 cytokine shifts in nonobese diabetic mice: Sometimes an outcome, rather than the cause, of diabetes resistance elicited by immunostimulation," J Immunol. 166:1352-1359 (2001).
Shehadeh et al., "Effect of adjuvant therapy on development of diabetes in mouse and man," Lancet. 343:706-707 (1994).
Shihabuddin et al., "Adult spinal cord stem cells generate neurons after transplantation in the adult dentate gyrus," J Neurosci. 20:8727-8735 (2000).
Shohami et al., "Dual role of tumor necrosis factor alpha in brain injury," Cytokine Growth Factor Rev. 10:119-130 (1999).
Singh et al., "Can progression of IDDM be prevented in newly diagnosed patients by BCG immunotherapy?" Diabetes Metab Rev. 13:320-321 (1997).
Silva et al., "Prevention of autoimmune diabetes through immunostimulation with Q fever complement-fixing antigen," Ann NY Acad Sci. 1005:423-430 (2003).
Slack, "Stem cells in epithelial tissues," Science. 287:1431-1433 (2000).
Song et al., "Tumor necrosis factor-related apoptosis-inducing ligand (TRAIL) is an inhibitor of autoimmune inflammation and cell cycle progression," J Exp Med. 191(7):1095-1103 (2000).
Speiser et al., "Loss of ATP-dependent proteolysis with maturation of reticulocytes and erythrocytes," J Biol Chem. 257(23):14122-14127 (1982).
Sreenan et al., "Increased β-Cell proliferation and reduced mass before diabetes onset in the nonobese diabetic mouse," Diabetes. 48:989-996 (1999).
Stephens et al., "Protection of NIT-1 pancreatic β-cells from immune attack by inhibition of NF-kB," J Autoimmun. 10:293-298 (1997).
Storms et al., "Hoechst dye efflux reveals a novel CD7+CD34- lymphoid progenitor in human umbilical cord blood," Blood. 96:2125-2133 (2000).
Sun et al., "MHC class I multimers," Arthritis Res. 9:265-269 (2001).
Szdoray et al., "Programmed cell death in rheumatoid arthritis peripheral blood T-cell subpopulations determined by laser scanning cytometry," Lab Invest. 83(12):1839-1848 (2003).
Shehadeh et al., "Repeated BCG vaccination is more effective than a single dose in preventing diabetes in non-obese diabetic (NOD) mice," Isr J Med Sci. 33(11):711-715 (1997).
Swirski et al., "Identification of splenic reservoir monocytes and their deployment to inflammatory sites," Science. 325:612-616 (2009).
Tamura et al., "In vivo differentiation of stem cells in the aorta-gonad-mesonephros region of mouse embryo and adult bone marrow," Exp Hematol. 30:957-966 (2002) (Abstract Only).
Tartaglia et al, "The two different receptors for tumor necrosis factor mediate distinct cellular responses," Proc Natl Acad Sci USA. 88:9292-9296 (1991).
Terada et al., "Bone marrow cells adopt the phenotype of other cells by spontaneous cell fusion," Nature. 416:542-545 (2002).
The Merck Manual of Diagnosis and Therapy, Beers and Berkow, Published by Merck Research Laboratories, 17th Ed., 165-171, 1999.
Toma et al., "Isolation of multipotent adult stem cells from the dermis of mammalian skin," Nat Cell Bio. 3:778-784 (2001).
Totpal et al., "TNF and its receptor antibody agonist differ in mediation of cellular responses," J Immunol. 153:2248-2257 (1994).
Townsley et al., "Dominant-negative cyclin-selective ubiquitin carrier protein E2-C/UbcH10 blocks cells in metaphase," Proc Natl Acad Sci USA. 94:2362-2367 (1997).
Trowsdale et al., "Sequences encoded in the class II region of the MHC related to the 'ABC' superfamily of transporters," Nature. 348:741-744 (1990).
Ulaeto et al., "A T-cell dormant state in the autoimmune process of nonobese diabetic mice treated with complete Freund's adjuvant," Proc Natl Acad Sci USA. 89:3927-3931 (1992).
Tran et al., "Reversal of Sjögren's-like Syndrome in non-obese diabetic mice," Ann Rheum Dis. 66:812-814 (2007).
Van der Kooy et al., "Why stem cells?," Science. 287:1439-1441 (2000).
Van Nocker et al., "The multiubiquitin-chain-binding protein Mcb1 is a component of the 26S proteasome in *Saccharomyces cerevisiae* and plays a nonessential, substrate-specific role in protein turnover," Mol Cell Biol. 16(11):6020-6028 (1996).
Van Noort et al., "Cell biology of autoimmune diseases," Int Rev Cytol. 178:127-204 (1998).
Vidal-Puig et al., "Tolerance to peripheral tissue Is transient and maintained by tissue-specific class I expression," Transplant Proc. 26:3314-3316 (1994).
Vogel et al., "Studies cast doubt on plasticity of adult cells," Science. 295:1989-1991 (2002).
Von Herrath et al., "In vivo treatment with a MHC class I-restricted blocking peptide can prevent virus-induced autoimmune diabetes," J Immunol. 161:5087-5096 (1998).
Wang et al., "Prevention of recurrence of IDDM in islet-transplanted diabetic NOD mice by adjuvant immunotherapy," Diabetes. 41:114-117 (1992).
Watt et al., "Out of eden: stem cells and their niches," Science. 287:1427-1430 (2000).
Waxman et al., "Demonstration of two distinct high molecular weight proteases in rabbit reticulocytes, one of which degrades ubiquitin conjugates," J Biol Chem. 262(6):2451-2457 (1987).
Weissman, "Translating stem and progenitor cell biology to the clinic: barriers and opportunities," Science. 287:1442-1446 (2000).
Weringer et al., "Identification of T cell subsets and Class I and Class II antigen expression in islet grafts and pancreatic islets of diabetic BioBreeding/Worcester rats," Am J Pathol. 132(1):292-303 (1988).
Wellik et al., "Hox11 paralogous genes are essential for metanephric kidney induction," Genes Dev. 16:1423-1432 (2002).
Wellik, "The role of Hox11 paralogous genes in prostate development," Grant Detail. (Abstract only) (2009).
Wicker et al., "Transfer of autoimmune diabetes mellitus with splenocytes from nonobese diabetic (NOD) mice," Diabetes. 35:855-860 (1986).

(56) References Cited

OTHER PUBLICATIONS

Willis et al., "Type 1 Diabetes in insulin-treated adult-onset diabetic subjects," Diabetes Res Clin Pract. 42:49-53 (1998).

Winston, "Embryonic stem cell research: the case for . . . ," Nat Med. 7:396-397 (2001).

Wong et al., "Identification of an MHC class I-restricted autoantigen in Type I Diabetes by screening an organ-specific cDNA library," Nat Med. 5:1026-1031 (1999).

Xu et al., "MHC/peptide tetramer-based studies of T cell function," J Immunol Methods. 268:21-28 (2002).

Yagi et al., "Possible mechanism of the preventive effect of BCG against diabetes mellitus in NOD Mouse. I. Generation of suppressor macrophages in spleen cells of BCG-vaccinated mice," Cell Immunol. 138:130-141 (1991).

Yagi et al., "Possible mechanism of the preventive effect of BCG against diabetes mellitus in NOD Mouse. II. Suppression of pathogenesis by macrophage transfer from BCG-vaccinated mice," Cell Immunol. 138:142-149 (1991).

Yan et al., "Reduced expression of Tap1 and Lmp2 antigen-processing genes in the nonobese diabetic (NOD) mouse due to a mutation in their shared bidirectional promoter," J Immunol. 159:3068-3080 (1997).

Yang et al., "Effect of tumor necrosis factor α on insulin-dependent diabetes mellitus in NOD Mice. I. The early development of autoimmunity and the diabetogenic process," J Exp Med. 180:995-1004 (1994).

Ying et al., "Changing potency by spontaneous fusion," Nature. 416:545-548 (2002).

Zöller et al., "Apoptosis resistance in peripheral blood lymphocytes of alopecia areata patients," J Autoimmun. 23(3):241-256 (2004).

Zulewski et al., "Multipotential nestin-positive stem cells isolated from adult pancreatic islets differentiate ex vivo into pancreatic endocrine, exocrine, and hepatic phenotypes," Diabetes. 50:521-533 (2001).

International Search Report for International Application No. PCT/US2004/037998, mailed Feb. 28, 2008.

Written Opinion for International Application No. PCT/US2004/037998, mailed Feb. 28, 2008.

Supplementary Partial European Search Report for European Application No. 0481753.4 (PCT/US2004/037998), dated Oct. 19, 2009.

\* cited by examiner

|  | Weeks after therapy initiation | | | | | |
|---|---|---|---|---|---|---|
|  | 1 | 2 | 3 | 4 | 5 | 6 |
| Group 1 | [Degree of insulitis (0-4)] | | | | | |
| NOD mrTNF 2.0 µg/injection, 3X/week, 3 weeks | | | | | | |
| #1 | 0 | 0 | 0 | 0 | 0 | 1 |
| #2 | 0 | 0 | 0 | 0 | 1 | 2 |
| #3 | 0 | 0 | 0 | 0 | 1 | 2 |
| #4 | 0 | 0 | 0 | 0 | 1 | 3 |
| Group 2 | | | | | | |
| NOD mrTNF 10µg/injection, 3X/week, 3 weeks | | | | | | |
| #1 | 1 | 1 | 1 | 1 | 2 | 2 |
| #2 | 1 | 1 | 0 | 1 | 2 | 3 |
| #3 | 1 | 1 | 1 | 2 | 2 | 4 |
| #4 | 1 | 0 | 1 | 1 | 2 | 3 |
| Group 3 | | | | | | |
| NOD mrTNF 4µg/injection, 3X/week, 3 weeks | | | | | | |
| #1 | 2 | 2 | 3 | 2 | 4 | 4 |
| #2 | 2 | 2 | 3 | 2 | 4 | IDDM |
| #3 | 1 | 1 | 2 | 2 | 4 | IDDM |
| #4 | 1 | 1 | 1 | 2 | 4 | IDDM |
| Group 4 | | | | | | |
| NOD, CFA, injection | | | | | | |
| #1 | 1 | 2 | 3 | No islets | No islets | No islets |
| #2 | 1 | 3 | 3 | No islets | IDDM | -- |
| #3 | 1 | 2 | 4 | 4 | 4 | 4 |
| #4 | 1 | 2 | 4 | 4 | 4 | IDDM |
| Group 5 | | | | | | |
| NOD, BCG, Injection | | | | | | |
| #1 | 1 | 1 | 1 | 2 | 3 | 4 |
| #2 | 1 | 1 | 1 | 2 | 3 | 4 |
| #3 | 1 | 1 | 1 | 2 | 4 | 4 |
| #4 | 1 | 1 | 2 | 2 | 4 | 4 |
| Group 6 | | | | | | |
| Control | | | | | | |
| #1 | 4+ | 4+ | 4+ | IDDM | Dead | |

Figure 4

Members of TNF/TNFR Superfamily

| Receptor | Standardized | Other Names | Accession | Human Chromosome | Mouse Chromosome | Phenotypes associated with mutations | Additional functional observations |
|---|---|---|---|---|---|---|---|
| NGFR | TNFRSF16 | p75 | M14764 | 17q21-q22 | 11, 55.6 cM | Defective sensory neuron innervation; impaired host sensitivity | |
| Troy | TNFRSF19 | Taj | AF167555 | 13q12.11-12.3 | 14 | | Expressed in hair follicles and epithelium; the mouse gene is located near the waved coat locus |
| EDAR | | | AF130988 | 2q11-q13 | 10, 29.0 cM | Hypohydrotic ectodermal dysplasia-abnormal tooth, hair and sweat gland formation | |
| XEDAR | | EDA-A2R | AF298812 | | X | | Likely role in skin, hair and tooth formation |
| CD40 | TNFRSF5 | p50, Bp50 | 260392 | 20q12-q13.2 | 2, 97.0 cM | Defective Ig class switching and GC formation causing immunodeficiency | |
| DcR3 | TNFRSF6B | | AF104419 | 20q13 | | | Secreted decoy receptor for FasL with possible role in tumor evasion |
| FAS | TNFRSF6 | CD95, APO-1, APT1 | M67454 | 10q24.1 | 19, 23.0 cM | Impaired activation-induced T cell death; lymphoproliferation autoimmunity (ALPS) | |
| OX40 | TNFRSF4 | CD134, ACT35, TXGF1L | X75962 | 1p36 | 4, 79.4 cM | Defective T cell responses | |
| AITR | TNFRSF18 | GITR | AF125304 | 1p36.3 | 4 | | Glucocorticoid-induced; inhibits T cell receptor-dependent apoptosis |
| CD30 | TNFRSF8 | KI-1, D1S166E | M83554 | 1p36 | 4, 75.5 cM | | Marker of Reed-Sternborg cells in Hodgkin's disease |

FIGURE 5

Members of TNF/TNFR Superfamily

| Receptor | Standardized | Other Names | Accession | Human Chromosome | Mouse Chromosome | Phenotypes associated with mutations | Additional functional observations |
|---|---|---|---|---|---|---|---|
| HveA | TNFRSF14 | MVEM, ATAR, TR2, LIGHTR | U70321 | 1p36.3-p36.2 | | | Probable role in T cell proliferation and receptor for herpes simplex virus |
| 4-1BB | TNFRSF9 | CD137, ILA | L12964 | 1p36 | 4, 75.5 cM | | Probable role in T cell responses |
| TNFR2 | TNFRSF1B | CD120b, p75, TNFBR, TNFR80, TNF-R-II | M32315 | 1p36.3-p36.2 | 4, 75.5 cM | Increased sensitivity to bacterial pathogens; decreased sensitivity to LPS; reduced antigen-induced T cell apoptosis. | |
| DR3 | TNFRSF12 | TRAMP, WSL-1, LARD, WSL-LR, DDR3, TR3, APO-3 | U72763 | 1p36.2 | | | A linked, partially duplicated copy of the gene encodes a potential decoy receptor |
| CD27 | TNFRSF7 | Tp55, S152 | M63928 | 12p13 | 6, 60.35 cM | Defective T cell responses | |
| TNFR1 | TNFRSF1A | CD120a, P55-R, TNFAR TNFR60 TNF-R-I | M75866 | 12p13.2 | 6, 60.55 cM | Impaired clearance of bacterial pathogens; resistance to LPS; LN present; defective GC formation; defective PP formation | |
| LTBR | TNFRSF3 | TNFR2-RP, TNFCR, TNF-R-RIII | L04270 | 12p13 | 6, 60.4 cM | Absence of LN, PP; defective GC formation | |
| RANK | TNFRSF11A | TRANCE-R | AF018253 | 18q22.1 | 11 | Osteopetrosis; absence of osteoclasts; absence of lymph node; PP present; abnormal B cell development | Required for lactating mammary gland development |
| TACI | | CAML interactor | AF023614 | 17p11 | | | Probable role in B cell responses |
| BCMA | TNFRSF17 | BCM | Z29574 | 16p13.1 | | | Probable role in B cell responses |
| DR6 | | TR7 | NM_014452 | 6p21.1-p12.2 | | | |

FIGURE 5 (Cont. 1/4)

Members of the TNF/FNFR Superfamily

| | Standardized | Other Names | Accession | Human Chromosome | Mouse Chromosome | Phenotypes associated with mutations | Additional functional observations |
|---|---|---|---|---|---|---|---|
| Receptor | | | | | | | |
| OPG | TNFRSF11B | OCIF, TR1 osteoprotegerin | U94332 | 8q24 | | Osteoporosis; arterial calcification | |
| DR4 | TNFRSF10A | Apo2, TRAILR-1 | U90875 | 8p21 | | | Probable inducer of lymphocyte death and activation |
| DR5 | TNFRSF10B | KILLER, TRICK2A, TRAIL-R2, TRICKB | AF012535 | 8p22-p21 | | | Probable inducer of lymphocyte death and activation |
| DcR1 | TNFRSF10C | TRAILR3, LIT, TRID | AF012536 | 8p22-p21 | | | GPI-linked decoy receptor - interferes with TRAIL signalling |
| DcR2 | TNFRSF10D | TRUNDD, TRAILR4 | AF029761 | 8p21 | | | Transmembrane decoy receptor - interferes with TRAIL signalling |
| Ligand | | | | | | | |
| EDA | | EDA1 | NM_001399 | Xq12-q13.1 | X, 37.0 cM | Hypohydrotic ectodermal dysplasia-abnormal tooth, hair and sweat gland formation | |
| CD40L | TNFSF5 | IMD3, HIGM1, TRAP, CD154, gp39 | X67878 | Xq26 | X, 18.0 cM | Defective T cell and Ig3 responses; hyper IgM syndrome | |
| FasL | TNFSF6 | APT1LG1 | U11821 | 1q23 | 1, 85.0 cM | Impaired activation-induced T cell death; lymphoproliferation autoimmunity (ALPS) | |

FIGURE 5 (Con't. 2/4)

Members of the TNF/TNFR Superfamily

| Receptor | Standardized | Other Names | Accession | Human Chromosome | Mouse Chromosome | Phenotypes associated with mutations | Additional functional observations |
|---|---|---|---|---|---|---|---|
| OX40L | TNFSF4 | gp34, TXGP1 | D90224 | 1q25 | 1, 84.9 cM | Defective T cell responses | |
| AITRL | TNFSF18 | TL6, hGITRL | AF125303 | 1q23 | | | Inhibits T cell receptor-dependent apoptosis |
| CD30L | TNFSF8 | | L09753 | 9q33 | 4, 32.2 cM | | Possible role in malignant lymphocyte disorders |
| VEGI | TNFSF15 | TL1 | AF039390 | | | | Potential molecular endothelial cell growth inhibitor |
| LIGHT | TNFSF14 | LTg, HVEML | AF036581 | 19 (probable) | 17 | | |
| 4-1BB-L | TNFSF9 | | U03398 | 19p13.3 | 17 | Defective T cell responses | |
| CD27L | TNFSF7 | CD70 | L08096 | 19p13 | 17, 20.0 cM | | |
| LTα | TNFSF1 | TNFB, LT | X01393 | 6p21.3 | 17, 19.06 cM | Absence of LN and PP; disorganized splenic microarchitecture; defective GC formation | |
| TNF | TNFSF2 | tumor necrosis factor, cachectin, TNFA, DIF | X01394 | 6p21.3 | 17, 19.06 | LN present; defective GC formation; increased susceptability to microbial pathogens | |
| LTβ | TNFSF3 | TNFC, p33 | L11015 | 6p21.3 | 17, 19.061 | Absence of peripheral LN and PP; presence of mesenteric and some cervical LN; defective GC formation | |

FIGURE 5 (Con't. 3/4)

| Members of the TNF/TNFR Superfamily | | | | | | |
|---|---|---|---|---|---|---|
| | Standardized | Other Names | Accession | Human Chromosome | Mouse Chromosome | Phenotypes associated with mutations | Additional functional observations |
| Receptor | | | | | | | |
| TWEAK | TNFSF12 | DR3L, APO3L | AF030099 | 17p13 | 11? | | Potential role in monocyte and NK cell cytotoxicity |
| APRIL | TNFSF13 | | NM_003808 | 17p13.1 | 11? | | Probable role in B cell responses |
| BLYS | TNFSF13B | BAFF, THANK, TALL1 | AF132600 | 13q32-34 | | | Probable role in B cell responses |
| RANKL | TNFSF11 | TRANCE, OPGL, ODF | AF013171 | 13q14 | 14, 45.0 | Osteopetrosis; absence of osteoclasts; absence pf lymph nodes; PP present; normal splenic architecture; abnormal B cell and T cell development | Required for lactating mammary gland development |
| TRAIL | TNFSF10 | Apo-2L, TL2 | U37518 | 3q26 | | | |

FIGURE 5 (Con't. 4/4)

INHIBITORS OF APOPTOSIS
Oncogene Research Products

| PRODUCT NAME | MOLECULAR WEIGHT | SEQUENCE | CAT. NO. | KNOWN TARGET CASPASES |
|---|---|---|---|---|
| A23187, Free Acid, *Streptomyces chartreusensis* | 523.6 | | 100105 | |
| A23187, Mixed Calcium-Magnesium Salt | | | 100106 | |
| N-Acetyl-L-cysteine | 163.2 | | 106425 | |
| Actinomycin D, *Streptomyces* sp. | 1255.5 | | 114666 | |
| 6-Amino-1,2-benzopyrone, Hydrochloride | 197.6 | | 130070 | |
| 5-Aminoisoquinolinone, Hydrochloride | 196.7 | | 164300 | |
| 3-Aminobenzamide | 136.2 | | 165350 | |
| ALLN | 383.5 | N-Acetyl-Leu-Nle-CHO | 208719 | |
| ALLN in Solution | 383.5 | | 208750 | |
| ALLM | 401.6 | N-Acetyl-Leu-Leu-Met-CHO | 208721 | |
| Anisomycin, *Streptomyces griseolus* | 265.3 | | 176880 | |
| Antimycin A3 | 520.6 | | 178205 | |
| Antimycin A3, 2-Methoxy- | 534.6 | | 178210 | |
| Aphidicolin | 338.5 | | 178273 | |
| Aurintricarboxylic Acid | 422.4 | | 189400 | |
| Baicalein | 270.2 | | 196322 | |
| BAPTA/AM | 764.7 | | 196419 | |
| *bcl-2* Antisense Oligonucleotide, Sodium Salt | 6058.6 | | 197208 | |
| *bcl-2* Antisense Oligonucleotide, Sodium Salt, Fluorescein-Labeled | 6634.1 | | 197211 | |
| *bcl-2* Antisense Oligonucleotide, Sodium Salt, Negative Control | 6058.6 | | 197210 | |
| *bcl-2* Antisense Oligonucleotide Set | | | 197212 | |
| *bcl-$x_s$* Antisense Oligonucleotide, Sodium Salt | 7426 | | 197203 | |
| *bcl-$x_s$* Antisense Oligonucleotide, Sodium Salt, Fluorescein-Labeled | 8001.5 | | 197206 | |
| *bcl-$x_s$ 2* Antisense Oligonucleotide, Sodium Salt, Negative Control | 7346.1 | | 197205 | |
| *bcl-$x_s$ 2* Antisense Oligonucleotide Set | | | 197214 | |
| Betulinic Acid | 456.7 | | 200498 | |
| BH3I-1 | 320.4 | | 286890 | |
| BH3I-2' | 556.5 | | 286891 | |
| Bongkrekic Acid, Triammonium Salt | 537.7 | | 203671 | |
| Caffeine | 194.2 | | 205548 | |
| Calpain Inhibitor III | 382.5 | Z-Val-Phe-CHO | 208722 | |
| Calpain Inhibitor IV | 557.7 | Z-Leu-Leu-Tyr-$CH_2$F | 208724 | |
| Calpain Inhibitor V | 407.5 | Mu-Val-HPh-$CH_2$F Mu = morpholinoure-idyl; HPh = homophenylalanyl | 208726 | |
| Calpain Inhibitor VI | 372.5 | 4-Fluorophenylsulfonyl-Val-Leu-CHO | 208745 | |
| Calpain Inhibitor Set | | | 208733 | |
| Calyculin A, *Discodermia calyx* | 1009.2 | | 208851 | |

Figure 6

| Caspase Active Site Peptide | 688.8 | | 235416 | |
|---|---|---|---|---|
| Caspase Inhibitor I | 467.5 | Z-Val-Ala-Asp(OMe)-CH$_2$F | 627610 | 1,3,4,7 |
| Caspase Inhibitor I, Biotin Conjugate | 672.8 | | 218742 | 1,3,4 |
| Caspase Inhibitor I, Cell-Permeable | 1827.3 | | 218830 | |
| Caspase Inhibitor I, Cell-Permeable in Solution | 1827.3 | Ac-Ala-Ala-Val-Ala-Leu-Leu-Pro-Ala-Val-Leu-Leu-Ala-Leu-Leu-Ala-Pro-Val-Ala-Asp-CHO | 218831 | |
| Caspase Inhibitor II | 329.4 | Ac-Val-Ala-Asp-CHO | 218735 | 1,3,4,7 |
| Caspase Inhibitor III | 263.3 | Boc-Asp-(OMe)-CH$_2$F | 218745 | All |
| Caspase Inhibitor IV | 355.8 | Boc-Asp(OBzl)-CMK | 218784 | 1 |
| Caspase Inhibitor V, Biotin Conjugate | 863.0 | Z-Val-Lys-X-(Biotin)-Asp(Ome)-CH$_2$F(x = linker) | 219000 | All |
| Caspase Inhibitor VI | 453.5 | Z-Val-Ala-Asp-CH$_2$F | 219007 | 1,3,4,7 |
| Caspase Inhibitor VII | 377.8 | Ac-Val-Ala-Asp-CMK | 218726 | 1,3,4,7 |
| Caspase Inhibitor VIII | 543.6 | Ac-Val-Asp-Val-Ala-Asp-CHO | 218729 | 2,3,7 |
| Caspase Inhibitor Negative Control | 386.4 | | 342000 | |
| Group III Caspase Inhibitor I | 610.6 | Z-Ala-Glu-(OMe)-Val-Asp(OMe)-CH$_2$F | 368620 | 6,8,9,10 |
| Group III Caspase Inhibitor II | 458.5 | Ac-Ala-Glu-Val-Asp-CHO | 368625 | 6,8,9,10 |
| Caspase Inhibitor Set I | | | 235429 | 1 |
| Caspase Inhibitor Set II | | | 218772 | 1,2,3,5,6,8,9 |
| Caspase Inhibitor Set III | | | 218806 | |
| Caspase Inhibitor Set IV | | | 218825 | |
| Caspase Inhibitor, Fluorogenic | 775.7 | DAcF$_{5,6}$-VAD-FMK | 218827 | 1,3,4,7 |
| Caspase-1 Inhibitor | 492.5 | Ac-Tyr-Val-Ala-Asp-CHO | 400010 | 1,4 |
| Caspase-1 Inhibitor, Cell-Permeable | 1990.5 | Ac-Ala-Ala-Val-Ala-Leu-Leu-Pro-Ala-Val-Leu-Leu-Ala-Leu-Leu-Ala-Pro-Tyr-Val-Ala-Asp-CHO | 400011 | 1,4 |
| Caspase-1 Inhibitor II | 541.0 | Ac-Tyr-Val-Ala-Asp-CMK | 400012 | 1,4 |
| Caspase-1 Inhibitor II, Biotin Conjugate | 725.3 | Biotin-Tyr-Val-Ala-Asp-CMK | 400022 | 1,4 |
| Caspase-1 Inhibitor III, Biotin Conjugate | 946.9 | Biotin-Tyr-Val-Ala-Asp-Fluoroacyloxy-methylketone | 400024 | 1,4 |
| Caspase-1 Inhibitor IV | 654.7 | Ac-Tyr-Val-Ala-Asp | 400015 | 1,4 |
| Caspase-1 Inhibitor V | 454.3 | Z-Asp-CH$_2$-DCB | 400019 | All |
| Caspase-1 Inhibitor VI | 630.7 | Z-Tyr-Val-Ala-Asp(OMe)-CH$_2$F | 218746 | 1,4 |

Figure 6 (Con't.)

| Caspase-1 Inhibitor VII, Biotin Conjugate | 938.1 | Ac-Tyr-Val-Lys(biotinyl)-Asp-2,6-Dimethyl-benzoyloxymethyl ketone | 218786 | 1 |
|---|---|---|---|---|
| Caspase-1 Inhibitor VIII | 611.6 | Ac-Trp-Glu-His-Asp-CHO | 218727 | 1,8 |
| Caspase-2 Inhibitor I | 695.7 | Z-Val-Asp-(OMe)-Val-Ala-Asp(OMe)-CH$_2$F | 218744 | 2 |
| Caspase-2 Inhibitor II | 603.6 | Ac-Leu-Asp-Glu-Ser-Asp-CHO | 218814 | 2 |
| Caspase-3 Inhibitor I | 502.5 | Ac-Asp-Glu-Val-Asp-CHO | 235420 | 3,6,7,8,10 |
| Caspase-3 Inhibitor I, Biotin Conjugate | 686.7 | Biotin-Asp-Glu-Val-Asp-CHO | 235422 | 3,6,7,8,10 |
| Caspase-3 Inhibitor I, Cell-Permeable | 2000.4 | Ac-Ala-Ala-Val-Ala-Leu-Leu-Pro-Ala-Val-Leu-Leu-Ala-Leu-Leu-Ala-Pro-Asp-Glu-Val-Asp-CHO | 235423 | 3,6,7,8,10 |
| Caspase-3 Inhibitor I, Cell-Permeable in Solution | 2000.4 | | 235427 | |
| Caspase-3 Inhibitor II | 668.7 | Z-Asp(OCH$_3$)-Glu(OCH$_3$)-Val-Asp-(OCH$_3$)-PMK | 264155 | 3,6,7,8,10 |
| Caspase-3 Inhibitor II in Solution | 668.7 | | 264156 | |
| Caspase-1 Inhibitor II, Biotin Conjugate | 873.0 | Biotin-X-Asp(OMe)-Glu(OMe)-Val-Asp(OMe)-CH$_2$F (X = Linker) | 218747 | 3,6,7,8,10 |
| Caspase-3 Inhibitor III | 551.0 | Ac-Asp-Glu-Val-Asp-CMK | 218750 | 3,6,7,8,10 |
| Caspase-3 Inhibitor IV | 533.6 | Ac-Asp-Met-Gln-Asp-CHO | 235421 | 3 |
| Caspase-3 Inhibitor V | 685.7 | Z-Asp(OMe)-Gln-Met-Asp(OMe)-CH$_2$F | 219002 | 3 |
| Caspase-3 Processing Inhibitor | 506.5 | Ac-Glu-Ser-Met-Asp-CHO | 218787 | 3 |
| Caspase-3/7 Inhibitor I | 324.4 | | 218826 | |
| Caspase-4 Inhibitor I | 500.6 | Ac-Leu-Glu-Val-Asp-CHO | 218755 | 4 |
| Caspase-4 Inhibitor I, Cell Permeable | 1998.5 | Ac-Ala-Ala-Val-Ala-Leu-Leu-Pro-Ala-Val-Leu-Leu-Ala-Leu-Leu-Ala-Pro-Leu-Glu-Val-Asp-CHO | 218766 | 4 |
| Caspase-5 Inhibitor I | 763.8 | Z-Trp-Glu(OMe)-His-Asp(OMe)-CH$_2$F | 218753 | 1,4,5 |
| Caspase-6 Inhibitor I | 652.7 | Z-Trp-Glu(OMe)-Ile-Asp(OMe)-CH$_2$F | 218757 | 6 |
| Caspase-6 Inhibitor II | 500.5 | Ac-Val-Glu-Ile-Asp-CHO | 218758 | 6 |

Figure 6 (Con't.)

| | | | | |
|---|---|---|---|---|
| Caspase-6 Inhibitor II, Cell Permeable | 1998.5 | Ac-Ala-Ala-Val-Ala-Leu-Leu-Pro-Ala-Val-Leu-Leu-Ala-Leu-Leu-Ala-Pro-Leu-Glu-Ile-Asp-CHO | 218767 | 6 |
| Caspase-8 Inhibitor I, Cell Permeable | 2000.4 | Ac-Ala-Ala-Val-Ala-Leu-Leu-Pro-Ala-Val-Leu-Leu-Ala-Leu-Leu-Ala-Pro-Ile-Glu-Thr-Asp-CHO | 218773 | 8, Granzyme B |
| Caspase-8 Inhibitor II | 654.7 | Z-Ile-Glu(OMe)-Thr-Asp(OMe)-CH$_2$F | 218759 | 8, Granzyme B |
| Caspase-8 Inhibitor II in Solution | 654.7 | | 218840 | |
| Caspase-9 Inhibitor I | 690.7 | Z-Leu-Glu(OMe)-His-Asp(OMe)-CH$_2$F | 218761 | 9 |
| Caspase-9 Inhibitor I in Solution | 690.7 | | 218841 | |
| Caspase-9 Inhibitor II, Cell Permeable | 2036.5 | Ac-Ala-Ala-Val-Ala-Leu-Leu-Pro-Ala-Val-Leu-Leu-Ala-Leu-Leu-Ala-Pro-Leu-Glu-His-Asp-CHO | 218776 | 9 |
| Caspase-9 Inhibitor III | 587.0 | Ac-Leu-Glu-His-Asp-CMK | 218728 | 9 |
| Caspase-13 Inhibitor I | 530.5 | Ac-Leu-Glu-Glu-Asp-CHO | 219005 | 13 |
| Caspase-13 Inhibitor II | 696.7 | Z-Leu-Glu(OMe)-Glu(OMe)-Asp-(OMe)-FMK | 219009 | 13 |
| Catalase, Human Erythrocytes | 256,000 | | 219008 | |
| Caspase Inhibitor, Negative Control | 386.4 | Z-Phe-Ala-FMK | 342000 | |
| Cycloheximide, High Purity | 281.3 | | 239764 | |
| Cyclosposporin A, *Tolypocladium inflatum* | 1202.6 | | 239835 | |
| 3,4-Dichloroisocoumarin | 215.0 | | 287815 | |
| Diisopropylfluorophosphate | 184.2 | | 30967 | |
| Disulfiram | 296.5 | | 322150 | 1, 3 |
| DPQ | 302.4 | | 300270 | |
| EMAPII Inhibitor | 556.6 | Z-Ala-Ser-Thr-Asp(OMe)-CH$_2$F | 324678 | |
| N-Ethylmaleimide | 125.1 | | 34115 | |
| Genistein | 270.2 | | 345834 | |
| Granzyme B Inhibitor I | 441.9 | Z-Ala-Ala-Asp-CH$_2$Cl | 368050 | 8, Granzyme B |
| Granzyme B Inhibitor II | 502.5 | Ac-Ile-Glu-Thr-Asp-CHO | 368055 | 8, Granzyme B |
| Granzyme B Inhibitor IV | 498.5 | Ac-Ile-Glu-Pro-Asp-CHO | 368056 | 8, Granzyme B |
| Grouo III Caspase Inhibitor I | 610.6 | Z-Ala-Glu-(OMe)-Val-Asp-(OMe)-CH$_2$F | 368620 | 6,8,9,10 |
| Grouo III Caspase Inhibitor II | 458.5 | Ac-Ala-Glu-Val-Asp-CHO | 368625 | |
| Guanosine 3', 5'-cyclic Monophosphate, Sodium Salt | 367.2 | | 370656 | |
| Hemoglobin, Bovine Erythrocytes | 64,500 | | 3745 | |
| Herbimycin A, *Streptomyces* sp. | 574.7 | | 375670 | |

Figure 6 (Con't.)

| | | | | |
|---|---|---|---|---|
| IL-1β Inhibitor | 593.6 | | 400700 | |
| Insulin-Like Growth Factor-I, Human, Recombinant, *E. coli* | 7500 | | 407240 | |
| Interleukin-1β, Human, Recombinant, *E. coli* | 17,000 | | 407615 | |
| Interleukin-6, Human, Recombinant, *E. coli* | 20,300 | | 407652 | |
| Leupeptin, Hemisulfate | 475.6 | Ac-Leu-Leu-arginal, hemisulfate | 108975 | |
| c-*myc* Antisense Oligonucleotide, Sodium Salt | 5165.7 | | 475959 | |
| c-*myc* Antisense Oligonucleotide, Negative Control, Sodium Salt | 5165.7 | | 475961 | |
| c-*myc* Antisense Oligonucleotide, Fluorescein-Labeled, Sodium Salt | 5741.3 | | 475962 | |
| *Noxa* Antisense Oligonucleotide, Sodium Salt | 6754 | | 492006 | |
| *Noxa* Antisense Oligonucleotide, Fluorescein-Labeled, Sodium Salt | 7329.5 | | 492009 | |
| *Noxa* Antisense Oligonucleotide, Negative Control, Sodium Salt | 6754 | | 492008 | |
| p53 Antisense Oligonucleotide, Sodium Salt | 6625.1 | | 506140 | |
| p53 Antisense Oligonucleotide, Fluorescein-Labeled, Sodium Salt | 7200.6 | | 506141 | |
| p53 Antisense Oligonucleotide, Negative Control, Sodium Salt | 6856 | | 506142 | |
| p53 Antisense Oligonucleotide, Negative Control, Fluorescein-Labeled, Sodium Salt | 6991.6 | | 506143 | |
| Phenylarsine Oxide | 168.0 | | 521000 | |
| Phenylmethylsulfonyl Fluoride | 174.2 | | 52332 | |
| Phorbol-12, 13-dibutyrate | 504.6 | | 524390 | |
| Phorbol-12-myristate-13-acetate | 616.8 | | 524400 | |
| Pifithrin-α | 367.3 | | 506132 | |
| Pifithrin-α, Cyclic | 349.3 | | 506134 | |
| PJ34 | 331.8 | | 528150 | |
| Puupehenone, *Hyrtios* sp. | 328.2 | | 540505 | |
| 1-Pyrrolidinecarbodithioic Acid, Ammonium Salt | 164.3 | | 548000 | |
| Spermine, Tetrahydrochloride | 348.3 | | 5677 | |
| Sulindac | 356.4 | | 574100 | |
| Sulindac Sulfide | 340.4 | | 574102 | |
| Sulindac Sulfone | 372.4 | | 574105 | |
| Superoxide Dismutase, Bovine Erythrocytes | 32,500 | | 574594 | |
| Superoxide Dismutase, Human, Recombinant, *E. coli* | | | 574595 | |
| Nα-Tosyl-Lys Chloromethyl Ketone, Hydrochloride | 369.3 | | 616382 | |
| TTFA | 222.2 | | 654050 | |
| (±)-Verapamil, Hydrochloride | 491.1 | | 676777 | |

Figure 6 (Con't.)

Summary of Apoptosis Kits

| Kit Type | Cat. No | Type of sample | Equipment Required | Measures |
|---|---|---|---|---|
| FragEL™ | QIA21<br>QIA33 | Slides of frozen or fixed cells or tissue | Light Microscope | DNA Fragmentation |
| FragEL™, Fluorescent | QIA39 | Slides of frozen or fixed cells or tissue; cell suspensions | Fluorescent Microscope or Flow Cytometer | DNA Fragmentation |
| Suicide Track™ DNA Ladder Isolation | AM41 | Cells | Agarose Electrophoresis | DNA Fragmentation |
| Annexin V | PF032<br>PF036 a | Live/Apoptotic Cells | Flow Cytometer or Flourescent Microscope | Externalized Phosphoserine |
| Nucleosome ELISA | QIA25 | Cells/Cell Lysates | Microplate Reader | Free Nucleosomes |
| Cell Death Detection | QIA20 | Cell Culture Supernatants | Microplate Reader | Nuclear Matrix Protein 41/7 |
| Cytochrome c Release | QIA87 | Cells | Immunoblotting Equipment, Homogenizer | Cytochrome c translocated from mitochondria to cytosol |
| Cytochrome c ELISA | QIA74 | Cell Lysates | Microplate Reader | Cytochrome c |
| MitoCapture™ | 475866 | Live/Apoptoic Cells | Flow Cytometer or Fluorescent Microscope | Mitochondrial Membrane Potential |
| Glutathione | QIA89 | Cells | Fluorescent Plate Reader or Fluorescent Microscope | Glutathione |
| Caspase Flow Cytometric | QIA78 | Intact Cells | Flow Cytometer or Fluorescent Microscope | General Caspase Activity |
| Caspase-3, Intracellular | 235430<br>235432 | Intact Cells | Flow Cytometer or Fluorescent Microscope | Caspase-3 Activity |
| Caspase Assays, Fluorometric | 218791 (Caspase-1)<br>218793 (Caspase-2)<br>QIA70 (Caspase-3)<br>HTS02 (Caspase-3)<br>218801 (Caspase-5)<br>218803 (Caspase-6)<br>QIA71 (Caspase-8)<br>HTS03 (Caspase-8)<br>QIA72 (Caspase-9)<br>HTS04 ((Caspase-9)<br>218811 (Caspase-10) | Cell Lysates | Fluorescent Microplate Reader | Caspase Activity |
| Caspase Assays, Colorimetric | 218790 (Caspase-1)<br>218734 (Caspase-1)<br>218792 (Caspase-2)<br>235419 (Caspase-3)<br>235418 (Caspase-3)<br>218801 (Caspase-5)<br>218802 (Caspase-6)<br>218824 (Caspase-9)<br>218810 (Caspase-10) | Cell Lysates | Microplate Reader | Caspase Activity | a. requires labeled streptavidin to be supplied by the user.

FIGURE 7

| Product Name | Mol Wt | Sequence | Known Target Caspases | Cat No. | Size |
|---|---|---|---|---|---|
| Acridine Orange | 301.8 | | | 113000 | 500 mg / 1 g |
| 7-Amino-4-methylcoumarin | 175.2 | | | 164545 | 10 mg |
| 7-Amino-4-(trifluoromethyl)coumarin | 229.2 | | | 164580 | 50 mg |
| Caspase Active Site Peptide | 688.8 | | | 235416 | 5 mg |
| Caspase Substrate I, Fluorogenic | 648.6 | Val-Ala-Asp-AFC | 1,3,4,7 | 218743 | 5 mg |
| Caspase Substrate Set I, Colorimetric | | | 1,3,6 | 218780 | 1 set |
| Caspase Substrate Set II, Fluorogenic | | | 1,2,3,4,5,6,9 | 218782 | 1 set |
| (New) Caspase Substrate Set III, Colorimetric | | | | 218808 | 1 set |
| (New) Caspase Substrate Set IV, Fluorogenic | | | | 218809 | 1 set |
| Caspase-1 Substrate I | 1584.7 | H-Asn-Glu-Ala-Tyr-Val-His-Asp | 1,4 | 400016 | 1 mg |
| Caspase-1 Substrate II, Fluorogenic | 1233.4 | DABCYL-Tyr-Val-Ala-Asp-Ala-Pro-Val-EDANS | 1,4 | 400018 | 500 µg |
| Caspase-1 Substrate III, Fluorogenic | 665.7 | Ac-Tyr-Val-Ala-Asp-AMC | 1,4 | 400020 | 1 mg / 5 mg |
| Caspase-1 Substrate IV, Colorimetric | 628.6 | Ac-Tyr-Val-Ala-Asp-pNA | 1,4 | 400025 | 5 mg |
| Caspase-1 Substrate V, Fluorogenic | 1145.1 | MCA-Tyr-Val-Ala-Asp-Ala-Pro-Lys(DNP)-OH | 1,4 | 400017 | 1 mg |
| Caspase-1 Substrate VI, Fluorogenic | 811.8 | Z-Tyr-Val-Ala-Asp-AFC | 1,4 | 668225 | 1 mg / 5 mg |
| Caspase-1 Substrate VII, Colorimetric | 747.7 | Ac-Trp-Glu-His-Asp-pNA | 1,4,5 | 218736 | 5 mg |
| Caspase-1 Substrate VIII, Fluorogenic | 1277.3 | | 1 | 218737 | 1 mg |
| Caspase-1 Substrate IX, Fluorogenic | 1144.2 | MCA-Tyr-Val-Ala-Asp-Ala-Pro-Lys-(DNP)-NH$_2$ | 1 | 218738 | 1 mg |
| Caspase-1 Substrate X, Fluorogenic | 784.8 | Ac-Trp-Glu-His-Asp-AMC | 1 | 218739 | 5 mg |
| Caspase-1 Substrate XI, Fluorogenic | 1318.3 | FITC-Tyr-Val-Ala-Asp-Ala-Pro-Lys-(DNP)-OH | 1 | 218795 | 1 mg |
| Caspase-1 Substrate XI, Standard | 855.9 | FITC-Tyr-Val-Ala-Asp-OH | 1 | 218796 | 1 mg |
| (New) Caspase-1 Substrate XII, Fluorogenic | 719.7 | Ac-Tyr-Val-Ala-Asp-AFC | 1 | 668224 | 5 mg |
| (New) Caspase-1 Substrate XIV, Water-Soluble, Colorimetric | 747.7 | Ac-Trp-Glu-His-Asp-pNA | 1,4,5 | 218822 | 5 mg |
| (New) Caspase-1/Caspase-4 Substrate I, Fluorogenic | 754.8 | Ac-Trp-Glu-Ala-Asp-AMC | 1,4 | 400005 | 1 mg / 5 mg |

FIGURE 7 (Cont. 1/4)

| Product Name | Mol. Wt. | Sequence | Known Target Caspases | Cat. No. | Size |
|---|---|---|---|---|---|
| Caspase-1/Caspase-4 Substrate II, Fluorogenic | 688.7 | Ac-Trp-Glu-Ala-Asp-AMC | 1,4 | 400006 | 1 mg<br>5 mg |
| Caspase-1/Caspase-4 Substrate III, Colorimetric | 681.7 | Ac-Trp-Glu-Ala-Asp-pNA | 1,4 | 400007 | 5 mg |
| Caspase-1/Caspase-4 Substrate IV | 651.7 | Ac-Trp-Val-Ala-Asp-pNA | 1,4 | 400008 | 5 mg |
| Caspase-2 Substrate I, Fluorogenic | 862.8 | Z-Val-Asp-Val-Ala-Asp-AFC | 2 | 218740 | 1 mg<br>5 mg |
| Caspase-2 Substrate II, Fluorogenic | 1270.3 | MCA-Val-Asp-Val-Ala-Asp-Gly-Trp-Lys-(DNP)-NH$_2$ | 2 | 218741 | 1 mg |
| (New) Caspase-2 Substrate III, Fluorogenic | 714.7 | MCA-Val-Asp-Val-Ala-Asp-Gly-Trp-Lys-(DNP)-NH$_2$ | 2 | 218815 | 5 mg |
| (New) Caspase-2 Substrate IV, Colorimetric | 680.7 | Ac-Val-Asp-Val-Ala-Asp-pNA | 2 | 218820 | 5 mg |
| (New) Caspase-2 Substrate V, Fluorogenic | 776.8 | Ac-Leu-Asp-Glu-Ser-Asp-AMC | 2 | 218818 | 1 mg<br>5 mg |
| Caspase-3 Substrate I, Colorimetric | 638.6 | Ac-Asp-Glu-Val-Asp-pNA | 3,6,7,8,10 | 235400 | 5 mg |
| Caspase-3 Substrate II, Fluorogenic | 675.6 | Ac-Asp-Glu-Val-Asp-AMC | 3,6,7,8,10 | 235425 | 1 mg<br>5 mg |
| Caspase-3 Substrate III, Fluorogenic | 1155.1 | MCA-Asp-Glu-Val-Asp-Ala-Pro-Lys-(DNP)-OH | 3,6,7,8,10 | 235426 | 1 mg |
| Caspase-3 Substrate IV, Fluorogenic | 821.7 | Z-Asp-Glu-Val-Asp-AFC | 3,6,7,8,10 | 264150 | 1 mg<br>5 mg |
| Caspase-3 Substrate V, Fluorogenic | 1359.4 | MCA-Val-Asp-Gln-Met-Asp-Gly-Trp-Lsy-(DNP)-NH$_2$ | 3 | 218751 | 1 mg |

FIGURE 7 (Cont. 2/4)

| Product Name | Mol. Wt. | Sequence | Known Target Caspases | Cat No. | Size |
|---|---|---|---|---|---|
| Caspase-3 Substrate VI, Fluorogenic | 1213.2 | MCA-Asp-Glu-Val-Asp-Ala-Arg-Lys-(DNP)-NH$_2$ | 3,6,7,8,10 | 218752 | 1 mg |
| Caspase-3 Substrate VII, Fluorogenic | 728.6 | Ac-Asp-Glu-Val-Asp-AFC | 3,6,7,8,10 | 264151 | 1 mg<br>5 mg |
| (New) Caspase-3 Substrate VIII, Water Soluble, Colorimetric | 638.6 | Ac-Asp-Glu-Val-Asp-pNA | 3,6,7,8,10 | 218823 | 5 mg |
| Caspase-4 Substrate I, Fluorogenic | 1227.3 | MCA-Leu-Glu-Val-Asp-Gly-Trp-Lys-(DNP)-NH$_2$ | 4 | 218756 | 1 mg |
| Caspase-4 Substrate II, Fluorogenic | 727.7 | Ac-Leu-Glu-Val-Asp-AFC | 4 | 218748 | 1 mg<br>5 mg |
| Caspase-5 Substrate II, Fluorogenic | 838.8 | Ac-Trp-Glu-His-Asp-AFC | 1,4,5 | 218754 | 1 mg<br>5 mg |
| Caspase-6 Substrate I, Fluorogenic | 673.7 | Ac-Val-Glu-Ile-Asp-AMC | 6 | 218760 | 5 mg |
| Caspase-6 Substrate II, Colorimetric | 636.7 | Ac-Val-Glu-Ile-Asp-pNA | 6 | 218762 | 5 mg |
| Caspase-6 Substrate III, Fluorogenic | 819.8 | Z-Val-Glu-Ile-Asp-AFC | 6 | 218763 | 5 mg |
| Caspase-6 Substrate V, Fluorogenic | 751.7 | Ac-Val-Glu-His-Asp-AFC | 6,9,10 | 218788 | 1 mg<br>5 mg |
| Caspase-6 Substrate VI, Fluorogenic | 744.8 | Ac-Val-Lys-Met-Asp-AFC | 6 | 218789 | 1 mg<br>5 mg |
| Caspase-6 Substrate VII, Fluorogenic | 712.7 | Ac-Val-Asn-Leu-Asp-AFC | 6 | 219003 | 1 mg<br>5 mg |

FIGURE 7 (Cont. 3/4)

| Product Name | Mol Wt. | Sequence | Known Target Caspases | Cat. No. | Size |
|---|---|---|---|---|---|
| Caspase-7 Substrate I, Fluorogenic | 1327.3 | MCA-Val-Asp-Gln-Val-Asp-Gly-Trp-Lys-(DNP)- $NH_2$ | 7 | 218768 | 1 mg |
| Caspase-9 Substrate I, Fluorogenic | 765.7 | Ac-Leu-Glu-His-Asp-AFC | 4,5,9 | 218765 | 1 mg 5 mg |
| Caspase-13 Substrate I, Colorimetric | 666.6 | Ac-Leu-Glu-Glu-Asp-pNA | 13 | 219006 | 5 mg |
| (New) DRONC Substrate I, Fluorogenic | 730.7 | Ac-Thr-Gln-Thr-Glu-AFC | | 287990 | 1 mg 5 mg |
| DRONC Substrate II, Fluorogenic | 716.6 | AC-Thr-Gln-Thr-Asp-AFC | | 287995 | 1 mg 5 mg |
| (New) DRONC Substrate III, Fluorogenic | 786.7 | Ac-Gly-Ile-Glu-Thr-Asp-AFC | | 287996 | 1 mg 5 mg |
| (New) DRONC Substrate IV, Fluorogenic | 716.8 | Ac-Val-Asp-Val-Ala-Asp-AMC | | 287997 | 1 mg 5 mg |
| (New) $D_2R$ | 560.5 | | | 251300 | 1 mg |
| (New) $(DMe)_2R$ | 588.6 | | | 251305 | 1 mg |
| Granzyme B Enzyme Overlay Membrane | | Z-Ala-Ala-Asp-AFC | 8,Granzyme B | 368045 | 1 sheet |
| Granzyme B Substrate I, Colorimetric | 638.6 | Ac-Ile-Glu-Thr-Asp-AFC | 8,Granzyme B | 368057 | 5 mg |
| Granzyme B Substrate II, Fluorogenic | 821.8 | Z-Ile-Glu-Thr-Asp-AFC | 8,Granzyme B | 368059 | 1 mg 5 mg |
| Granzyme B Substrate IV | 481.6 | Boc-Ala-Ala-Asp-5-benzyl | 8,Granzyme B | 368063 | 5 mg |
| (New) Granzyme B Substrate VI | 827.9 | Ac-Ile-Glu-Pro-Asp-Trp-Gly-Ala- $NH_2$ | Granzyme B | 368065 | 5 mg |
| (New) Granzyme B Substrate VII | 884.9 | Ac-Ile-Glu-Pro-Asp-Trp-Asn-Ala-$NH_2$ | Granzyme B | 368066 | 5 mg |
| (New) Granzyme B Substrate VIII, Colorimetric | 634.6 | Ac-Ile-Glu-Pro-Asp-pNA | Granzyme B | 368067 | 5 mg |
| (New) Granzyme B Substrate IX, Fluorogenic | 671.7 | Ac-Ile-Glu-Pro-Asp-AMC | Granzyme B | 368068 | 1 mg 5 mg |
| (New) Granzyme B Substrate X, Fluorogenic | 725.0 | Ac-Ile-Glu-Pro-Asp-AMC | | 368062 | 5 mg |
| p-Nitroaniline | 138.1 | | | 483350 | 50 g |

FIGURE 7 (Cont. 4/4)

| Product Name | Mol. Wt. | Cat. No. | Size |
|---|---|---|---|
| A23187, Free Acid, *Streptomyces chartreusensis* | 523.6 | 100105 | 1 mg<br>5 mg<br>10 mg<br>50 mg |
| A23187, Mixed Calcium-Magnesium salt | | 100106 | 10 mg |
| N-Acetyl-L-cysteine | 163.2 | 106425 | 5 g |
| Actinomycin D, *Streptomyces sp.* | 1255.5 | 114666 | 1 set<br>5 mg |
| Actinomycin D, 7-Amino- | 1270.4 | 129935 | 1 mg |
| AG 17 | 282.4 | 658425 | 5 mg |
| AG 82 | 202.2 | 658400 | 5 mg |
| AG 490 | 294.3 | 658401 | 5 mg |
| AG 1714 | 199.2 | 121780 | 25 mg |
| Anandamide | 347.5 | 172100 | 5 mg |
| Anisomycin, *Streptomyces griseolus* | 265.3 | 176880 | 10 mg |
| Aphidicolin | 338.5 | 178273 | 1 mg |
| (New) Apoptosis Inducer Set I | | 128486 | 1 set |
| (New) Apoptosis Inducer Set II | | 178489 | 1 set |
| Bafilomycin A1, *Streptomyces griseus* | 622.8 | 196000 | 10 µg |
| (New) Bak BH3 Fusion Peptide, Cell-Permeable | 4404.2 | 196350 | 500 µg |
| (New) Bak BH3 Fusion Peptide, Cell-Permeable Negative Control | 4362.2 | 196355 | 500 µg |
| (New) Bcl-2 Binding Peptide, Cell-Permeable | 3399.9 | 197220 | 1 mg |
| (New) Bcl-2 Binding Peptide, Cell-Permeable, Negative Control | 3357.8 | 197225 | 1 mg |
| Berberine Hemisulfate | 384.4 | 200400 | 1 g |
| Betulinic Acid | 456.7 | 200498 | 5 mg |
| Bleomycin Sulfate, *Streptomyces verticillus* | | 203401 | 15 U |
| (New) CAFdA | 303.7 | 205500 | 1 mg |
| Calphostin C, *Cladosporium cladosporioides* | 790.8 | 208725 | 50 µg<br>100 µg |
| Camptothecin, *Camptotheca acuminata* | 348.4 | 208925 | 50 mg |
| CAPE | 284.3 | 211200 | 25 mg |
| Chelerythrine Chloride | 383.8 | 220285 | 5 mg |

FIGURE 8

| Product Name | Mol. Wt. | Cat. No. | Size |
|---|---|---|---|
| 2-Chloro-2'-deoxyadenosine | 285.7 | 220467 | 10 mg |
| 2-Chloro-2'-deoxyadenosine 5'-Triphosphate, Tetralithium Salt | 549.4 | 220469 | 1 mg |
| Colcemid | 371.4 | 234109 | 5 mg |
| Colchicine, *Colchicum autumnale* | 399.4 | 234115 | 1 g<br>5 g |
| Corticosterone | 346.5 | 235135 | 1 g |
| Cycloheximide | 281.3 | 239763 | 1 g<br>5 g |
| (New) Cycloheximide, High Purity | 281.3 | 239764 | 100 mg<br>1 g |
| Cyclophosphamide Monohydrate | 279.1 | 239785 | 1 g |
| Cyclosporin A, *Tolypocladium inflatum* | 1202.6 | 239835 | 100 mg |
| Daunorubicin, Hydrochloride | 564.0 | 251800 | 5 mg |
| Dexamethasone | 392.5 | 265005 | 100 mg |
| (New) 2,3-Dichloro-5,8-dihydroxy-1,4-naphthoquinone | 259.1 | 287805 | 50 mg |
| 3,3'-Diindolymethane | 246.3 | 309900 | 100 mg |
| (New) Dolastatin 15 | 837.1 | 320900 | 1 mg |
| Doxorubicin, Hydrochloride | 580.0 | 324380 | 10 mg |
| (-)-Epigallocatechin Gallate | 458.4 | 324880 | 10 mg |
| Erbstatin Analog | 194.2 | 324930 | 1 mg |
| Etoposide | 588.6 | 341205 | 25 mg |
| Etoposide Phosphate | 668.6 | 341206 | 5 mg |
| ET-18-OCH$_3$ | 523.7 | 341207 | 5 mg |
| 5-Fluorouracil | 130.1 | 343922 | 1 g |
| Folimycin, *Streptomyces sp.* | 866.1 | 344085 | 10 μg |
| Forskolin, *Coleus forskohlii* | 410.5 | 344270 | 10 mg<br>25 mg<br>50 mg |
| H-7, Dihydrochloride | 364.3 | 371955 | 1 mg<br>5 mg |
| Genistein | 270.2 | 345834 | 20 mg<br>50 mg |
| (New) (6)-Gingerol, *Zingiber officinale* | 294.4 | 345868 | 5 mg |
| Glycodeoxycholic Acid, Sodium Salt | 471.6 | 361311 | 5 g |
| H-7, Dihydrochloride | 364.3 | 371955 | 1 mg<br>5 mg |
| H-89, Dihydrochloride | 519.3 | 371963 | 1 mg |

FIGURE 8 (Cont. 1/5)

| Product Name | Mol. Wt. | Cat. No. | Size |
|---|---|---|---|
| (New) HA14-1 | 409.2 | 371971 | 1 set<br>2 mg |
| Harringtonine, *Cephalotaxus hainanensis* | 531.6 | 372125 | 5 mg |
| Homoharringtonine, *Cephalotaxus hainanensis* | 546.6 | 384500 | 5 mg |
| HMBA | 200.3 | 387750 | 500 mg |
| 4-Hydroxynonenal | 156.2 | 393204 | 1 mg |
| 4-Hydroxyphenylretinamide | 391.6 | 390900 | 5 mg |
| Hydroxyurea | 76.1 | 400046 | 5 g |
| (New) Indanocine | 339.4 | 402080 | 1 mg |
| Ionomycin, Free Acid, *Streptomyces conglobatus* | 709.0 | 407950 | 1 mg<br>5 mg<br>10 mg |
| Ionomycin, Calcium Salt, *Streptomyces conglobatus* | 747.1 | 407952 | 1 mg<br>5 mg<br>10 mg<br>25 mg |
| (New) Kaempferol | 286.2 | 420345 | 25 mg |
| KN-93 | 501.0 | 422708 | 1 mg<br>5 mg |
| (New) Licochalcone-A, Synthetic | 338.4 | 435800 | 10 mg<br>50 mg |
| Methotrexate | 454.5 | 454125 | 100 mg |
| Mitomycin C, *Streptomyces caespitosus* | 334.3 | 47589 | 2 mg |
| Mitomycin C, *Streptomyces caespitosus*, Carrier-Free | 334.3 | 475820 | 10 mg |
| (New) MT-21 | 281.4 | 475952 | 10 mg |
| (New) MT-21, Negative Control | 169.2 | 475953 | 5 mg |
| (New) Muristerone A, *Ipomoea spp* | 496.6 | 475946 | 1 mg |
| (±)-S-Nitroso-N-acetylpenicillamine | 220.2 | 487910 | 1 set<br>20 mg |
| S-Nitrosoglutathione | 336.3 | 487920 | 1 set<br>10 mg<br>50 mg |
| Okadaic Acid, *Prorocentrum concavum* | 805.0 | 495604 | 10 µg<br>25 µg<br>100 µg |
| Oligomycin | | 495455 | 10 mg |
| (New) p53 Activator, Cell-Permeable | 4434.1 | 506131 | 500 µg |
| Paclitaxel, *Taxus sp.* | 853.9 | 580555 | 5 mg<br>25 mg<br>100 mg |

FIGURE 8 (Cont. 2/5)

| Product Name | Mol. Wt. | Cat. No. | Size |
|---|---|---|---|
| Phorbol-12-myristate-13-acetate | 616.8 | 524400 | 1 mg<br>5 mg<br>10 mg<br>25 mg |
| (Pivaloyloxy)methyl Butyrate | 202.3 | 527998 | 25 mg |
| Puromycin, Dihydrochloride | 544.4 | 540222 | 25 mg<br>100 mg |
| 1-Pyrrolidinecarbodithiolic Acid, Ammonium Salt | 164.3 | 548000 | 100 mg |
| Quercetin, Dihydrate | 338.3 | 551600 | 100 mg |
| Rapamycin | 914.2 | 553210 | 100 μg<br>1 mg |
| (New)(-)-Reveromycin B, Synthetic | 660.8 | 554719 | 50 μg |
| (New) Scriptaid | 326.4 | 565730 | 5 mg |
| (New) Smac-N7 Peptide | 725.9 | 567370 | 1 mg<br>5 mg |
| (New) Smac-N7 Peptide, Cell-Permeable | 3051.7 | 567375 | 1 mg |
| Sodium Butyrate | 110.1 | 567430 | 250 mg |
| Sodium 4-Phenylbutyrate | 186.2 | 567616 | 100 mg |
| Spermine, Tetrahydrochloride | 348.3 | 5677 | 5 g |
| D-erythro-Sphingosine, Free Base, Bovine Brain | 299.5 | 567725 | 10 mg |
| D-erythro-Sphingosine, Free Base, Bovine Brain, High Purity | 299.5 | 567726 | 10 mg |
| D-erythro-Sphingosine, N-Acetyl- | 341.5 | 110145 | 5 mg |
| D-erythro-Sphingosine, N,N-Dimethyl- | 327.6 | 310500 | 5 mg |
| D-erythro-Sphingosine, N-Hexanoyl- | 397.6 | 376650 | 5 mg |
| D-erythro-Sphingosine, N-Octanoyl- | 425.7 | 219540 | 5 mg |
| Staurosporine, Streptomyces sp. | 466.5 | 569397 | 100 μg<br>200 μg |
| (New) Sulfasalazine | 398.4 | 573500 | 100 mg |
| Sulindac | 356.4 | 574100 | 1 g |
| Tamoxifen Citrate | 563.7 | 579000 | 100 mg |
| Tamoxifen, 4-Hydroxy-, (2)- | 387.5 | 579002 | 5 mg |
| Sulindac Sulfide | 340.4 | 574102 | 5 mg |
| Thapsigargin | 650.8 | 586005 | 1 mg |
| a-Toxin, Staphylococcus aureus | 33,000 | 616385 | 250 μg |
| (New) TRAIL, Human, Recombinant, E. coli | 23,000 | 616375 | 100 μg |
| Trichostatin A, Streptomyces sp. | 302.4 | 647925 | 1 mg |

FIGURE 8 (Cont. 3/5)

| Product Name | Mol. Wt. | Cat. No. | Size |
|---|---|---|---|
| (New) O-Trensox | 899.9 | 499300 | 10 mg |
| (New) Topotecan, Hydrochloride | 457.9 | 614800 | 1 mg |
| Valinomycin, *Streptomyces fulvissimus* | 1111.3 | 676377 | 25 mg<br>100 mg |
| (±)-Verapamil, Hydrochloride | 491.1 | 676777 | 100 mg |
| Veratridine | 673.8 | 676950 | 5 mg |
| Vicenistatin | 500.7 | 676790 | 500 µg |
| Vitamin $D_3$, 1α,25-Dihydroxy- | 416.7 | 679101 | 50 µg |
| Vitamin E Succinate | 530.8 | 679130 | 100 mg |

FIGURE 8 (Cont. 4/5)

| Agent | Dose | Solvent for Stock Solution | Cat. No. |
|---|---|---|---|
| Actinomycin D | 500 ng/ml | Methanol | 114666 |
| Aphidocolin | 2 µg/ml | DMSO | 178273 |
| A23187 | 10 µg | DMSO | 100105 |
| Caffeine | 16mM | Boiling $H_2O$ | 205548 |
| Camptothecin | 4 µg/ml | DMSO | 208925 |
| Cycloheximide | 100 µg/ml | $H_2O$ | 239764 |
| Dexamethasone | 1µM | Ethanol | 265005 |
| Doxorubicin (Adriamycin) | 0.2 µg/ml | $H_2O$ | 324380 |
| 5-Fluorouracil | 25 µg/ml | DMSO, Hot $H_2O$ | 343922 |
| Hydroxyurea | 500 nM | $H_2O$ | 400046 |
| Paclitaxel (TAXOL) | 100-580 nM | DMSO | 580555 |
| Staurosporine | 500 nM | DMSO | 569397 |
| Thymidine | 2 mM | PBS | 6060 |
| Vinblastine | 60 nM | Methanol | 677175 |

FIGURE 8 (Cont. 5/5)

| Group | Mouse Number | Injected Cells | Days after Tx | Analyzed organ | Whole GFP+ | %H2K+GFP+ | CD3+GFP+ | B220+GFP+ | Mac-1+GFP+ |
|---|---|---|---|---|---|---|---|---|---|
| 1 | 889 | Splenocytes | 41 | PBL | 0.59 | | | | |
| 2 | 910 | Splenocytes | 152 | PBL | 0.02 | | | 0 | 0.02 |
| 2 | 911 | Splenocytes | 155 | PBL | 0.01 | | | 0.03 | 0.02 |
| 2 | 903 | Splenocytes | 152 | PBL | 0.04 | | | 0.25 | 0.02 |
| 2 | 910 | Splenocytes | 179 | Sp | 0.2 | | 0 | | |
| 2 | 911 | Splenocytes | 182 | Sp | 0.31 | | 0.1 | | |
| 2 | 903 | Splenocytes | 179 | Sp | 0.71 | | | | |
| | | | | Mean | 0.023 | | | | |
| | | | | SD | 0.015 | | | | |
| 2 | 910 | Splenocytes | 179 | Sp | 0.13 | | | 0.02 | 0.02 |
| 2 | 911 | Splenocytes | 182 | Sp | 0.34 | | | 0.03 | 0.02 |
| 2 | 903 | Splenocytes | 179 | Sp | 0.67 | | 0 | 0.32 | 0.02 |
| | | | | Mean | | | 0.1 | | |
| 2 | 931 | Splenocytes | 98 | Sp | 13.3 | 6.2 | 2.6 | 3.4 | 1.1 |
| 2 | 939 | Splenocytes | 87 | Sp | 4.7 | 4.2 | 1.5 | 1.6 | 0.2 |
| 2 | 932 | Splenocytes | 90 | Sp | 6.7 | 3.9 | 1.5 | 2.7 | 0.2 |
| 2 | 933 | Splenocytes | 98 | Sp | 8.2 | 6.3 | 2.8 | 3.3 | 0.1 |
| | | | 93.3 | Mean | 8.2 | 5.2 | 2.1 | 2.8 | 0.4 |
| | | | | SD | 3.7 | 1.3 | 0.7 | 0.8 | 0.5 |
| 3 | 890 | Bone Marrow | 56 | Sp | 1.9 | | | | |
| 3 | 898 | Bone Marrow | 41 | PBL | 4.76 | | | | 0 |
| | | | | Mean | 3.33 | | | | 0.04 |
| 4 | 905 | Bone Marrow | 155 | PBL | 0.05 | | | 0.04 | |
| 4 | 898 | Bone Marrow | 168 | PBL | 0.23 | | | 0.23 | |
| 4 | 898 | Bone Marrow | 195 | PBL | 0.21 | | 0.03 | 0.5 | 0.2 |
| 4 | 905 | Bone Marrow | 182 | PBL | 0.56 | | 0.06 | 1.1 | 0.2 |
| 4 | 940 | Bone Marrow | 98 | Sp | 1.9 | 1.5 | 0.4 | | |
| 4 | 934 | Bone Marrow | 98 | Sp | 3 | 2.26 | 1.1 | | |
| | | | | Mean | 2.45 | 1.88 | 0.75 | 0.8 | 0.2 |
| 5 | 979 | Hoechst 3342/SP | 40 | PBL | 0.01 | | | | |
| 5 | 979 | Hoechst 3342/SP | 40 | PBL | 0.01 | | | | |
| 7 | 894 | CNS | 41 | PBL | 0.19 | | 0.01 | 0.05 | 0.02 |
| 7 | 894 | CNS | 168 | PBL | 0 | | | | |
| 7 | 894 | CNS | 195 | Sp | 0.35 | | | | |
| 9 | 906 | HC | 155 | PBL | 0.02 | | 0.02 | 0.05 | 0.11 |
| 9 | 909 | HC | 155 | PBL | 0.01 | | 0.09 | 0.02 | 0.03 |
| 9 | 906 | HC | 155 | Sp | 0.45 | | | | |
| 9 | 909 | HC | 182 | Sp | 0.27 | | | | |

FIGURE 9

| Group Factor | Stem Cell Injection Frequency | Blood Glucose After Graft Removal | Invasion | Islet-Histology Circumferential | No Accumulation | Regeneration Growth of Islet Size | Chimerism GFP or Y chromosome | Stem Cell Population | Expression of TNFRII |
|---|---|---|---|---|---|---|---|---|---|
| (Autoimmune Model) | | | | | | | | | |
| NOD Isografts | (-) | Poor | (+++) | (+) | (-) | (-) | (-) | (-) | |
| NOD Isografts with CFA | (-) | Poor | (++) | (+) | (-) | | (-) | (-) | |
| NOD Isografts with Fl Sp | | Excellent | (-) | (±) | (+++) | (+++) | High | (+++) | |
| NOD Isografts with CFA and Fl Sp | High (40 days) | Poor | | | | | | | |
| NOD Isografts with TNF-α (Low dose) and Fl Sp | High (40 days) | | (±) | (++) | (+) | (++) | | | |
| (STZ model) | | | | | | | | | |
| GFP Sp without Isografts (No islet transplants) | | Poor | (+++) | (+) | (-) | (-) | LowPBL 120 Days | (-) | |
| GFP BM without Isografts (No islet transplants) | | Poor | (+++) | (+) | (-) | (-) | LowPBL 120 Days | (-) | |
| C57BL/6 Isografts with (+glucose clamp) | | Excellent | | | | | | | |
| C57BL/6 Isografts with TNF-α (2 µg) | | Excellent | | | | | (++) | | |
| C57BL/6 Isografts with GFP Sp (120 days n=10) | | Excellent | | | | | (+) | | |
| C57BL/6 Isografts with GFP BM (120 days n=9) | | Moderate to Poor | | | | | (+++) | | |
| C57BL/6 Isografts with TNF-α (10 µg) and GFP SP | | Death during TNF-α Treatment | | | | | | | |
| C57BL/6 Isografts (TNFRI⁻) with TNF-α (20 µg) and GFP | | | | | | | | | |
| C57BL/6 Isografts (TNFRII⁻) with TNF-α (20µg) and GFP | | | | | | | | | |
| (TNF Effect) | | | | | | | | | |
| NOD with TNF-α (0 µg) | (-) | (-) | (+++) | (+) | (-) | (-) | (-) | (-) | (±) |
| NOD with TNF-α (4 µg) | (-) | (-) | (-) | (±) | (-) | (+) | (-) | (-) | (+) |
| NOD with TNF-α (10 µg) | (-) | (-) | (-) | (++) | (++) | (++) | (-) | (-) | (++) |
| NOD with TNF-α (20 µg) | (-) | (-) | (-) | (-) | (++) | (++) | (-) | (-) | (-) |

FIGURE 10

|  | NOD | C57 | C57 | C57 | C57-TNF RII+ | C57-TNF RI+/- |
|---|---|---|---|---|---|---|
| 1. Normoglycemia | Islet Tx | - | Islet Tx (120 days) | Islet Tx (120 days) | | Islet Rx (120 days) |
| 2. CFA/lymphopenia | + | + | - | - | | No Lymphophenia |
| 3. TNF-α | + | + | - | + | | + |
| 4. Dose, Timing | 40 days | - | - | - | | - |
| 5. Target Injury | Spontaneous | Streptozotocin | Streptozotocin | Streptozotocin | | Streptozotocin |
| Outcome (Target Regeneration) | Regeneration | None | None | Minimal | DIE (100%) | No survival of islet Tx Moderate |

FIGURE 11

METHODS AND COMPOSITIONS FOR TREATING AUTOIMMUNE DISEASES

CROSS REFERENCE TO RELATED APPLICATIONS

This application is a continuation of U.S. patent application Ser. No. 12/632,452 (now U.S. Pat. No. 8,173,129), filed Dec. 7, 2009, which is a divisional of, and claims priority from U.S. application Ser. No. 10/358,664 (now U.S. Pat. No. 7,628,988), filed Feb. 5, 2003, which claims the benefit of the filing date of U.S. Provisional Application No. 60/392,687, filed Jun. 27, 2002, each of which is hereby incorporated by reference in its entirety.

BACKGROUND OF THE INVENTION

The invention relates to repairing and regenerating damaged tissue in a human. Such damage may result from an existing autoimmune disease, or may be the result of a non-autoimmune insult. We have previously shown that eliminating autoimmune cells and re-educating the immune system are important components of an effective treatment of an autoimmune disease (described in U.S. patent application Ser. Nos. 09/521,064, 09/768,769, and Ryu et al., *Journal of Clinical Investigations*, "Reversal of Established Autoimmune Diabetes by Restoration of Endogenous Beta Cell Function," 108:31-33, 2001), which are hereby incorporated by reference). While an autoimmune disease may be successfully treated, the individual may nonetheless have significant tissue damage as a result of the prior autoimmune attack.

Many tissues have an innate ability to repair themselves once the damage causing insult is eliminated, but this ability to repair damage decreases in correlation with the duration of the insult. For example, the regenerative capacity of endogenous pancreatic islets is virtually eliminated in long-term Type I diabetics, i.e., patients who have had the disease for more than 15 years. In cases where the endogenous tissue has lost its regenerative capacity, the damage may be repaired by providing exogenous tissue to the individual, for example, a transplant. A promising treatment for diabetes, islet transplantation, has been the subject of human clinical trials for over ten years. While there have been many successes with islet transplantation in animals, these have occurred where the animals are diabetic due to chemical treatment, rather than natural disease. The only substantiated peer reviewed studies using non-barrier and non-toxic methods and showing success with islet transplants in naturally diabetic mice use isogeneic (self) islets. The isogeneic islets were transplanted into non-obese diabetic (NOD) mice with active diabetes, which were pre-treated with TNF-alpha (tumor necrosis factor-alpha); BCG (Bacillus Clamette-Guerin, an attenuated strain of *mycobacterium bovis*); or CFA (Complete Freund's Adjuvant), which is an inducer of TNF-alpha (Rabinovitch et al., *J. Immunol.* 159:6298-6303, 1997). This approach is not clinically applicable primarily because syngeneic islets are not available. Furthermore, existing cell replacement strategies have not prevented end-stage diseases or permanently reversed insulitis. In the allograft setting of islet transplantation, grafts are eventually rejected, even with immunosuppression. Furthermore, diabetic host treatments such as body irradiation and bone marrow transplantation are unacceptably toxic, rendering the short-term alternative of insulin therapy more attractive.

Recently, islet transplantation has achieved limited success in clinical trials, such as that observed for allogenic transplants combined with multi-drug immunosuppression therapy, with type 1 diabetic patients having a sustained return to normoglycemia over a 6 month period. These results have been obtained with continuous, and sometimes toxic, drug therapy, often in the setting of a simultaneous life-saving renal transplant. However, these moderately successful islet transplants show failures after about one year, speculated to be due in part to the drug therapy itself inducing insulin resistance. The earlier failure of islet transplants in type 1 diabetics, compared to non-diabetic patients receiving islet transplants (such as in cancer patients who have had their pancreas removed), raises the concern that immunosuppressive therapy shows greater efficacy for graft rejection over autoimmunity prevention. Lending credence to these concerns is the observation of the inefficiency of immunosuppression therapy for the prevention of graft rejection of allogenic or xenogeneic islet transplants in animal studies using non-obese diabetic (NOD) mice.

We previously described a transplantation method to introduce allogeneic and xenogeneic tissues into non-immunosuppressed hosts in which the cells are modified such that the donor antigens are disguised from the host's immune system (U.S. Pat. No. 5,283,058, which is hereby incorporated by reference). Generally, masked islets or transgenic islets with ablated MHC class I molecules are only partially protected from recurrent autoimmunity in NOD mice (Markmann et al., *Transplantation* 54:1085-1089, 1992). A need exists for methods of regenerating damaged tissue that are not only applicable to tissue damage that results from autoimmune attack, but also to non-autoimmune induced damage.

SUMMARY OF THE INVENTION

The invention features methods for organ regeneration in a mammal (e.g., a human patient). Accordingly, in a first aspect, the invention features a method for increasing or maintaining the number of functional cells of a predetermined type in a mammal (i) who has injured or damaged cells of the predetermined type or who has a deficiency of cells of the predetermined type (e.g., a mammal with a lower than normal number of these cells or a mammal lacking these cells) and (ii) who does not have an autoimmune disease. This method involves administering to the mammal a composition that induces lymphopenia and that increases the number of cells of the predetermined cell type in the animal. In desirable embodiments, the composition activates a receptor on the surface of cells of the predetermined cell type or on the surface of precursor cells that differentiate into cells of the predetermined cell type in the mammal. Desirably, the method also includes administering cells of the predetermined cell type to the mammal. In desirable embodiments, the method includes administering cells that recapitulate a developmental sequence (e.g., endoderm with mesoderm; endoderm with ectoderm; or ectoderm with mesoderm to promote the regeneration of the tissue of interest). In some embodiments, the method also includes administering precursor cells that differentiate into cells of the predetermined cell type to the mammal. In particular embodiments, the method also includes inducing damage to the cells of a predetermined type in the mammal or inducing damage in a site of the mammal in which cells of the predetermined type are desirable. For example, damage can be induced in cells of the predetermined type or cells of another type within 10 inches, 5 inches, 1 inch, 10 cm, 5 cm, 1 cm, 10 mm, or 1 mm of the location in which cells of the predetermined type are desirable.

In another aspect, the invention features a method for treating or stabilizing an established autoimmune disease in a mammal. This method involves (a) administering to the mammal a first composition that selectively kills a predetermined subpopulation of blood cells, in an amount sufficient to selectively kill at least 10%, preferably at least 75%, of the subpopulation of blood cells in the mammal, (b) repeating step (a) one or more times, and (c) optionally monitoring the glucose level in the mammal two or more times. Desirably, the method also includes administering to the mammal a second composition that selectively kills a predetermined subpopulation of blood cells, in an amount sufficient to selectively kill at least 10%, preferably at least 75%, of the subpopulation of blood cells in the mammal. In some embodiments, the method includes determining whether the mammal has a subpopulation of blood cells with higher than normal sensitivity to the first composition prior to step (a).

In a related aspect, the invention features another method for treating or stabilizing an established autoimmune disease in a mammal. This method involves (a) administering to the mammal a first composition that selectively kills a predetermined subpopulation of blood cells, in an amount sufficient to selectively kill at least 10%, preferably at least 75%, of the subpopulation of blood cells in the mammal, (b) repeating step (a) one or more times, and (c) optionally maintaining the blood glucose level in the mammal within a normal range. Desirably, the method also includes administering to the mammal a second composition that selectively kills a predetermined subpopulation of blood cells, in an amount sufficient to selectively kill at least 10%, preferably at least 75%, of the subpopulation of blood cells in the mammal. In some embodiments, the method includes determining whether the mammal has a subpopulation of blood cells with higher than normal sensitivity to the first composition prior to step (a).

In another aspect, the invention features a method for treating, stabilizing, or preventing an autoimmune disease (e.g., an established autoimmune disease) and/or increasing or maintaining the number of functional cells of a predetermined type in a mammal. This method involves (a) administering to the mammal a composition that selectively kills a predetermined subpopulation of blood cells, in an amount sufficient to selectively kill at least 10%, preferably at least 75%, of the subpopulation of blood cells in the mammal, and (b) prior to, after, or concurrently with step (a), administering to the mammal cells that have the potential to differentiate into the predetermined type or that are of the predetermined cell type. In one embodiment, the method includes determining, prior to step (a), whether the blood of the mammal contains a subpopulation of blood cells with higher than normal sensitivity to the composition to be administered; if this is the case, the decision to employ the composition is reinforced.

In another aspect, the invention features a method for treating, stabilizing, or preventing an autoimmune disease (e.g., an established autoimmune disease) and/or increasing or maintaining the number of functional cells of a predetermined type in a mammal. This method involves (a) administering to the mammal a first composition that selectively kills a pre-determined subpopulation of stimulated blood cells, in an amount sufficient to selectively kill at least 10%, preferably at least 75%, of the subpopulation of stimulated blood cells in the mammal, (b) prior to, after, or concurrently with step (a), administering to the mammal a second composition that selectively kills a predetermined subpopulation of unstimulated blood cells, in an amount sufficient to selectively kill at least 10%, preferably at least 75%, of the subpopulation of unstimulated blood cells in the mammal, and (c) prior to, after, or concurrently with steps (a) or (b), administering to the mammal cells that have the potential to differentiate into the predetermined type or that are of the predetermined cell type. In one embodiment, prior to step (a), the method includes determining whether the blood of the mammal contains a subpopulation of stimulated blood cells with increased sensitivity to the first composition; if this is the case, the decision to employ the first composition is reinforced. In another embodiment, prior to step (b), the method includes determining whether the blood of the mammal contains a subpopulation of unstimulated blood cells with increased sensitivity to the second composition; if this is the case, the decision to employ the second composition is reinforced.

In another aspect, the invention features a method for treating, stabilizing, or preventing an autoimmune disease (e.g., an established autoimmune disease). This method involves administering to the mammal a composition that selectively kills a pre-determined subpopulation of unstimulated blood cells, in an amount sufficient to selectively kill at least 10%, preferably at least 75%, of the subpopulation of unstimulated blood cells in the mammal. In one embodiment, the method includes determining whether the blood of the mammal contains a subpopulation of unstimulated blood cells with increased sensitivity to the composition to be administered; if this is the case, the decision to employ the composition is reinforced.

In another aspect, the invention features a method for treating, stabilizing, or preventing an autoimmune disease (e.g., an established autoimmune disease). This method involves administering to the mammal a composition that selectively kills a pre-determined subpopulation of stimulated blood cells, in an amount sufficient to selectively kill at least 10%, preferably at least 75%, of the subpopulation of stimulated blood cells in the mammal. In one embodiment, the method includes determining whether the blood of the mammal contains a subpopulation of stimulated blood cells with increased sensitivity to the composition to be administered; if this is the case, the decision to employ the composition is reinforced.

In another aspect, the invention features a method for treating, stabilizing, or preventing an autoimmune disease (e.g., an established autoimmune disease). This method involves administering to the mammal a composition that selectively kills a pre-determined subpopulation of blood cells, in an amount sufficient to selectively kill at least 10%, preferably at least 75%, of the subpopulation of blood cells in the mammal. In one embodiment, the method includes determining whether the blood of the mammal contains a subpopulation of blood cells with increased sensitivity to the composition to be administered; if this is the case, the decision to employ the composition is reinforced.

In another aspect, the invention features a method of increasing or maintaining the number of functional cells of a predetermined type in a mammal. This method involves (a) administering to the mammal a composition that selectively kills a predetermined subpopulation of stimulated blood cells, in an amount sufficient to selectively kill at least 10%, preferably at least 75%, of the subpopulation of stimulated blood cells in the mammal, and (b) prior to, after, or concurrently with step (a), administering to the mammal cells that have the potential to differentiate into the predetermined type or that are of the predetermined cell type. In one embodiment, prior to step (a), the method includes determining whether the blood of the mammal contains a subpopulation of stimulated blood cells with increased sensitivity to the composition to be administered; if this is the case, the decision to employ the composition is reinforced. In some embodiments, the mammal has an injured or diseased organ that has increased normal functional activity after administration of the composition.

In another aspect, the invention features a method of increasing or maintaining the number of functional cells of a predetermined type in a mammal. This method involves (a) administering to the mammal a composition that selectively kills a predetermined subpopulation of stimulated blood cells, in an amount sufficient to selectively kill at least 10%, preferably at least 75%, of the subpopulation of stimulated blood cells in the mammal, and (b) prior to, after, or concurrently with step (a), administering to the mammal one or more precursor cells that differentiate into cells of the predetermined type in vivo. Desirably, the precursor cells are stem cells and step (a) is performed prior to step (b). In other embodiments, non-islet cells are administered for the treatment or prevention of diabetes. In certain embodiments, the method also involves regulating blood sugar levels in diabetic patients using, e.g., a glucose clamp or administered insulin. Desirably, a composition that kills unstimulated blood cells is administered to the patient in an amount sufficient to selectively kill a subpopulation of unstimulated blood cells in the patient.

In another aspect, the invention features a method for increasing or maintaining the number of functional cells of a predetermined type in a mammal. This method involves (a) administering to the mammal one or more cells of blood origin or endothelial origin, and (b) prior to, after, or concurrently with step (a), administering to the mammal a composition that selectively kills a predetermined subpopulation of stimulated blood cells, in an amount sufficient to selectively kill at least 10%, preferably at least 75%, of the subpopulation of stimulated blood cells in the mammal. In some embodiments, the patient has an autoimmune disease (e.g., diabetes) or an increased risk for an autoimmune disease. Desirably, a composition that kills unstimulated blood cells is administered to the patient in an amount sufficient to selectively kill a subpopulation of unstimulated blood cells in the patient.

In another aspect, the invention features a method for increasing or maintaining the number of functional cells of a predetermined type in a mammal. This method involves (a) administering to the mammal one or more cells of blood origin or of endothelial, mesoderm or ectodermic origin, and (b) prior to, after, or concurrently with step (a), administering to the mammal a composition that promotes or recapitulates the embryonic program of cellular differentiation in the host. In desirable embodiments, the method includes administering to the mammal a proteasome activity-promoting substance, such as gamma interferon. In some embodiments, the method includes administering to the mammal an agent that increases Flk or Flt expression or function. Examples include TNF-, IL-1, HAT, or NF-B induction, or cAMP inhibition, using agents known to achieve these functions. Other examples include stimulation of AP-2, EGF-1, Sp1, AP-1, NFkB, GATA stimulation with the induction of PECAM-1, activator protein-2, CT-rich Sp1 binging activity, PDGF-A, PDGF-B, monocyte chemoattractant protein-1, TF, Ets1, SCL/Tal-1, FGF, HATs P/CAF, CBP/p300 and HIF-2alpha (HRF, EPAS, HLF). These functions may also be achieved by TGF-beta inhibition, TGF-beta receptor blockade, or inhibition of CREB (camp response element binding protein). In certain embodiments, the method includes administering to the mammal an agent that increases VEGF, VEGF1, VEGF2, VEGF1R, or VEGF2R expression or function, such as a VEGF polypeptide or a nucleic acid molecule encoding a VEGF polypeptide or substance that activates the promoter of a VEGF protein receptor. VEGF polypeptides include full-length VEGF proteins, as well as biologically active VEFG fragments. These agents are in some cases preferred for mesoderm/endodermal activation for differentiation. For mural differentiation (cells usually of neural crest or pericardial origins), host treatment with PDGF or PDGF-BB can desirably be included in the method. For BV endothelium differentiation or regrowth of tissue, treatment of the host with an FGF and/or IGF-1 can be desirable. Furthermore, for promotion of regeneration can in some instances be accomplished using just one agent, or with two or more agents, administered with or without pluripotent cells.

In another aspect, the invention features a method of increasing or maintaining the number of functional cells of a predetermined type in a mammal. This method involves administering to the mammal a composition that selectively kills a predetermined subpopulation of stimulated blood cells, in an amount sufficient to selectively kill at least 10%, preferably at least 75%, of the subpopulation of stimulated blood cells in the mammal. In one embodiment the method includes determining whether the blood of the mammal contains a subpopulation of stimulated blood cells with higher than normal sensitivity to the composition to be administered; if this is the case, the decision to employ the composition is reinforced. In some embodiments, the mammal has an injured or diseased organ that increased normal functional activity after administration of the composition.

In another aspect the invention features a method of increasing or maintaining the number of functional cells of a predetermined type in a mammal with an autoimmune disease or an increased risk for an autoimmune disease. This method involves administering to the mammal one or more precursor cells that differentiate into one or more cells of the predetermined type in vivo or that promote proliferation of endogenous cells of the predetermined type in vivo. The differentiated cell(s) will eventually present MHC class I and peptide, and the MHC class I has at least one allele that matches an MHC class I allele expressed by the mammal.

In another aspect, the invention features a method of increasing or maintaining the number of functional cells of a predetermined type in a mammal. This method involves (a) administering to the mammal one or more cells of the predetermined type, and (b) prior to, after, or concurrently with step (a) administering to the mammal a composition that kills unstimulated blood cells, in an amount sufficient to selectively kill at least 10%, preferably at least 75%, of the subpopulation of unstimulated blood cells in the mammal. In one embodiment, prior to step (a), the method includes determining whether the blood of the mammal contains a subpopulation of unstimulated blood cells with higher than normal sensitivity to the composition to be administered. In some embodiments, the mammal has an injured or diseased organ that has increased normal functional activity after administration of the composition.

In another aspect, the invention features a method of increasing or maintaining the number of functional cells of a predetermined type in a mammal. This method involves administering to the mammal a composition that selectively kills a predetermined subpopulation of stimulated blood cells, in an amount sufficient to selectively kill at least 10%, preferably at least 75%, of the subpopulation of stimulated blood cells in the mammal. In one embodiment the method includes determining whether the mammal has a subpopulation of stimulated blood cells with higher than normal sensitivity to the composition to be administered. In some embodiments, the mammal has an injured or diseased organ that has increased normal functional activity after administration of the composition.

In yet another aspect, the invention features a method of increasing or maintaining the number of functional cells of a predetermined type in a mammal. This method involves (a)

administering to the mammal one or more precursor cells that differentiate into one or more cells of the predetermined type in vivo, and (b) prior to, after, or concurrently with step (a), administering to the mammal a composition that selectively kills a predetermined subpopulation of unstimulated blood cells, in an amount sufficient to selectively kill at least 10%, preferably at least 75%, of the subpopulation of unstimulated blood cells in the mammal. In one embodiment the method includes determining whether the blood of the mammal contains a subpopulation of unstimulated blood cells with higher than normal sensitivity to the composition to be administered. In some embodiments, the mammal has an injured or diseased organ that has increased normal functional activity after administration of the composition.

In still another aspect, the invention features a method for treating, stabilizing, or preventing a disease, disorder, or condition in a mammal. This method (a) administering to the mammal a first composition that selectively kills a predetermined subpopulation of blood cells, in an amount sufficient to selectively kill at least 10%, preferably 75%, of a first subpopulation of blood cells in the mammal, and (b) prior to, after, or concurrently with step (a), administering to the mammal a second composition that selectively kills a predetermined subpopulation of blood cells, in an amount sufficient to selectively kill at least 10%, preferably 75%, of a second subpopulation of blood cells in the mammal. The first subpopulation and the second subpopulation are either partially overlapping subpopulations or non-overlapping subpopulations. Desirably, first subpopulation and the second subpopulation are in different stages of differentiation. In some embodiments, the first subpopulation and the second subpopulation are in different stages of the cell cycle. In various embodiments, the first subpopulation and the second subpopulation are sensitive to different inducers of cell death. In some embodiments, the first subpopulation and the second subpopulation undergo cell death through different pathways. In particular embodiments, one subpopulation undergoes cell death through apoptosis and the other subpopulation undergoes cell death through necrosis. In some embodiments, the patient has arthritis (e.g., rheumatoid arthritis). In particular embodiments, a patient with arthritis is not administered any cells. In other embodiments, the patient is administered chondrocytes or cells that differentiate into chondrocytes. In some embodiments, the patient has injured or damaged cells of a predetermined cell type. Desirably, the method also involves administering to the patient one or more cells that have the potential to differentiate into one or more cells of the predetermined type or that are of the predetermined cell type. The cells can be administered prior to, after, or concurrently with the administration of the first and/or second compositions.

In another aspect, the invention features a method for treating, stabilizing, or preventing a disease, disorder, or condition in a mammal. This method involves (a) administering to the mammal a first composition that selectively kills a predetermined subpopulation of unstimulated blood cells, in an amount sufficient to selectively kill at least 10%, preferably at least 75%, of the subpopulation of unstimulated blood cells in the mammal, and (b) prior to, after, or concurrently with step (a), administering to the mammal a second composition that selectively kills a predetermined subpopulation of stimulated blood cells, in an amount sufficient to selectively kill at least 10%, preferably at least 75%, of the subpopulation of stimulated blood cells in the mammal. In some embodiments, the mammal has injured or damaged cells of a predetermined cell type. In certain embodiments, the method involves administering to the mammal one or more cells that have the potential to differentiate into one or more cells of the predetermined type or that are of the predetermined cell type.

In another aspect, the invention a method of increasing or maintaining the number of functional cells of a predetermined type in a human patient. This method involves inducing damage or uncovering endogenous damage (e.g., damage that promotes engraftment of transplanted cells) to the cells of a predetermined type in the patient. Endogenous damage can be measured using, e.g., blood tests, (e.g., liver function tests, tests for glucose levels, neurologic tests, or blood cell tests), visual or radiographic tests, or functional tests. A first composition that selectively kills a predetermined subpopulation of unstimulated blood cells is administered to a patient, in an amount sufficient to selectively kill at least 10%, preferably at least 75%, of the subpopulation of unstimulated blood cells in the patient. Prior to, after, or concurrently with the administration of the first composition, a second composition that kills stimulated blood cells is administered to the patient in an amount sufficient to selectively kill a subpopulation of stimulated blood cells in the patient. Prior to, after, or concurrently with the prior steps, one or more cells that have the potential to differentiate into one or more cells of the predetermined type or that are of the predetermined cell type cells are administered to the patient.

In another aspect, the invention features a method for increasing or maintaining the number of functional cells of a predetermined type, for example, pancreas cells that produce insulin, brain cells, heart cells, vascular tissue cells, cells of the bile duct, chondrocytes, or skin cells, in a human patient who has injured or damaged cells or a deficiency of cells of the predetermined type. This method includes (a) administering to the patient MHC class I and peptide (e.g., soluble MHC class I and peptide or MHC class I and peptide present on the surface of a cell); (b) prior to, after, or concurrently with step (a), administering to the patient cells that have the potential to differentiate into the predetermined type or that are of the predetermined type; and (c) prior to, after, or concurrently with step (b), inducing transient lymphopenia in the patient or in a blood sample from the patient that is re-administered to the patient. In some embodiments, steps (a) and (b) are performed concurrently by administering cells that have the capacity to present MHC class 1 and peptide and that have the potential to differentiate into the predetermined type or that are of the predetermined type.

In another aspect, the invention features another method of increasing or maintaining the number of functional cells of a predetermined type in a human patient. This method involves (a) identifying endogenous damage of or inducing damage to the cells of a predetermined type in the patient, (b) exposing the patient to MHC class I and peptide, (c) prior to, after, or concurrently with step (b), administering to the patient cells that have the potential to differentiate into the predetermined type or that are of the predetermined cell type, and (d) prior to, after, or concurrently with step (c), inducing transient lymphopenia in the patient or in a blood sample from the patient that is re-administered to the patient. In some embodiments, steps (b) and (c) are performed concurrently by administering cells that have the capacity to present MHC class I and peptide and that have the potential to differentiate into the predetermined type or that are of the predetermined type.

In desirable embodiments of any of the aspects of the invention, the methods include administering to the mammal a cell (e.g., an endothelial cell or mesenchymal cell) that promotes proliferation of the precursor cells or cells of the predetermined cell type at the site of desired regeneration, or a cell that can itself differentiate into the predetermined cell type. Desirably, the methods also include administering a cytokine, chemokine, or growth factor to the mammal. Alternatively, the methods also can include the pretreatment of mesenchymal or endothelial cell precursors with a cytokine, chemokine, or growth factor prior to their administration to the mammal. Exemplary cells of the predetermined type are islet cells that produce insulin, blood cells, spleen cells, chondrocytes, brain cells, heart cells, vascular tissue cells, cells of the bile duct, epithelial cells, endothelial cells, endoderm cells, mesoderm cells, mesenchymal cells, cells of mesenchymal origin, and skin cells. Desirable cells that differentiate into cells of the predetermined type in vivo are splenocytes, bone marrow derived cells, Hoechst 33342 positive cells, brain cells, CNS positive cells, hepatocytes, mesenchymal cells, mesodermal cells, endothelial cells, mural cells, and fetal cells. In some embodiments, the cells that differentiate into cells of the predetermined type in vivo are semi-allogeneic or isogeneic. In various embodiments, the cells that differentiate into cells of the predetermined type in vivo fail to express Fas or FasL. Desirable blood cells are T-cells, B-cells, or macrophages. Mesenchymal cells that are derived from the blood, spleen, or bone marrow and defined as Hox $11^+$, $CD90^+$, $Flk^{low}$, $CD34^+$ or $CD45^+$ are highly desirable. Other desirable cells are cells that do not, at the time they are administered, express MHC class I and peptide, but which have the capacity to do so in vivo post-transplantation, e.g., by stimulation with the appropriate antigens. In some embodiments, the MHC class I and peptide are semi-allogeneic or isogeneic. In certain embodiments, the composition is a compound that crosslinks or binds to a T-cell receptor (TCR) or other surface protein on a T-cell. In various embodiments, the composition is TNF-alpha, a TNF-alpha agonist, or a TNF-alpha inducing substance. In some embodiments, the composition binds or activates a death receptor. Exemplary TNF-alpha inducing substances include Complete Freund's Adjuvant (CFA), ISS-ODN, microbial adjuvants, such as cell wall components with LPS-like activity, cholera particles, E. coli heat labile enterotoxin, E. coli heat labile enterotoxin complexed with lecithin vesicles, ISCOMS-immune stimulating complexes, chemical adjuvants, such as polyethylene glycol and poly(N-2-(hydroxypropyl)methacrylamide), synthetic oligonucleotides containing CpG or CpA motifs, lipid A derivatives, such as monophosphoryl lipid A, MPL, muramyl dipeptide derivatives, Bacillus Clamette-Guerin (BCG), Tissue Plasminogen Activator (TPA), lipopolysaccharide (LPS), Interleukin-1 (IL-1), Interleukin-2 (IL-2), UV light, lymphotoxin, cachectin, a transcription factor-like nuclear regulator-2 (TNFR-2) agonist, a neutral blocking antibody to a B-lymphocyte stimulator (BLyS) receptor or soluble protein, an intracellular mediator of the TNF-alpha signaling pathway, a NFκB inducing substance, lymphotoxin, cachectin, IRF-1, STAT1, an agonist of an ICS-2lgAS promoter element, a lymphokine, LPS, an agonist, such as an antibody, to a TNF-superfamily receptor or soluble form of a TNF-superfamily member, a combination of TNF-alpha and an anti-TNFR-1 antibody, or a combination of TNF-alpha and a TNFR.

In desirable embodiments, the method includes administering to the mammal a proteasome activity promoting substance, such as gamma interferon. In some embodiments, the method includes administering to the mammal an agent that increases Flk or Flt expression or function. Examples include TNF-, IL-1, HAT, or NF-B induction, or cAMP inhibition. In certain embodiments, the method includes administering to the mammal an agent that increases VEGF, VEGF1, VEGF2, VEGF1R, or VEGF2R expression or function, such as a VEGF polypeptide, a nucleic acid molecule encoding a VEGF polypeptide, or a substance that activates a promoter of the VEGF receptor. In some embodiments, the method includes administering to the mammal an inhibitor of Fas or FasL expression or signaling. Desirably, the method includes maintaining the blood glucose level in the mammal within a normal range. In a particular embodiment, bone marrow cells or precursor (or pluripotent) cells (e.g., cord blood cells) are administered to hasten the healing process. These cells recapitulate the embryonic process in adult animals by hastening the critical mesoderm to endoderm interactions, endoderm and ectoderm interactions and mesoderm and ectoderm interactions, all of which are crucial for organ regeneration.

In desirable embodiments of any of the various aspects of the invention, the composition that kills naïve T-cells is MHC class I and peptide, and the MHC class I has at least one allele that matches an MHC class I allele expressed by the patient. In some embodiments, the MHC class I and peptide is soluble MHC class I and peptide or MHC class I and peptide present on the surface of a cell. In some embodiments, the administration of cells and the administration of MHC class I and peptide to kills naïve T-cells are performed concurrently by administering cells that have the capacity to present MHC class I and peptide and that have the potential to differentiate into the predetermined type or that are of the predetermined type. In some embodiments, the composition that kills pathologic T-cells (e.g., naïve T-cells) is a compound (e.g., an antibody or antibody fragment, cytokine, lymphokine, small molecule antagonist, T-cell mitogen, or co-receptor) that crosslinks a T-cell receptor (TCR) of naïve T-cells (e.g., naïve T-cells that might otherwise develop into autoimmune T-cells or pathologic cells that die if bound by an antibody or agonist). In some embodiments, the compound that kills a sub-population of naïve T-cells is not BCG or is not FAS. In other embodiments, the compound that kills a subpopulation of T-cells (e.g., naïve T-cells) is BCG, FAS, or a compound that modulates a protein kinase. An exemplary compound that selectively kills an undesired subpopulation of naïve T-cells is -CD3 antibody, a selective TCR stimulant. Examples of methods for the re-selection of naïve/unstimulated T cells include the direct killing of the disease-causing T cells, direct killing of the monocyte/macrophage antigen presenting cell with deficient MHC class I and self peptide (for example, BCG), and the re-introduction of cells correctly presenting MHC class I and self peptide fragments.

In desirable embodiments, the mammal has an autoimmune disease or an increased risk for an autoimmune disease. Exemplary autoimmune diseases include Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barré, Hashimoto's Thyroiditis, Hypothyroidism, Idiopathic Pulmonary Fibrosis, Idiopathic Thrombocytopenia Purpura (ITP), IgA Nephropathy, Insulin dependent Diabetes, Juvenile Arthritis, Lichen Planus, Lupus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Ulcerative Colitis, Uveitis, Vasculitis, Vitiligo, Wegener's Granulomatosis, and myasthenia gravis. In some embodiments, any metabolic disorder that is due to the injury or damage of the cells of a predetermined type or due to the autoimmune disease is controlled. In some embodiments, the mammal has an established autoimmune disease (e.g., the mammal has symptoms of the autoimmune disease). In some embodiments, the mammal does not have an established autoimmune disease. In particular embodiments, the mammal does not have cancer or AIDS. Desirably, the mammal is a human.

MHC class I and peptide can be administered either simultaneously (together or separately) or within 24 hours of each other. In some embodiments, two or more distinct MHC class I molecules that each contain a different allele that matches an MHC class I allele expressed by the patient are administered to the patient. In some embodiments, MHC class I and peptide are administered in an amount sufficient to induce tolerance to the donor cells or to the cells of the predetermined type. Desirably, the number of the autoimmune cells in the patient (e.g., B-cells that produce a self-reacting antibody or T-cells that are activated by presented self epitopes) decreases by at least 5, 10, 20, 30, 40, 50, 60, 80, 90, 95, or 100%.

In various embodiments of the above aspects, MHC class I and peptide are administered to the patient by administering cells that express MHC class I and peptide and that either have the potential to differentiate into the predetermined type or are of the predetermined cell type. In other embodiments, a population of living or dead (e.g., irradiated) cells that express MHC class I which has at least one allele that matches an allele expressed by the patient and which presents a peptide are administered to the patient, and another population of cells that differ from the first population of cells and have the potential to differentiate into the predetermined type or are of the predetermined cell type are administered to the patient. This latter population of cells may or may not present MHC class I and peptide, and, if expressed, the MHC class I may or may not contain one or more alleles that match that of the patient. In some embodiments, two populations of cells each with a different MHC class I that matches an allele expressed by the patient are administered.

In certain embodiments, a complex of MHC class I and peptide is formed by incubating an extracellular region of MHC class I (e.g., a soluble Fab fragment) with one or more peptides (e.g., peptides from a cell lysate or a library of random peptides, synthetic peptides, or naturally-occurring peptides). Because MHC class I binds peptides with high affinity, the soluble MHC class I fragment binds peptides in solution. In other embodiments, complexes of MHC class I and peptide are cleaved from MHC class I-expressing cells (e.g., healthy lymphocytes with at least one MHC class I allele that matches that of the patient) using, e.g., a protease. In yet other embodiments, cells that express MHC class I, which may not be complexed with peptide due to potential problems with assembly, are isolated from the patient. A fragment of the MHC class I is cleaved from the cells and incubated with one or more peptides, and the resulting complex of MHC class I and peptide is administered to the same patient from which the cells were obtained or to a different patient.

In some embodiments of any of the above aspects, lymphopenia is induced by administering to the patient an agent that is nonspecific, i.e., an agent that is toxic to lymphocytes generally, rather than targeting a particular subset of lymphocytes or lymphopenia due to new cellular distributions. Examples of such inducers of lymphopenia are TNF-alpha and substances that induce TNF-alpha, e.g., Complete Freund's Adjuvant ("CFA"), ISS-ODN, microbial adjuvants, such as cell wall components with LPS-like activity, cholera particles, E. coli heat labile enterotoxin, E. coli heat labile enterotoxin complexed with lecithin vesicles, ISCOMS-immune stimulating complexes, chemical adjuvants, such as polyethylene glycol and poly(N-2-(hydroxypropyl)methacrylamide), synthetic oligonucleotides containing CpG or CpA motifs, lipid A derivatives, such as monophosphoryl lipid A, MPL, muramyl dipeptide derivatives, Bacillus Clamette-Guerin ("BCG"), other vaccinations, Tissue Plasminogen Activator ("TPA"), lipopolysaccharide ("LPS"), Interleukin-1, Interleukin-2, UV light, lymphotoxin, cachectin, a TNFR-2 agonist, a NFκB inducing substance, lymphotoxin, cachectin, IRF-1, STAT1, an agonist of an ICS-2IgAS promoter element, or the combination of TNF-alpha and a TNFR-1 antibody. These inducers of lymphopenia can specifically kill a subpopulation of blood cells (e.g., a subpopulation of T-cells) if administering in a dose that is sufficient to specifically kill the subpopulation but not sufficient to non-specifically kill all blood cells. For example, autoimmune patients have subpopulations of blood cells with increased sensitivity to cell death: thus, low dose of these compounds are required to kill these cells. In cases in which non-specific lymphopenia is desired (e.g., such as the treatment of mammals without an autoimmune disease) larger doses can be administered. A nonspecific agent can also be an intracellular mediator of the TNF-alpha signaling pathway, e.g., NFκB, Jun N-terminal kinase ("JNK"), TRAILR2, FasL, TRADD, FADD, TRAF2, RIP, MAPK, kinase activators, a caspase, or pro-caspase. Stimulation of a signaling pathway may involve, e.g., receptors of the TNF superfamily or intracellular mediators of these pathways. Other examples of compounds that induce lymphopenia include compounds that bind or activate one or more members of the TNF receptor superfamily (e.g., TNF receptor 1 or 2, Trail-RE Trail-R2, Trail-R3, Trail-R4, OPG, Rank, Fn14, DR6, Hvem, LtbetaR, DcR3, Tramp, Fas, CD40, CD30, CD27, 4-1BB, OX40, Gitr, Ngfr, BCMA, Taxi, Baff-r, EDAR, Xedar, Troy, Relt, or CD95L). Therapeutic agents can include TNF receptor superfamily cytokine agonists or cytokine agonist antibodies. Additional compounds that directly or indirectly increase TNF-alpha can be readily identified using routine screening assays for TNF-alpha expression levels or activity. Desirably, an inducer of lymphopenia also promotes organ formation, promotes differentiation of donor cells (e.g., blood cells) into a desired cell type, and/or induces damage to host cells of a predetermined cell type to facilitate incorporation of donor cells into the desired organ. In some embodiments, transient lymphopenia is induced for a period of time sufficient to destroy at least 10, 20, 30, 40, 50, 60, 80, 90, 95, or 100% of the autoimmune cells in the patient (e.g., B-cells that produce a self-reacting antibody, T-cells that are activated by presented self epitopes, or a subset of antigen presenting cells with defective antigen presentation). In some embodiments, that agent that kills naïve T-cells is not BCG or FAS.

In some embodiments, one or more of the following TNF super family ligands are administered to the mammal or are upregulated by administration of another compound to the mammal: Trail(Apo2L), RANKL, TWEAK, TNF, LT, LIGHT, LT, TL1A, FASL, CD40L, CD30L, CD27L, CD27L, 4-1BBL(CD137L), OX40L(CD134L), GITRL, APRIL, BAFF, EDA1, or EDA2. In certain embodiments, one or more of the following TNFα superfamily receptors are activated by administration of a compound to the mammal: TRAIL-R1 (DR4), TRAIL-R2(DR5), TRAIL-R3(DCR1), TRAIL-R4 (DCR2), OPG, RANK, RN14, DR6, THF-R2(CD120B), TNF-R1(CD120A), FVEM, LIBETAR, DCR3, TRAMP (DR3), FAS(CD95), CD40, CD30, CD27, 4-1BB(CD137), CD134(OX40), GITR, NGFR, BCMA, TACI, BAFFR, EDAR, XEDAR, TROY, or RELT. Desirably, one or more of the following members of death cascades are activated: FASL (CD95L:CD178) with FAS (CD95), TRAIL (APO-2L) with TRAIL-R1(DR4), TRAIL(APO2L) with TRAIL R2(DR5), or TNF with TNFR1.

Desirably, one or more of the following are administered to the mammal: IL-1, IL-2, IL-4, IL-5, IL-6, IL-7, IL-10, IL-11, IL-12, IL-13, IL-18, INF-alpha, IFN-beta, IFN-gamma, TFG-beta, PDGF, and/or VEGF. A small molecule or antibody agonist of TLR1, TLR2, TLR6, TLR3, TLR4, TLR5, TLR7, and/or TLR9 is desirably administered. Exemplary TNF superfamily members and their receptor agonists include TRAIL-R1, TRAIL-R2, TRAIL-R3, TRAIL-R4, OPG, RANK, Fn14, DR6, TNF-R2, TNF-R1, HVEM, LtbetaR, DcR3, TRAMP, Fas, CD30, CD27, 4-1BB, OX40, GITR, NGFR, BCMA, TACI, EDAR, XEDAR, Troy, and RELT. Biologics of diverse compositions such as BCG, BLP, fibronectin Domain A, lipoarabinomannan, LPS binding protein, LPS, lipoteichoic acid, macrophage stimulatory lipopeptide 2, manosylated phosphatidylinositol peptidoglycan, respiratory syncytial virus protein F, and soluble tuberculosis factor may also be administered, if desired.

Any of a wide variety of cells can be administered to the patient according to the invention. The cells can be cells that, compared to the desired functional cells, are relatively undifferentiated; i.e., they can be stem cells derived, e.g., from embryonic or fetal tissue, from adult stem cell sources, from adult tissues harboring a subset of pluripotent cells, or from cord blood. Alternatively, the administered cells can be relatively more differentiated cells, e.g., cells that stain positively for the stain Hoechst 33342 which stains the nucleus of immature hematopoietic cells; brain-derived cells; cells derived from non-brain CNS tissue (e.g., spinal cord); hepatocytes; chondrocytes; splenocytes; bone marrow-derived cells; cells of blood or lymphoid origin; or parenchymal cells. In certain embodiments, the administered cells are not islets, not beta cells, or not insulin-producing beta cells. In various embodiments, cells other than the predetermined cell type are administered to the patient and form the predetermined cell type in vivo. For example, in some embodiments, cells other than islets are administered to the patient and form insulin-producing islets in vivo. Desirably, the cells are administered to the same human from which they were obtained or to another human. It is also contemplated that donor cells from other mammals can be used. Exemplary donor mammalian cells are from pigs or primates such as monkeys.

In some embodiments, patients (e.g., patients without an autoimmune disease) are administered cells that have been genetically engineered (e.g. by elimination of genes encoding cell death proteins such as Fas, FasL, or caspases), chemically pre-treated, or biologically pre-treated (e.g., treated with an antibody or antibody fragment reactive with Fas or FasL) to exhibit reduced resistance to spontaneous cell death. In certain embodiments, a compound that decreases the expression level or activity of Fas or FasL is administered to the donor cells or to the host. In some embodiments, the cells are allogeneic, semi-allogeneic, or isogeneic. Exemplary MHC class I-expressing cells that can be used in the invention include monocytes, macrophages, dendritic cells, B-cells, Langerhans cells, epithelial cells, mesenchymal cells, and parenchymal cells. Other cells express MHC class I at lower levels and can also be used in the present methods. Desirably, at least 20, 40, 60, 80, 90, 95, or 100% of the administered cells express MHC class I complexed with peptide. In some embodiments, cells present MHC class 1 and peptide before and after they are administered to the patient. In other embodiments, cells present MHC class 1 and peptide only after they are administered to the patient. In some cases, the cells differentiate in vivo into cells that present MHC class 1 and peptide.

In some embodiments, one or more death receptors (e.g., the death receptors listed in FIG. 5) are inactivated on the donor cells or one or more intracellular signaling proteins that mediate cell death are inactivated in the donor cell to prevent death of the transplanted cells. For example, FLIP can be used to down regulate Fas/FasL expression. In other embodiments, extracellular inhibition or reduction in IL2 (e.g., inhibition due to chemicals or antibodies) is used to upregulate FLIP which then down regulates FAS. In other embodiments, the donor cells have a blockage of IL2R, such as the binding of a chemical (e.g., a non-lytic antibody fragment) to IL2R to inhibit binding of IL2 to IL2R and thus IL2-mediated upregulation of FAS. In other embodiments, one or more members of the intracellular pathway for FAS activation are inhibited in the donor cells prior to transfer. Examples include the inhibition of the translation of transcription factors such as cFOS, cJAN, PKC, Lck, Zap70, MAPK, Itk (IL-2 inducible T cell kinase) and JNK. In particular embodiments, the transcription or translation of transcription factors is transiently inhibited with antisense oligonucleotides or by RNA interference (RNAi).

The number of functional cells maintained according to the invention can be increased by further treating the patient with a substance that increases proteasome activity; this treatment can specifically increase the immuno-proteasome subunits LMP2, LMP7, and LMP10, rendering the cells or host more responsive to the growth promoting activities of VEGF pathways or NF B pathways, which are important for cellular regeneration. Administration of the proteasome-enhancing substance can be carried out at any time during the method of the invention; e.g., prior to or following the administration of the cells and/or MHC class I and peptide; or prior to or following induction of transient lymphopenia. The proteasome activity-increasing substance can be, e.g., gamma interferon; VEGF or a substance that increases VEGF level or activity, such as a nucleic acid molecule encoding VEGF or an active fragment thereof; fetal liver kinase-1/kinase domain region (Flk-1/KDR) or a substance that increases Flk level or activity; or fms-like tyrosine kinase-1 (Flt-1) or a substance that increases Flt level or activity. Additional proteasome activity-increasing substances include compounds that inhibit the expression or signaling of Fas or FasL (e.g., an anti-Fas or anti-FasL antibody) and/or promote the viability of endogenous or exogenously administered pluripotent cells.

Desirably, the number of cells of the desired cell type that are present at least one day, one week, one month, or one year after treatment using the methods of the invention increases by at least 20, 30, 50, 75, 100, 200, 500, or even 1000% relative to the number of cells of that cell type that are present in the patient before treatment or the number of cells present in a control subject (e.g., a subject who received a vehicle control or a placebo). In some embodiments, the number of cells of the desired cell type in a treated patient is at least 50, 60, 70, 80, 90, or 100% of the amount of the corresponding cells in a healthy patient without a deficiency in those cells. In certain embodiments, cells of donor origin are present in the patient at least one day, one week, one month, or one year after treatment. For example, diabetic patients that are treated using the present methods desirably contain cells of donor origin in their pancreas after treatment.

In some embodiments, the methods of the invention are used to treat damage or deficiency of cells in an organ, muscle, or other body structure or to form an organ, muscle, or other body structure. Desirable organs include the bladder, brain, nervous system tissue, blood vessels, skin, eye structures, gut, bone, muscle, ligament, esophagus, fallopian tube, heart, pancreas, intestines, gallbladder, kidney, liver, lung, ovaries, prostate, spinal cord, spleen, stomach, testes, thymus, thyroid, trachea, ureter, stomach, urethra, and uterus. For these applications, donor differentiated cells, such as cells from any of these organs, or undifferentiated cells, such as embryonic or adult stem cells, are administered to a patient. In a desirable embodiment, a pancreas is regenerated, or the organelle representing the islets of Langerhans reappears. In some embodiments, the organ, muscle, or other body structure that is repaired or replaced was damaged, at least in part, due to the aging process. In some embodiments, at least 20, 40, 60, 80, 90, 95, or 100% of the cells of the regenerated organ (e.g., the bile ducts, endocrine portions of the pancreas, or the entire pancreas), muscle, or other body structure are of donor origin. In certain embodiments, the precursor cells are provided in a female by pregnancy.

The methods of the invention can be used to treat, prevent, or stabilize autoimmune diseases and diseases or conditions other than autoimmune diseases, such as diseases or injuries associated with damage to a particular class of cells. For example, these method may be used to treat, prevent, or stabilize autoimmune diseases including, but not limited to, Insulin dependent Diabetes, lupus, Sjogren's disease, rheumatoid arthritis, pemphigus vulgaris, multiple sclerosis, hypothyroidism, graves disease, psoriasis, premature ovarian failure (POF), and myasthenia gravis. Other examples of autoimmune diseases are described herein. In these procedures, the cells that are attacked by the recipient's own immune system may be replaced by transplanted cells that either are the desired cell type or that differentiate into the desired cell type in vivo. For the treatment of type I or type II diabetes, insulin-producing islet cells (e.g., islet cells expressing MHC class I that has at least one allele that matches the patient and that presents a peptide) or cells that differentiate into insulin-producing islet cells in vivo (e.g., cells originating from splenocytes, bone marrow origin cells, blood origin cells, or fibroblasts) can be transplanted into the patient. Desirably, the patient's glucose level decreases to less than 200 mg/dl, 150 mg/dl, or 120 mg/dl (in order of increasing preference).

Examples of other medical applications for these methods include the administration of neuronal cells or cells that differentiate into neuronal cells to an appropriate area in the human nervous system to treat, prevent, or stabilize a neurological disease such as Alzheimer's disease, Parkinson's disease, Huntington's disease, or ALS; or a spinal cord injury. For example, degenerating or injured neuronal cells may be replaced by transplanted cells. Undifferentiated donor cells may be administered, e.g., systemically or locally.

In preferred embodiments for the treatment of conditions other than autoimmune conditions, a compound that inhibits the destruction of stem cells by an administered inducer of lymphopenia (e.g., TNF-alpha) is desirably administered to the patient. Examples of such compounds include anti-Fas antibodies. In some embodiments, stem cells or cells that form stem cells in vivo are administered to the patient after the administration of the inducer of lymphopenia or lymphoid redistribution (e.g., after the destruction of endogenous autoimmune cells, such as after 7-14 days of lymphopenia).

With respect to the therapeutic methods of the invention, it is not intended that the administration of one or more compounds (e.g., purified or unpurified donor cells, MHC class I and peptide, and an inducer of lymphopenia) to a patient be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to increase the number of desired cells. The compound(s) may be administered to the patient in a single dose or multiple doses. When multiple doses are administered, the doses may be separated from one another by, for example, one day, one week, one month, or one year. For example, a compound that induces lymphopenia may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of donor cells can be increased if more cells of a particular cell type are needed, e.g., if the glucose levels of a diabetic patient have not returned to normal or if an ongoing process decreases the number or activity of cells of the predetermined cell type. The dosage of a compound that induces lymphopenia can also be increased if autoimmune cells remain in the patient, for example, if a blood sample from the patient contains autoantibodies or contains cells with increased sensitivity to TNF-alpha, indicating that autoimmune cells are still present in the patient. Conversely, the dosage of donor cells or lymphopenia-inducing compounds can be decreased if a desired number of cells are present in the patient or if autoimmune cells are no longer present. If desired, conventional treatments may be used in combination with the therapies of the present invention. For example, diet and exercise can be used to facilitate the control of glucose levels in diabetic patients.

Other embodiments of the present methods are disclosed in U.S. patent application Ser. No. 09/521,064, filed Mar. 8, 2000, and 09/768,769, filed Jan. 23, 2001, and PCT publication WO00/53209, published Sep. 14, 2000, which are incorporated by reference).

DEFINITIONS

By "treating, stabilizing, or preventing a disease, disorder, or condition" is meant preventing or delaying an initial or subsequent occurrence of a disease, disorder, or condition; increasing the disease-free survival time between the disappearance of a condition and its reoccurrence; stabilizing or reducing an adverse symptom associated with a condition; reducing the severity of a disease symptom; slowing the rate of the progression of a disease; or inhibiting or stabilizing the progression of a condition. Desirably, at least 10, 20, 30, 40, 60, 80, 90, or 95% of the treated subjects have a complete remission in which all evidence of the disease disappears. In another preferred embodiment, the length of time a patient remains free of disease symptoms after being diagnosed with a condition and treated with a therapy of the invention is at least 10, 20, 40, 60, 80, 100, 200, or even 500% greater than (i) the average amount of time an untreated patient remains free of disease symptoms or (ii) the average amount of time a patient treated with another therapy remains free of disease symptoms. Desirably, the number of disease-causing white blood cells decreases by at least 10, 20, 30, 40, 60, 80, 95, or 100%.

By "autoimmune disease" is meant a disease in which an immune system response is generated against self epitopes.

Some examples of autoimmune diseases include Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barré, Hashimoto's Thyroiditis, Hypothyroidism, Idiopathic Pulmonary Fibrosis, Idiopathic Thrombocytopenia Purpura (ITP), IgA Nephropathy, Insulin dependent Diabetes, Juvenile Arthritis, Lichen Planus, Lupus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Ulcerative Colitis, Uveitis, Vasculitis, Vitiligo, Wegener's Granulomatosis, and myasthenia gravis.

"MHC class I and peptide" is commonly understood to refer to the MHC/peptide complex as it is naturally presented on the surface of a cell in connection with the normal functioning of the immune system. Cytoplasmic antigens are processed into peptides by cytoplasmic proteases and the proteasome, a multicatalytic proteinase complex associated with the Lmp2, Lmp7, and Lmp10 protein. As used herein, the term "MHC class I and peptide" includes such naturally occurring complexes, and in addition includes peptides that differ from native antigen-derived peptides but which are nonetheless able to form a complex with class I that is effective to maintain functional cells according to the invention. Exemplary peptides that differ from native antigen-derived peptides may contain unnatural amino acids, e.g., D-amino acids, as well as naturally-occurring amino acids. Preferred MHC class I and peptide complexes are those in which a chain of amino acids between 8 and 10 residues in length is correctly complexed with an MHC class I molecule that is either semi-allogeneic, i.e., at least one MHC class I allele is mismatched and at least one MHC class I allele is matched between donor and recipient, or syngeneic, i.e., all MHC class I alleles are matched between donor and recipient, where the MHC class I and peptide complex contributes to the re-education or re-selection of the immune system.

In some embodiments, the MHC class I and peptide are present on the surface of cells that are administered to the patient. Other MHC class I/peptide complexes are soluble complexes that are not expressed on the surface of a cell. In particular embodiments, the extracellular region of MHC class I (e.g., a Fab fragment of MHC class I) or soluble, full-length MHC class I is incubated with one or more peptides according to known methods under conditions that allow a peptide to bind the MHC class I fragment, and the resulting MHC class I and peptide complex is administered to the patient. In other embodiments, a mixture of MHC class I and peptide are administered to the patient, and the MHC class I and peptide bind in vivo after administration to the patient. In some embodiments, the administered MHC class I has 1, 2, 3, or 4 alleles with at least 60, 70, 80, 90, 95, or 100% sequence identity to that MHC class I expressed by the patient. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

By "functional cell," is meant cells that carry out their normal in vivo activity. In certain desirable embodiments of the invention, the cells are capable of expressing endogenous self-peptide in the context of MHC class I.

By "predetermined type," when used in reference to functional cells, is meant a defined cell type. For example, one skilled in the art may decide to carry out the method of the present invention in order to increase or maintain the number of functional islet cells in the pancreas. In this example, the cells of a predetermined type are islet cells or islet precursor cells.

Standard assays can be used to determine whether administered cells form cells of the predetermined cell type in vivo. For example, cells may be analyzed for expression of particular proteins (e.g., proteins specific for the predetermined cell type) using standard Western or immunofluorescence analysis or for the expression of particular mRNA molecules (e.g., mRNA molecules specific for the predetermined cell type) using a cDNA array (Ausubel et al., supra). Examples of other characteristics of the administered cells that may be analyzed to determine whether they have been converted into the desired cell type include the size of the cell, cell morphology, volume of cytoplasm, and cell function (e.g., production of insulin or other hormones).

By "semi-allogeneic," is meant a match of at least one marker, for example, an MHC class allele, between cells of the same type from different individuals of the same species. Desirably at least two or three MHC class I alleles match between the donor and the host. Standard methods may be used to determine whether an MHC class I allele expressed by a donor cell matches an MHC class I allele expressed by the recipient. For example, antibodies specific for a particular MHC class I allele can be used to determine what alleles are expressed. Alternatively, PCR amplification of nucleic acids encoding MHC class I alleles can be used.

By "syngeneic donor cell" or "isogeneic donor cell," is meant (i) a donor cell that is genetically identical, or matched at the HLA region (i.e., has at least four, and preferably all 6, of the standard markers in common with), to a cell of the recipient or (ii) a donor cell that is re-administered to the same patient from which it was obtained.

A "TNF-alpha inducing agent," is desirably a compound that results in the expression of endogenous TNF-alpha, enhances secretion of TNF-alpha, or enhances bioavailability or stability of TNF-alpha. However, TNF-alpha agonists, agents that stimulate TNF-alpha signaling or enhance post-receptor TNF-alpha action, or agents that act on pathways that cause accelerated cell death of autoimmune cells, are also included in this definition. Stimulation of TNF-alpha induction (e.g., by administration of CFA) is desirably carried out prior to, after, or during administration (via implantation or injection) of cells in vivo.

By "lymphopenia" is meant a decrease in the total number of lymphocytes in a blood sample from a mammal. In some embodiments, this decrease is due to death of lymphocytes, such as T-cells, B-cells, and/or macrophages. In certain embodiments, this decrease is due to redistribution of lymphocytes.

By "nonspecific," in reference to lymphopenia, is meant a reduction in the total number of lymphocytes in an individual, and is not limited to a subset of lymphocytes.

By "selectively killing blood cells" is meant directly or indirectly reducing the number or relative percentage of a subpopulation of blood cells (e.g., autoreactive lymphoid cells such as T- or B cells or the defective antigen presenting cells) such as a subpopulation of unstimulated cells or stimulated cells. In desirable embodiments, the subpopulation is a subset of T-cells, B-cells, or macrophages. Desirably, the killed memory T-cells are autoimmune T-cells, i.e., T-cells that are activated by presented self epitopes. In desirable embodiments, the killed naïve T-cells are cells that would otherwise become autoimmune T-cells. Desirably, the number of autoimmune T-cells or cells that would otherwise become autoimmune T-cells decreases by at least 25, 50, 100, 200, or 500% more the number of healthy non-autoimmune T-cells decreases. In some embodiments, the number of autoimmune T-cells or cells that would otherwise become autoimmune T-cells decreases by at least 25, 50, 75, 80, 90, 95, or 100%, as measured using standard methods. The T-cells can be killed due to any pathway, such as apoptosis, necrosis, and/or activation induced cell death. Apoptosis can be assayed by detecting caspase-dependent cell shrinkage, condensation of nuclei, or intranuclear degradation of DNA. Necrosis can be recognized by caspase-independent cell swelling, cellular degradation, or release of cytoplasmic material. Necrosis results in late mitochondrial damage but not cytochrome C release. In some embodiments, memory T-cell are killed by apoptosis, and naïve T-cells are killed by necrosis. For the treatment of lupus, B-cells are desirably killed or, alternatively, they are allowed to developmentally mature.

By "stimulated blood cell" is meant a blood cell (e.g., a memory T-cell, a B-cell, or a macrophage) that has been exposed to an antigen.

By "unstimulated blood cell" is meant a blood cell (e.g., a naïve T-cell, a B-cell, or a macrophage) that has not been exposed to an antigen.

By "pathologic T cell" is meant a T cell that is involved, or has the potential to be involved, in an autoimmune response or disorder.

Stimulated cells tend to be in later stages of maturation than unstimulated cells, in active progression through the cell-cycle, and/or involved in infiltrating a diseased or damaged organ or tissue. Unstimulated cells tend to progress through the cell-cycle more slowly or not at all. Memory T-cells tend to express a higher density of IL-2 receptor (e.g., 10-20% higher density) than naïve T-cells. Naïve T-cells tend to express a higher density (e.g., a 5-20% higher density) of $CD45RB^{high}$, CD95, and/or CD62L than memory T-cells.

By "purified" is meant separated from other components that naturally accompany it. Typically, a factor (e.g., a protein, small molecule, or cell) is substantially pure when it is at least 50%, by weight, free from proteins, antibodies, and naturally-occurring organic molecules with which it is naturally associated. Desirably, the factor is at least 75%, more desirably, at least 90%, and most desirably, at least 99%, by weight, pure. A substantially pure factor may be obtained by chemical synthesis, separation of the factor from natural sources, or production of the factor in a recombinant host cell that does not naturally produce the factor. Proteins, vesicles, chromosomes, nuclei, other organelles, and cells may be purified by one skilled in the art using standard techniques such as those described by Ausubel et al. (Current Protocols in Molecular Biology, John Wiley & Sons, New York, 2000). The factor is desirably at least 2, 5, or 10 times as pure as the starting material, as measured using polyacrylamide gel electrophoresis, column chromatography, optical density, HPLC analysis, or western analysis (Ausubel et al., supra). Preferred methods of purification include immunoprecipitation, column chromatography such as immunoaffinity chromatography, magnetic bead immunoaffinity purification, and panning with a plate-bound antibody.

BRIEF DESCRIPTION OF THE DRAWINGS

The application file contains drawings executed in color (FIG. 1). Copies of this patent or patent application with color drawings will be provided by the Office upon request and payment of the necessary fee.

FIG. 4 is a table demonstrating the ability of multiple doses of TNF-alpha to inhibit insulitis in 20 to 35 week old, diabetic mice.

FIG. 5 is a list of exemplary death receptors.

FIG. 6 is list of exemplary inhibitors of cell death that can be used to prevent death of transplanted donor cells or of endogenous healthy cells (Oncogene Research Products, 2002/2003 catalogue, San Diego, Calif.). An exemplary inhibitor of necrosis is geldanomycin, and an exemplary inhibitor of apoptosis is zVAD-fmk.

FIG. 7 is a list of standard kits that can be used to measure the level of cell death (Oncogene Research Products, 2002/2003 catalogue, San Diego, Calif.).

FIG. 8 is list of exemplary compounds that induce cell death (Oncogene Research Products, 2002/2003 catalogue, San Diego, Calif.).

FIG. 9 is a table that summarizes the analysis of splenocytes or PBLs from mice injected biweekly for 40 days with $10^7$ donor cells. Fewer cells may also be used in each injection in the present methods, especially if the cells are administered more often and/or for longer. Column "Whole GFP+%" lists the percentage of splenocytes or PBL cells that are fluorescent, indicating they are of donor origin. Column "H-2 kb+GFP+" lists the percentage of analyzed cells that are fluorescent and that express the same class 1 locus as the donor cells. Column "CD3+ + GFP+" lists the percentage of analyzed cells that are fluorescent and express CD3, which is only expressed on T-cells. Column "B220+ GFP+" lists the percentage of analyzed cells that are fluorescent and express B220, which is only expressed on B-cells. Column "Mac-1+ GFP+" lists the percentage of analyzed cells that are fluorescent and express Mac-1, which is only expressed on macrophages.

FIG. 10 is a table that summarizes characteristics of mice treated with various methods of the present invention. "TNF-α low dose" refers to a 2 µg dose of TNFα. "Sp" denotes splenocytes, and "Bm" denotes bone marrow donor cells. "(−)" indicates no significant difference compared to untreated control mice, "(+)," "(++)," and "(+++)" denote increasing differences (e.g., increased activity or increased number of cells) compared to untreated control mice.

FIG. 11 is a table summarizing conditions that promote regeneration.

DETAILED DESCRIPTION

Figure 1:
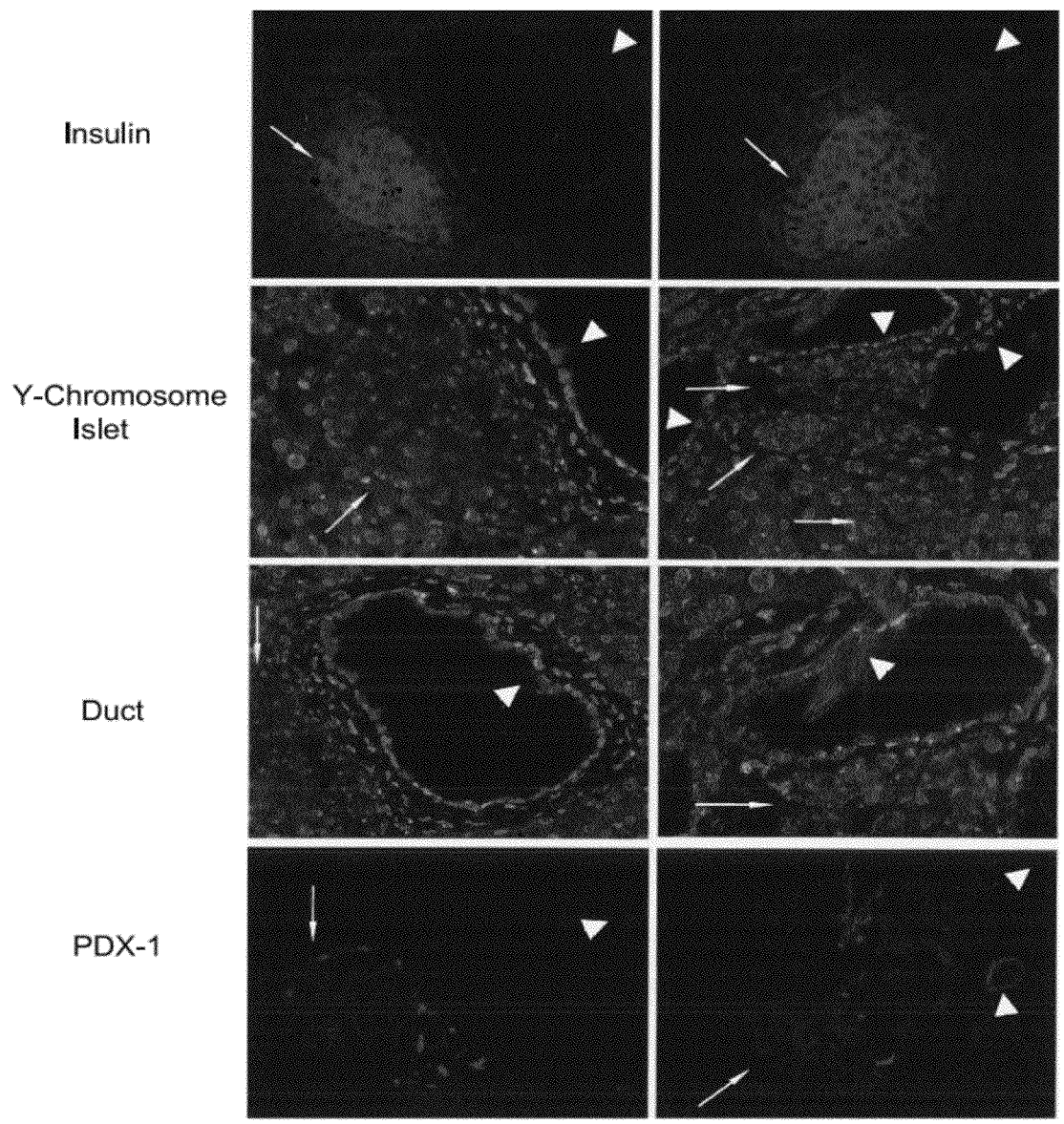
FIG. 1 is a table that demonstrates the presence of Y-chromosome positive cells in adult female NOD mouse pancreatic islets with disease reversal. Column 1 and column 2 represent two different female NOD mice with long term correction of their disease defined as the reversal of hyperglycemia followed by regeneration of the insulin-secreting cells in the pancreas. All histology sections from each animal were stained by immunohistochemistry and were from consecutively cut specimens. The first row shows the stain of the pancreas with insulin antibodies, demonstrating the reappearance of beautiful islets free of disease. The second row demonstrates that Y-chromosome staining of the same islet produces punctuate dark pink staining of the Y chromosome only within the islet tissue and associated duct tissue, but not within the associated exocrine portions of the pancreas. This result is definitive evidence that the origin of the reappearing islets is the male donor splenocytes. Row 3 is a close-up picture of the associated duct that also shows that the Y cells were not only present in the islet but also populate the duct tissue. The duct was repopulated by the donor cells and is less uniform than the islet repopulation. In general, almost all the islet tissue in the pancreases of these mice was of donor origin, as demonstrated by the uniform Y chromosome presence in all cells. The ducts in the pancreases of these animals may be of completely female origin or of a mixed origin composed of both female and male cells. Row 4 demonstrates that a developmental marker of early islet regeneration is PDX-1. The staining of the pancreatic sections reveals bright PDX-1 staining, exclusively in the regenerating islet but not in the associated exocrine portions of the pancreas.

We have succeeded in regenerating a functioning organ (the islet cells of a pancreas) in an animal with a damaged pancreas, and have shown that almost all of the visible portions of the organ, as well as a large portion of the bile ducts, are of donor origin.

The present methods for increasing the number of functional cells of a predetermined cell type in a patient have a number of advantages. For example, the present methods are robust and durable. The methods can be used to replace most or all of an endogenous organ using donor cells of the same cell type or of a different cell type as the organ. The methods can also be performed without immunosuppression for nonspecific inactivation or death of autoimmune cells.

These following examples are provided for the purpose of illustrating the invention and should not be construed as limiting.

Materials and Methods

Diagnosis and Treatment of Mice

Female NOD mice were obtained from either Taconic Farms (Germantown, N.Y.) or Jackson Laboratory (Bar Harbor, Me.). C57BL/6J mice were obtained from The Jackson Laboratory. All mice were maintained under pathogen free conditions.

NOD mice were screened for the onset of diabetes by monitoring their body weight and blood sugar level. The criteria for diagnosis of diabetes included two consecutive blood sugar concentrations exceeding 400 mg/dl. Mice with blood sugar levels greater than 400 mg/dl were given daily injections of 1.0 to 1.5 units of Neutral Protamine Hagedorn (NPH) human insulin for each 100 grams of body weight to prevent immediate death due to hyperglycemia. The use of such severely diabetic mice relatively late after disease onset ensures that the endogenous pancreas islets were completely obliterated prior to transplantation of the donor islet cells.

Splenocyte donors included normal C57 mice, C57 $\beta_2 M^{-/-}$ mice whose cells have a decreased ability to express MHC class I and peptide on their surface due to the ablation of the chaperone protein $\beta_2$ microglobulin but can express MHC class I and self peptide when exposed to normal mouse serum, C57 $\beta_2 M^{-/-}$ TAP1$^{-/-}$ mice which have a decreased ability to re-express MHC class I and self peptide, and MHC class II$^{-/-}$ mice in which the I-A gene is disrupted and the E locus for MHC class II is not expressed because of endogenous defects in the C57 strain. Splenocytes, generally at a dose of $9 \times 10^6$ cells, were injected into some NOD recipients through the tail vein twice a week. TNF-alpha, which is commercially available from a variety of vendors including Genentech (South San Francisco, Calif.), Hoffman-LaRoche (Basel, Switzerland), Boehringer Ingelheim (Germany), Asahi Chemical Industry (Japan), and Sigma-Aldrich (St. Louis, Mo.), was administered intraperitoneally (1-20 µg per dose, 2 to 3 times per week) to eliminate autoreactive cells and promote regeneration in the host by recapitulating the embryonic program of blood vessel endothelium, i.e. induction of NF-B and/or VEGF. CFA (Difco Laboratory, Detroit, Mich.) was mixed with an equal volume of physiological saline, and approximately 1-50 µl were injected into each hind-footpad at the time of the islet transplantation or after the first splenocyte injection.

Islet Transplantation

Islets were isolated from donor C57 mice or 6 to 8 week-old pre-diabetic female NOD mice and served as a glucose clamp and the source of MHC class I and self-peptide. Gradient centrifugation followed by manual selection of islets was performed to ensure that both preparations were highly enriched for islets and to accurately determine the number of transplanted islets. Approximately 500 to 600 specially selected islets were grafted beneath the left kidney capsule of each diabetic NOD recipient. For islet encapsulation, 900-1100 islets were enclosed in 0.2-0.5 cm diameter alginate spheres that were surgically inserted into the peritoneal cavity of diabetic NOD mice. Transplantation was considered successful if the non-fasting blood glucose concentration returned to normal within 24 hours after surgery. The glucose concentration of the recipient's blood was monitored three times a week after transplantation with a Glucometer Elite instrument (Bayer Corp., Pittsburgh, Pa.). Allografts were considered to have been rejected if the blood glucose concentration increased to more than 250 mg/dl at two monitoring time points. The recipients that rejected allografts were tagged for histological examination and flow-cytometric studies.

To determine the effect of the endogenous pancreatic islets in the control of blood sugar concentration, the subrenal islet transplants were surgically removed and analyzed. Similarly, islets that had been encapsulated in alginate spheres were removed, as necessary, from the peritoneal cavity after direct localization using a dissecting microscope. Histological analyses of the pancreata and allograft were performed by (i) staining with hematoxylin and eosin for evaluation of lymphoid infiltrates and (ii) staining with aldehyde-fuchsin for insulin islet content. The entire pancreas from splenic to duodenal stomach attachments was removed, fixed, and subjected to serial sectioning, usually at 10 µm per section.

Example 1

CFA Treatment and Islet Transplantation in NOD Mice

Hosts for the transplantation experiments were severely diabetic female NOD mice, usually greater than 20 weeks of age, which exhibited blood glucose concentrations of greater than 400 mg/dl for at least seven days and had been treated by daily administration of insulin for that length of time. Islet transplants were placed unilaterally in the kidney capsule to facilitate non-lethal removal and histological examination. Islets from 6-8 week-old pre-diabetic donor females or from normal C57 donor mice were rapidly rejected by diabetic NOD hosts in all cases, usually by day 9. Although C57 donor islets with transient ablation of class I survive indefinitely in non-immunosuppressed diabetic and non-autoimmune diabetic hosts, the survival time for $\beta_2M^{-/-}$ C57 islets in diabetic NOD females is only about two to three times that of normal C57 islets. This observation confirms that the ablation of the donor cells is related to the current disease, and not related to allograft rejection. CFA treatment prolonged survival of syngeneic islet grafts in diabetic NOD hosts, but had a minimal effect on the survival of C57BL/6 islets, which were uniformally rejected about 11 days after transplantation. However, the combination of $\beta_2M$ C57 islet transplants with CFA treatment resulted in sustained normoglycemia for more than 120 days in 5 out of 14 diabetic hosts. Although the duration of hyperglycemia before initiation of the therapy varied between 7 and 20 days in these cohorts, the length of this interval was not statistically related to the duration of sustained normoglycemia after treatment. The animals in this study with sustained normoglycemia also had progressive weight gain similar to that in NOD female host cohorts that never became diabetic. The normalization of blood sugar concentration is a measure of treatment success.

After the recurrence of hyperglycemia in NOD mice that had been treated with CFA and syngeneic NOD transplants that do not have MHC class I-presented self-peptide, the kidney containing the allograft was examined histologically. Macrophage and T-cell specific infiltrates were apparent under the kidney capsule at the site of transplantation, a characteristic of recurring autoimmune disease. Moreover, no intact islets were detected in the pancreas. Although an occasional host had islet remnants in the pancreas, these were largely obscured by dense pockets of infiltrating lymphocytes. This recurrence of hyperglycemia after administration of NOD transplants may be due to the inability of the MHC class I in the NOD transplants to present peptide because of an error in this pathway in NOD mice. This lack of peptide presented by MHC class I cells may prevent the transplanted cells from inducing tolerance. Alternatively, even if NOD islets present MHC class I and peptide, it is possible that a single exposure of a parenchymal cell is insufficient. Thus, the host NOD mice generate autoimmune T-cells that destroy the transplanted cells.

Similar histological characteristics, including infiltrating lymphocytes at both the transplant site and in the pancreas, were apparent in diabetic NOD mice that received CFA in combination with semi-allografts from C57 donors. Unexpectedly, for all NOD mice with long-term normoglycemia, after removing the $\beta_2M^{-/-}$ C57 islets, and after CFA treatment, no surviving allografts were detected under the kidney capsule when the animals were examined more than 129 days after transplantation using this protocol. In contrast, the pancreas in each of these five recipients exhibited well-formed islets that appeared completely granulated when stained with aldehyde-fuchsin. Our results show that the islets were free of lymphocytes, with lymphocytes only present around the circumference of the islets. This pattern of lymphocyte accumulation, with lymphocytes surrounding, but not invading the islets has been associated with non-progressing or interrupted beta cell autoimmunity. The return to normoglycemia in the absence of detectable transplanted islet tissues, together with the presence of islets in the pancreas largely devoid of infiltrating lymphocytes indicates not only that autoimmunity has been interrupted, but also that the function of the endogenous beta cells had been restored. This disruption of autoimmunity is thought to be due, at least in part, to the induction of TNF-alpha by the administered CFA, and the destruction of autoimmune T-cells by the resulting TNF-alpha. Additionally, the expression of MHC class I with an allele that matches the host and peptide by the donor cells induces tolerance by T-cell re-selection perhaps both by necrosis and apoptosis that also prevents destruction of the transplanted cells and regenerating organ.

The relative contribution of endogenous cells and donor cells to restoring endogenous beta cell activity was measured to determine whether the increase in beta cell activity was a result of endogenous regeneration from host precursor cells or, as demonstrated below, the conversion of donor lymphoid cells or donor islets into hosts islets. As described below, although rescue may play a role in the reversal of early diabetes and late diabetes, the administered donor cells were cells that could become host pancreatic beta cells. Restoration of near normal pancreatic islet histology was observed only in diabetic NOD mice that received both the $\beta_2M^{-/-}$ allograft and the CFA treatment. Pancreatic islets were not detected in any diabetic NOD mouse treated with CFA and syngeneic NOD islets. The persistence of normoglycemia in recipients of syngeneic NOD islets was apparently solely due to transplanted islets which always exhibited invasive insulinitis. Here, treatment with CFA, together with syngeneic NOD islets may have slowed disease recurrence, but persistent autoimmunity remained. We also assessed the relative contribution of restored endogenous pancreatic islets and transplanted islets to the maintenance of normoglycemia in NOD mice treated with CFA and allografts from $\beta_2M^{-/-}$ C57 donors. The relative contribution of the endogenous pancreatic islets was determined by removing the kidney containing the islet transplants after 120 days of normoglycemia from a group of five animals, as well as from a control group that had not received the allograft. All five mice which had received the allograft remained normoglycemic after nephrectomy until they were killed 3-60 days later. Histological analysis of kidneys that had not received the graft revealed a complete loss of identifiable islet structures. In contrast, the pancreata for all five allograft recipients contained well-formed islets, either without lymphoid infiltrates or with circumferentially distributed lymphocytes only. Normoglycemia after nephrectomy was thus maintained solely by endogenous pancreatic islet that we now know had reappeared in the host by both rescue as well as regeneration from endogenous or exogenous sources.

These results were affirmed by analysis of nephrectomies performed during the post-transplant period of normoglycemia on two mice which had received CFA plus syngeneic NOD islets. In this case, the treatment resulted in a rapid return to hyperglycemia, demonstrating that the control of blood sugar in this treatment group was mediated solely by the transplanted islet tissue. Diabetic NOD mice were also transplanted with islets from C57 mice in which the genes from both the $\beta_2M$ and TAP1 genes had been deleted. Together with TAP2, TAP1 mediates transport of endogenous peptides from the cytosol into the lumen of the endoplasmic reticulum for the assembly with MHC class I molecules. Our data using C57 mice in which the genes for both $\beta_2M$ and TAP1 had been deleted showed that these mice are more defective in the presentation of MHC class I self-antigens than those only having a mutation in the $\beta_2M$ gene. Transplantation of these double-knockout C57 islets lacking both β₂M and TAP1, combined with the injection of CFA results in return of hyperglycemia within 14 days in some of the animals. Two out of six NOD mice treated with the double knock out Class I cells had normoglycemia after 40 days of treatment. Physiological examination of the pancreas revealed a pattern typically seen in untreated diabetic NOD mice. The decrease in efficiency of this protocol supports the important role of correctly assembled and administered MHC class I and peptide complexes.

Based on these results, a transient interruption of peptide presentation of donor MHC molecules or a transient deficient MHC class I is important for the abrogation of autoimmunity. This transient ablation or decreased MHC class I or permanent presentation of donor MHC class I also appears to be a feature that allows these cells to transform into other cell types. In contrast, the sustained interruption of this process prevents the re-establishment of tolerance and the restoration of endogenous pancreatic islet integrity. The repeat administration of a normal MHC class I and self peptide or a short lived cell showed similar efficacy.

Given that the restoration of normoglycemia in diabetic NOD hosts treated with CFA and $\beta_2M^{-/-}$ C57 islets cannot depend on the continuing secretion of insulin by the islet graft, we now investigated whether C57 donor cell types, other than islets, might serve a therapeutic role. We initially performed these experiments expecting the C57 donor cell to provide MHC class I and self-peptide. As shown by the following results, donor lymphoid cells actually transform into insulin secreting beta cells in the host or fuse with damaged cells of the host or adjacent cells of the host. In these experiments, nine diabetic NOD mice were treated with a single bilateral injection of CFA, followed by a 40-day regimen of biweekly intravenous injections of C57 splenocytes. These lymphoid cells express both MHC class I and MHC class II proteins and survive only transiently in NOD hosts because of presumed graft rejection. However, contrary to the prior assumption that this would be only a transient treatment, these donor cells survive long-term without a need for immunosuppression in the host. Repeat injections of splenocytes ensured that the host was continuously exposed to antigen presentation complexes on the surface of these cells. Recipients were monitored for hyperglycemia every 3-4 days and insulin was administered daily unless normoglycemia returned. A control group of four diabetic NOD mice received daily insulin injections only. All four control group mice died on or before day 25 of the experimental period as a result of poor control of blood sugar and consequent ketoacidosis. In contrast, some of the mice injected with CFA and C57 splenocytes were alive after 40 days, and three of these animals had become normoglycemic and insulin independent.

While the pancreata of control mice exhibited pronounced lymphocytic infiltrates that obscured any remaining islet structures, the pancreata of the four NOD mice that were treated with CFA and C57 splenocytes and remained alive but hyperglycemic and insulin dependent revealed a marked decrease in the number of lymphoid infiltrates located circumferentially or adjacent to the infrequent islet structures. In the three NOD mice treated with C57 splenocytes and CFA that remained normoglycemic after the discontinuation of insulin injections, the pancreata exhibited abundant islets that were free of invasive insulinitis or islets associated only with circumferential lymphocytes. The treatment of CFA combined with re-exposure to C57 lymphocytes resulted in complete reversal of diabetes in approximately 30% of NOD recipients and partial restoration of beta cell function in approximately an additional 40% of hosts.

Subsequent experiments were conducted to determine whether the efficiency of the system could be improved by regulating glycemic control in the host. The reversal of diabetes in NOD mice by CFA and repeat exposure to C57 splenocytes indicated that the restoration of endogenous islet function is achievable without islet transplantation and despite the poor glycemic control attained by insulin injection. To determine whether the restoration of endogenous beta cell function could be achieved more consistently with better control of blood glucose, insulin injections were replaced with the intraperitoneal implantation of alginate encapsulated C57 mouse islets. Alginate encapsulation prevents direct contact between the donor tissue and the host T-cells and such grafts have been shown to provide near normoglycemic control for 40 days in approximately 78% of autoimmune NOD recipients. Almost all diabetic NOD mice that received alginate encapsulated C57 islets exhibited improved glucose regulation or normoglycemia. The alginate spheres were removed 40-50 days after implantation, and the blood glucose concentration was monitored. The seven mice treated only with alginate encapsulated islets, the six mice that received a single bilateral injections of CFA, and the three mice treated with biweekly injections of C57 splenocytes, all exhibited a rapid return to hyperglycemia and early death after removal of the implants. Pancreata of NOD mice that received only alginate encapsulated islets revealed no sign of intact islets or of lymphoid infiltrates. The pancreata of NOD hosts treated with CFA and alginate encapsulated islets exhibited marked invasive insulinitis and obscured islet structures. In contrast, seven of the nine diabetic NOD hosts that received CFA and C57 splenocytes remained normoglycemic for more than 40 days after removal of the alginate encapsulated islets. The pancreata of these animals contained large islets with circumferentially distributed lymphocytes. The islet mass after at least 80 days of disease reversal was estimated to be approximately 50% of the original value. The pancreata from control BALB/C mice contained approximately 25-35 islets, and the pancreata from successfully treated NOD mice contained approximately 12-20 islets, as determined by serial histological sectioning.

In addition, the maintenance of normoglycemia due to the treatment increased the percentage of diabetic mice permanently cured of hyperglycemia. We next identified features of this treatment regimen that contributed to the production of a positive outcome. As is noted above, CFA was used to induce the endogenous production of TNF-alpha, as well as other cytokines believed beneficial for removal of autoimmunity and to promote regeneration. The role of TNF-alpha in the treatment of diabetes was therefore investigated by the intravenous administration of rat IgG1 monoclonal antibodies to the cytokine TNF-alpha at a dose of approximately 1.5 mg/day for the first 10 days in diabetic NOD hosts treated with C57 splenocytes, CFA, and alginate encapsulated islets. All five NOD mice so treated exhibited a rapid return to hyperglycemia upon removal of the alginate encapsulated islets 50-70 days after transplantation consistent with the role of TNF-alpha in the beneficial effect of CFA. In a related experiment, an anti-TNF-alpha antibody (clone MP6-X73) was administered at a dose of 1.5 mg/day for 10 days after administration of CFA, C57 splenocytes, and alginate encapsulated islets into diabetic NOD mice (n=5). After removal of the alginate-encapsulated islets at day 40, hyperglycemia returned immediately in all five mice. In mice treated similarly except for the administration of the anti-TNF-alpha antibody, normoglycemia was maintained in seven out of nine NOD mice after removal of the alginate beads. The specificity of the effect induced by the anti-TNF-alpha monoclonal antibody was confirmed by the failure of the control rat IgG1 monoclonal antibody reactive with human T-cell receptor beta 1 chain to produce a therapeutic effect.

To demonstrate an increase in TNF-alpha levels due to administration of CFA, levels of TNF-alpha were measured in NOD mice after a single injection of CFA with or without donor lymphocytes. As Table 1, slightly elevated levels of TNF-alpha were transiently detectable in NOD mice for 2-5 days after a single injection of CFA with or without splenocytes. NOD mice at days 2-8 after a single dose of CFA also have decreased platelet levels from 30,000-60,000/mm$^3$. This data indirectly supports CFA's induction of TNF-α in NOD mice.

TABLE 1

Treatment of NOD mice with CFA results in elevated plasma TNF-alpha.

| Group | Donor Cells | CFA | TNF (g/mL) | | | | |
|---|---|---|---|---|---|---|---|
| | | | Day 0 | Day 2 | Day 5 | Day 21 | Day 40 |
| 1 | — | − | .40 | .35 | .41 | .42 | .38 |
| 2 | — | + | .51 | 20.1 | 18.1 | .49 | .30 |
| 3 | C57BL/6 | + | .35 | 21.7 | 17.5 | .50 | .57 |

TNF-concentrations were measured by solid phase ELISA using a sandwich technique with two different monoclonal antibodies to mTNF-alpha, one of which was conjugated to horse radish peroxidase (Sigma, St. Louis, MO). The limit of detection was 0.2 units/ml.

The data presented above show that the injection of CFA, the endogenous induction of TNF-alpha, or the administration of TNF-alpha directly results in the permanent elimination of TNF-alpha sensitive cells, the majority of which have previously seen islet cell antigens. In addition to the beneficial apoptotic death or effect on the lymphoid system, we also demonstrated that TNF-alpha binds directly to TNF Receptor 2 on the vascular endothelium, the complementary matrix for differentiation, and the islet precursor cells or islet beta cells themselves, thereby possibly also promoting regeneration in the pancreas. We further showed that the introduction of MHC class I peptide complex expression, either on the surface of normal islet cells or normal lymphocytes, results in a partial, but stable, reselection of T-cell population from the NOD hosts leading to an increase in the abundance of long-term memory cells. MHC class I and self-peptide reintroduction is important for the reselection of cells that probably have less stimulation with islet cell antigen, but the equivalent potential for autoreactivity (see, for example, U.S. patent application Ser. No. 09/521,064, filed Mar. 8, 2000, and 09/768,769, filed Jan. 23, 3001, and PCT publication WO00/53209, published Sep. 14, 2000, which are each incorporated by reference). Furthermore, additional studies presented herein show that these cells actually persist long-term in the host. We demonstrate that without any immunosuppression to the host, the semi-allogeneic MHC class I splenocyte origin cells or splenocyte residing cells, as well as semi-allogeneic cells from spleens differentiated into islets, persist long-term in the host without the need for immunosuppression. Furthermore, the reversal of any poorly controlled metabolic condition appears to promote the regenerative process and the reversal of established disease.

Example 2

Optimizing a Curative Therapy in the Diabetic NOD Mouse

In order to examine the differential effects of CFA, BCG, TNF-α, and splenocyte administration, late stage NOD mice (>15 weeks of age) were randomly assigned to one of four treatment groups, i.e., one injection of CFA, one injection of BCG (4 mg/kg), one injection of 10 ug TNF-α, or one injection of F1 splenocytes (1×10$^6$ cells, IV) obtained from normal donors. The treated NOD mice were serially sacrificed on day 2, day 7, and day 14 (Table 2). An examination of pancreatic histology evaluated the effects of the interventions on invasive insulitis (Table 3).

Table 2 shows that on day 2 both a single injection of CFA and a single injection of low dose TNF-α (10 g) had eliminated completely all subpopulations of cells with in vitro TNF-α sensitivity. At day 7 and day 14, this population of TNF-α sensitive cells was again evident. Simultaneous pancreatic histology of these cohorts confirmed a dramatic reduction in insulitis, as well as a lingering effect lasting beyond day 14 with respect to insulitis (Table 3).

TABLE 2

Percentage of remaining TNF -apoptotic-sensitive NOD splenocytes after various in vivo treatments

| | Day 0 (%) | | Day 2 (%) | | Day 7 (%) | | Day 14 (%) | |
|---|---|---|---|---|---|---|---|---|
| NOD mice | 0 ng | 20 ng | 0 ng | 20 ng | 0 ng | 20 ng | 0 ng | 20 ng |
| CFA | | | 26.6 | 24 | 29.2 | 34.2 | 26.6 | 35.1 |
| 10 g m-TNF | | | 27.9 | 28.2 | 28.9 | 36 | | |
| BCG | | | 7.4 | 22.3 | 15.3 | 26.7 | 37.8 | 28.9 |
| F1 splenocytes | | | 4.3 | 27.5 | 3.8 | 23.1 | 0.8 | 33.7 |
| untreated | 22.1 | 32.6 | 27.1 | 41.8 | 30.7 | 41.7 | 29.4 | 38.6 |

| | Day 0 | | Day 2 | | Day 7 | | Day 14 | |
|---|---|---|---|---|---|---|---|---|
| C57BL/6 | 0 ng | 20 ng | 0 ng | 20 ng | 0 ng | 20 ng | 0 ng | 20 ng |
| untreated | 14.1 | 14.7 | 12.3 | 12.8 | 18.8 | 16.2 | 17.5 | 17.2 |

NOD mice in this study were in a late pre-diabetic stage of disease at 18 weeks of age with at least one blood sugar greater than 200 mg/dL. Late apoptotic cells by flow cytometric studies of NOD mice treated with various immunomodulatory interventions were quantified on splenocytes after animal sacrifice in the days indicated after treatment initiation. For these flow cytometric studies, late apoptosis represents AnnexinV+ PI+ and AnnexinV+ PI− cells after 24 hours in vitro exposure to TNF- (20 ng/mL)

TABLE 3

Percentage of NOD islets with remaining invasive insulitis after various in vivo treatments

| | Day 0 (%) | Day 2 (%) | Day 7 (%) | Day 14 (%) |
|---|---|---|---|---|
| CFA | | | 4 | 22 |
| 10 mg m-TNF | | | 7 | 33 |
| BCG | | | 9 | 67 |
| F1 splenocytes | | | 26 | 31 |
| untreated | 100 | 0 | 100 | 100 |

The mice in Table 3 correspond to the same mice shown in Table 2

The responses to F1 splenocytes and BCG were markedly different than that seen with CFA and TNF-α, and somewhat different from each other. The therapeutic effect of F1 splenocytes was an elimination of the NOD lymphoid cells, which we believe represent pathogenic naïve cells, perhaps through a direct or indirect mechanism (Table 2). TNF-α sensitivity remained and the F1 splenocyte therapeutic impact lasted beyond day 14. The histology revealed a less dramatic impact on the numbers of NOD islets with remaining invasive insulitis. In addition, F1 splenocytes eliminated "cords" of invasive insulitis per islet instead of the more homogenous central elimination of insulitis characteristic of either TNF-α or CFA (not shown).

Unexpectedly, BCG, a known inducer of TNF-α had a greater impact on the elimination of tissue culture (naïve)

sensitive, pathogenic cells than it had on the elimination of pathogenic memory cells. The therapeutic effect of a single, low dose injection of BCG waned rapidly over the time course of 14 days (Table 2). The histologic analysis of the NOD pancreases confirmed partial elimination of insulitis (Table 3). Similar to the end result when MHC class I and self-peptide were reintroduced, the tissue culture-sensitive subpopulation of cells was eliminated.

These data are consistent with data in our earlier publication relating to the use of two limbs of interventions to "reverse" disease in NOD mice (i.e., TNF-α and F1 splenocytes). Our data show that these interventions can produce a distinct, measurable impact on specific lymphoid cell populations in the spleen. Each of the two limbs appears to target a different subpopulation of pathogenic cells with heightened apoptosis sensitivity. Importantly, the changes in T cell response to culture and TNF-α in vitro parallel the pancreatic histology of reduced invasive insulitis.

Although initially thought to be due to its reported induction of endogenous TNF-alpha release, the action of BCG in NOD mice appears to be predominately due to an indirect impact on naïve cell selection by the direct killing of monocytes/macrophages that have defective MHC class I presentation and, to a lesser extent, by reduction of the measurable burden of memory cells with TNF-alpha sensitivity. BCG is known to infect macrophages/monocytes and, if the BCG is avirulent, induces lysis of the macrophage/monocyte, thus reducing hampering continued production of tuberculin particles. Macrophage/monocyte lysis releases TNF locally, with infected cells usually containing abundant intracytoplasmic concentrations of this cytokine. In the NOD mouse, the avirulent strain of BCG causes lysis of certain subpopulations of monocytes/machrophages in an accelerated fashion. These cells appear to be developmentally "immature", with lower levels of MHC class I-self peptide expressed on the surface. This suggests that BCG sub-strains with the lowest virulence, derived from the in vitro selection of those that most rapidly lyse human or murine autoimmune monocytes, would be the best BCG strains to treat autoimmune disorders. Furthermore, these data suggest three strategies for identifying and eliminating naïve T cells: direct death receptor stimulation of the T cells through a susceptible receptor on the cells; introduction of corrected antigen presenting cells or complexes; with self peptide and or self peptide/MHC class I complexes, or the introduction of agents or adjuvants like BCG that cause the direct death of the monocytes/macrophages with the most severe defects in antigen presentation/processing, thereby eliminating the defective educator cells. In all three strategies, endogenous monocytes/macrophages with sufficient antigen presentation to bias the T cell repertoire back towards normal reselection predominate.

Example 3

Functional Impact of Donor Cell Radiation on Restoration of Normoglycemia in Severely Diabetic NOD Mice Severely hyperglycemic NOD mice were originally treated with CFA to induce TNF-alpha and simultaneously exposed to functional complexes of MHC class I molecules and allogeneic peptides presented on either viable splenocytes or on islets. Normoglycemia for a 40-day treatment period, a critical parameter of this approach, was induced either by the implantation of temporary alginate encapsulated islets or sub-renally placed syngeneic islet transplants. Both methods of glucose control can be surgically removed to test for restored endogenous pancreatic function. All original experiments were designed to treat established NOD female mice with severe hyperglycemia and utilized a 40-day time period of tight, artificial glucose control. Utilization of this temporary glucose control permitted sufficient endogenous pancreatic re-growth of the endogenous pancreas to sustain normoglycemia in up to 78% of formerly hyperglycemic NOD cohorts and to restore endogenous pancreatic insulin secretion.

To dissect the mechanism to NOD disease reversal, irradiated donor cells and live cells expressing MHC class I and self-peptide were studied. These experiments tested the role of long-term donor cell survival and the role of the donor cell function (e.g., antigen processing) in the permanent reversal of tolerance for self-antigens. NOD hosts used in these experiments were severely diabetic NOD mice typically greater than 20 weeks of age that exhibited blood glucose concentrations of greater than 400 mg/dl for at least seven days. All diabetic NOD hosts at this late stage of disease were dead within two weeks because of the severity of the disease. Alginate encapsulated islets were implanted into the peritoneal cavity for 40 days, and the hosts were randomized to receive either CFA alone or CFA in combination with intravenous biweekly injections of irradiated C57BL/6 splenocytes. At this point, the C57BL/6 splenocytes are only semi-allogeneic to the NOD host; the splenocytes are $H2K^bD^b$, and the NOD mouse is $H2K^dD^b$.

As we previously demonstrated, new cohorts of NOD mice immunized with live C57BL/6 splenocytes demonstrated restored normoglycemia. Seven of the nine newly treated NOD cohorts remained normoglycemic after the surgical removal of the alginate encapsulated C57 mouse islets. The reversal of autoimmunity was permanent, and the seven NOD hosts remained euglycemic for observation periods beyond 80 days at which time they were sacrificed. Eight additional NOD mice were treated with the same regimen, but with irradiated donor C57BL/6 splenocytes. In all eight cases, hyperglycemia returned within two to seven days after the removal of the alginate encapsulated islet that served as a glucose clamp during the 40-day treatment period. Pancreata of NOD mice that received live C57 splenocytes revealed abundant islets in seven of the nine mice. No signs of invasive islet lymphoid infiltrates, which are a sign of active autoimmunity, were present. When an islet was present, fewer than 10% of islet circumferential lymphoid cells encircled the pancreatic islet. Surprisingly, the pancreata of NOD mice that remained hyperglycemic and received irradiated donor splenocytes consistently revealed islets in the pancreas, but with decreased overall abundance as assessed by serial pancreatic sections. The islets in these pancreata were accompanied with sizable circumferential islet infiltrates but lacked lymphocytes within the islet structure itself, a histological pattern referred to as invasive insulinitis. For instance, pancreata from NOD mice treated with live splenocytes and having restored normoglycemia contained approximately 6-8 islets with each serial histological section, while pancreata from NOD mice treated with irradiated splenocytes and having persistent hyperglycemia contained 4-6 islets per serial histological section. Both irradiated and live splenocytes appeared to rid the diabetic host of invasive and destructive insulinitis. However, increased islet abundance and restored insulin secretion were only observed in NOD cohorts treated with live splenocytes.

In evaluating the significance of apparent histological elimination of destructive insulinitis without sufficient insulin secretion after the introduction of irradiated donor cells expressing MHC class I and self-peptide, additional diabetic NOD mice were treated. For these experiments, we used a treatment period of 40 days of donor MHC class I and self-peptides cell treatment, but extended the "glucose clamp period" of artificially restored normoglycemia from 40 to 120 days. The rationale for this experiment was to give the less efficient irradiated donor splenocyte treatment an opportunity for more complete host pancreatic rescue and a regeneration of the pancreatic islet. A cohort of 25 severely diabetic NOD mice was randomized for the same treatment protocol of live or irradiated intravenous MHC class I and self-peptide expressing cells for 40 days with a glucose clamp now implanted for 120 days. All treated NOD cohorts of both groups were followed for extended observation times for endogenous pancreatic function after clamp removal. Because a glucose clamp containing alginate encapsulated islets has a greater than 50% failure rate in an autoimmune host after 40 days of implantation, the glucose clamps used for these diabetic hosts were syngeneic islets transplanted under the kidney capsule. We removed this glucose clamp by nephrectomy 120 days after implantation.

Placement of the 120-day extended glucose clamp yielded a marked beneficial effect when combined with the formerly metabolically ineffective therapy of irradiated MHC class I and self-peptide expressing cells followed by an early evaluation at day 40. Functionally, 11 of the 12 NOD hosts which received live MHC class I and self-peptide expressing splenocytes continued to remain normoglycemic for observation times extending beyond 180 to 250 days after removal of the 120 day glucose clamp. Eleven out of the thirteen NOD hosts received irradiated MHC class I and peptide expressing cells and remained normoglycemic for a similar observation time. Both NOD treatment groups, receiving either live or irradiated MHC class I and self-peptide expressing cells, had physiologically equivalent pancreatic islet density as assayed using histological sections of the pancreas. The pancreatic islets in all cohorts of these two latter groups were examined after long-term follow-up of reversed disease for 180-250 days after restored normoglycemia. Formerly diabetic NOD cohorts with normoglycemia after irradiated donor lymphoid injections-possessed healthy and abundant pancreatic islets, but they were consistently accompanied by impressive circumferential lymphoid infiltrates. This histological feature was absent in treated NOD cohorts receiving live MHC class I and self-peptide donor cells. Therefore, although irradiated MHC class I and self-peptide expressing donor cells were effective at restoring long-term normoglycemia due to pancreatic insulin secretion, apparent non-progressive circumferential insulinitis was evident during long-term follow-up of the pancreas. Despite the histological differences, both experimental NOD treatment groups (all 25 cohorts) have pancreatic islets free of invasive insulinitis confirming the absence of active disease.

We also analyzed these cohorts to identify the actual composition of the insulin secreting beta cells in the pancreas, the blood, and the splenocytes at the time of autopsy to determine the contribution of the donor cells to long-term chimerism or conversion to pancreatic beta cells. These initial experiments comparing live to irradiated cells suggested that live cells had some advantages over irradiated cells. First, the live cells corrected diabetes at a much more rapid rate than irradiated cells. This result suggested that in the case of a long-term diabetic in which the regenerative capacity of the pancreas was possibly less evident, the introduction of live cells that have the ability to convert to beta cells might be an advantage. On the other hand, irradiated cells, which do not have the ability to regenerate into pancreatic islets, may have an advantage in a new onset diabetic because of greater safety. Also, islets in mice treated with live versus dead cells appeared histologically different—in that mice treated with live cells had significantly less circumferential insulinitis than mice treated with irradiated cells which, in many cases, had very impressive circumferential insulinitis. However, we have no reason to believe that circumferential insulinitis eventually progresses to active disease following treatment with irradiated cells.

There may be at least one more advantage to the regenerating tissue being of donor origin. In many of the treated NOD mice, syngeneic islet transplantation was performed under the kidney capsule. In all cases, even after complete disease reversal, syngeneic transplants exhibited pronounced peri-islet insulitis, in contrast to the regenerated semi-allogeneic islets in the pancreas, which were almost entirely free of peri-insulitis. These data suggest that syngeneic islets themselves have some yet unidentified defect that promotes an abnormal immune response, even in the presence of a fully re-educated lymphoid system.

Example 4

Reintroduction of MHC Class I Complexes to the Cell for Restored T-Cell Education The histological impact of the introduction of cells expressing matched and mismatched MHC class I peptide complexes on treatment outcome was also analyzed. As is described herein, treatment with a TNF-alpha inducing agent, e.g., CFA, and with cells that express MHC class I peptide complexes either on the parenchymal or lymphoid cells resulted in disease reversal in several severely diabetic NOD mice. In contrast, immunization with cells expressing MHC class II peptide complexes was not obligatory.

We have demonstrated the therapeutic effectiveness of MHC class I expressing islets or splenocytes from C57BL/6 strain carrying the H2K$^b$ and H2D$^b$ alleles (a matched and a mismatched MHC class I allele) and a self-peptide complex. We investigated whether the therapeutic effect was restricted to the matched or the mismatched MHC class I and peptide molecule or whether the effect had allelic specificity requirements for stable autoimmune disease reversal. The NOD mouse possesses two different MHC class I genes carrying the H2K$^d$ and H2D$^b$ allele, and the NOD mouse lymphoid cells fail to express a normal density of either self-peptide MHC class I structures. Severely diabetic NOD mice were treated with CFA in combination with a glucose clamp of intraperitoneally placed islets encapsulated in alginate or subrenally transplanted syngeneic islets. The diabetic NOD hosts received concurrent biweekly immunizations with parenchymal cell lines expressing fully NOD compatible MHC class I complexes on fibroblasts (e.g., fibroblast cells from H-2 MHC recombinant donor cell lines) or fully MHC incompatible MHC class I complexes on fibroblasts. All cohorts were sacrificed approximately 40-45 days after treatment initiation for the histological evaluation of the pancreas. Since the fibroblast cell lines represent tumor cell lines, the cells used in these experiments were irradiated prior to intravenous immunization or injection.

The histological results in the endogenous pancreatic islets differed in the NOD cohorts receiving fully MHC class I matched or mismatched peptide complexes. NOD cohorts randomized to receive MHC class I and self-peptide mismatched cells (H2K$^k$D$^k$), possess pancreatic islets with massive invasive lymphoid infiltrates in five of the five NOD mice. Not only was invasive insulitis present throughout the pancreas, but none of cohorts demonstrated a single islet structure without insulinitis or islets with exclusively circumferential lymphoid accumulation. The histological result obtained with diabetic NOD cohorts treated with intravenous injections of matched donor fibroblasts $H2K^d$ and $H2D^d$ class I and self-peptide structures were dramatically different. Treatment with MHC class I matched cells eliminated the invasive insulinitis in all 14 of the 14 NOD cohorts in the pancreatic islets; 2 of the 14 treated NOD cohorts had pancreatic islets totally devoid of any invasive or circumferential insulinitis, and 12 of the 14 treated NOD cohorts possessed pancreatic islets with mild-to-moderate circumferential infiltrates.

As presented above, the use of irradiated donor cells frequently results in the reappearance of pancreatic islets, but consistently these islets regardless of the cellular source were accompanied by circumferential lymphoid infiltrates adjacent to, but not invading, the islet structure. The ability of matched $H2K^d$ $D^b$ fibroblasts to histologically eliminate active islet-directed autoimmunity defined by invasive insulinitis confirmed the therapeutic effect of C57BL/6 expressing cells with a nonspecific effect of the allogeneic $H2K^b$ locus, but likely also benefited from the MHC class I reintroduction due to the matched $H2D^b$ locus through specific T-cell receptor or cell surface receptor (e.g., CD3) engagement of the host. Therefore, the target of the therapy is likely the host T-cells. Furthermore, non-irradiated F1 splenocytes from BALB/C and C57 crosses (i.e., CB6F1/J cells) similarly restored long-term normoglycemia in about 75-80% of the formerly diabetic NOD hosts receiving a single dose of CFA. Irradiated, mismatched MHC class I and self-peptide expressing cells were uniformly ineffective in reversing established diabetes. Therefore, this cellular therapy administered to established autoimmune NOD cohorts had (a) a demonstration that a therapeutic effect can be achieved with only a single MHC class I allelic match; (b) a demonstration that the cells can be administered in the presence or absence of allogeneic MHC class I and self-peptide structures; (c) a demonstration that the cells injected into diabetic NOD hosts can be live or irradiated donor cells; (d) a demonstration that the cells can be parenchymal or lymphoid in origin; and (e) a demonstration that the cellular effect can be independent of donor MHC class I donor cells expressing MHC class II and self-peptide complexes since fibroblasts, an MHC class II negative cell type, and lymphocytes showed equal efficacy.

We also performed a cytotoxic T-lymphocyte assay to define the separate therapeutic effects of MHC class I and self-peptide and the therapeutic effects of CFA/TNF-alpha for reversal of islet-directed auto-reactivity. As detailed above, an effective therapy to reverse established autoimmunity included the introduction of both MHC class I and self-peptide matched cells and administration of CFA or another TNF-alpha-inducing agent. Here, the introduced MHC class I and self-peptide complexes were proposed to reselect poorly trained naïve cells with the potential for autoreactivity. Indeed, peripheral tolerance homeostasis appears to be maintained by peripheral MHC class I and self-peptide complexes, and this prevents naïve cell abundance or unstimulated T-cell abundance—a feature seen in the pre-diabetic NOD mouse or in the untreated NOD mouse after the onset of hyperglycemia. In contrast, the data presented herein indicate that autoreactive memory T-cells or cells with exposure to antigen stimulated cells are selectively sensitive to CFA presumably due to the obligatory endogenous TNF-alpha induction and subsequent apoptosis due to defects in NFκB signaling.

To show that these observations could not simply be explained by changes in cell number, we looked at the overall abundance of CD45, CD62L, or CD95. The specific functional role of naïve CD45RB high density cells ($CD45RB^{high}$) in memory and the role of CD45RB low density ($CD45RB^{low}$) NOD T-cells in autoreactivity was tested in vitro in cytotoxic T-assays to islet targets. While we refer to naïve cells as $CD45RB^{high}$ and memory cells as $CD45RB^{low}$, these cells probably do not represent naïve versus memory cells, but rather represent cells in different stages of activation depending on exposure to antigen. For brevity, we refer to these cells as mostly stimulated or unstimulated cells, but sometimes we also refer to these cells as naïve or memory cells. The splenocyte donors, the source of the CTLs, were untreated NOD hosts, NOD hosts treated solely with CFA, and NOD hosts treated with both MHC class I and self-peptide and CFA with long-term disease reversal. Dispersed NOD islets from 8 week-old NOD female donors were used as responder cells. We used an insulin enzyme ELISA to detect T-cell lysis of syngeneic islets with insulin release from the target, as well as colorimetric quantitation of insulin by a spectrophotometer. The receptor T-cells were sorted into two pools prior to the assay: unstimulated T-cells defined as CD3 positive, CD45RBhigh, and stimulated T-cells defined as CD3 positive, $CD45RB^{low}$. Numerous effector to target cell ratios were tested. Based on these data, an optimized T-cell effector to islet target ratio resulted in co-incubation assays of 24-hours of culture at 37° C. Using the colorimetric readout as well as the direct insulin readout we determined the relative amounts of insulin released from live beta cells, and using the ELISA assay we determined the actual amount of released insulin in the culture supernatants. These results showed that diabetic NOD derived CD3 cells, either of the memory type or stimulated type or of the unstimulated type, equivalently lysed dispersed islet cells after 24 hours of co-culture.

Both the colorimetric assay and the actual measurements of released insulin confirmed the pathogenicity of the diabetic NOD cell populations as showing self-reactivity to syngeneic islet cells. The pathogenicity of stimulated $CD45RB^{low}$ T-cells can be selectively altered. Indeed, splenocytes from NOD cohorts treated with CFA alone 25 days prior to the assay showed the selective elimination of autoreactivity of only the stimulated cell population which has the ability to lyse syngeneic dispersed islet cells. CFA treated NOD cohorts maintained unstimulated $CD45RB^{high}$ T-cell populations with islet autoreactivity equivalent to that seen in untreated NOD splenocyte donors. Given that CFA therapy alone, with its resultant endogenous induction of TNF-alpha, was not successful in a diabetic NOD mouse in eliminating existing and late stage autoimmunity disease, the CTL results were consistent with the idea that two identifiable subpopulations of autoreactive cells may need to be manipulated in vivo for disease reversal. A marked contrast is seen in separated subpopulations of unstimulated $CD45RB^{high}$ and stimulated $CD45RB^{low}$ cells obtained from successfully treated NOD cohorts that received both syngeneic matched MHC Class I self-peptide expressing cells and CFA. These mice show complete and stable long-term elimination of both stimulated and unstimulated autoreactive T-cells with syngeneic islet directed autoreactivity.

Taken together, the results of the CTL assay indicate that in diabetic NOD hosts, unstimulated T-cells identifiable with CD45RBhigh and stimulated T-cells expressing $CD45RB^{low}$ have islet cytotoxicity or the potential for islet cytotoxicity. Autoreactive T-cell memory subpopulations were selectively eliminated with CFA alone, while both autoreactive stimulated and unstimulated subpopulations were eliminated with syngeneic MHC class I and self-peptide and CFA. Both aspects of the treatment may be required for the elimination of existing autoreactivity due to the existence of both stimulated and unstimulated cells with autoreactive potential. Accordingly, select treatments may be designed to target and eliminate the separate cell populations. Indeed this hypothesis was supported by our earlier adoptive transfer data showing that autoreactive NOD cell populations remained after TNF-alpha treatment of diabetic donor splenocytes, presumably because of the ability of these cells to change their phenotype and become TNF-alpha sensitive after islet exposure.

Example 5

T-Cell Re-Education Due to Exposure to MHC Class I and Presented Self-Peptide

Figure 2:
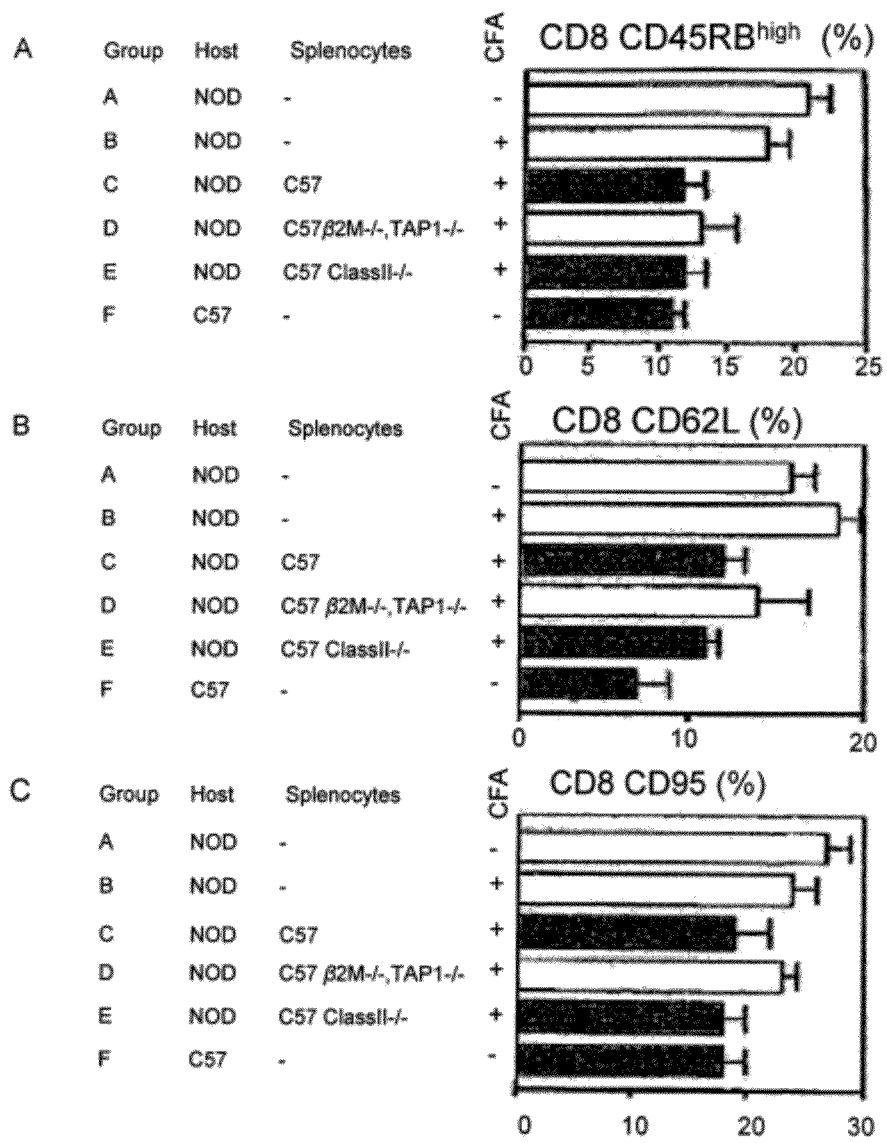
FIGS. 2A-2C are graphs demonstrating the percentage of CD8 $CD45RB^{high}$, CD8 CD62L, and CD8 CD95 cells in mice treated with or without CFA and with or without donor splenocytes.

To demonstrate that reversal of established NOD autoimmunity was linked to MHC class I education of T-cells, we monitored NOD mice before and after diverse therapies to measure a trend towards restored CD8 T-cell selection. As illustrated in FIGS. 2A-2C, untreated NOD mice or NOD mice only treated with CFA have high levels of CD62L, CD45RB$^{high}$, and CD95 positive CD8 cells. Treatment with CFA and C57BL/6 splenocytes or class II$^{-/-}$ splenocytes decreased the T-cell expression level of CD62L and partially normalized levels of CD45RB$^{high}$ and CD95 CD8 cells (FIGS. 2A-2C). Importantly, the apparent normalization of T-cell education/selection was not observed in NOD mice treated with CFA therapy alone (FIGS. 2A-2C). The establishment of normal numbers of memory T-cells was not observed when diabetic NOD were treated with CFA and C57BL/6 $\beta_2$ m$^{-/-}$ TAP1$^{-/-}$ splenocytes, a cell line with reduced peptide filled surface class I structures (FIGS. 2A-2C). Long-term memory requires the surface expression of self major histocompatibility complex molecules, and this positive selection by introduced class I expressing splenocytes restores T-cell selection towards normal.

Figure 3:
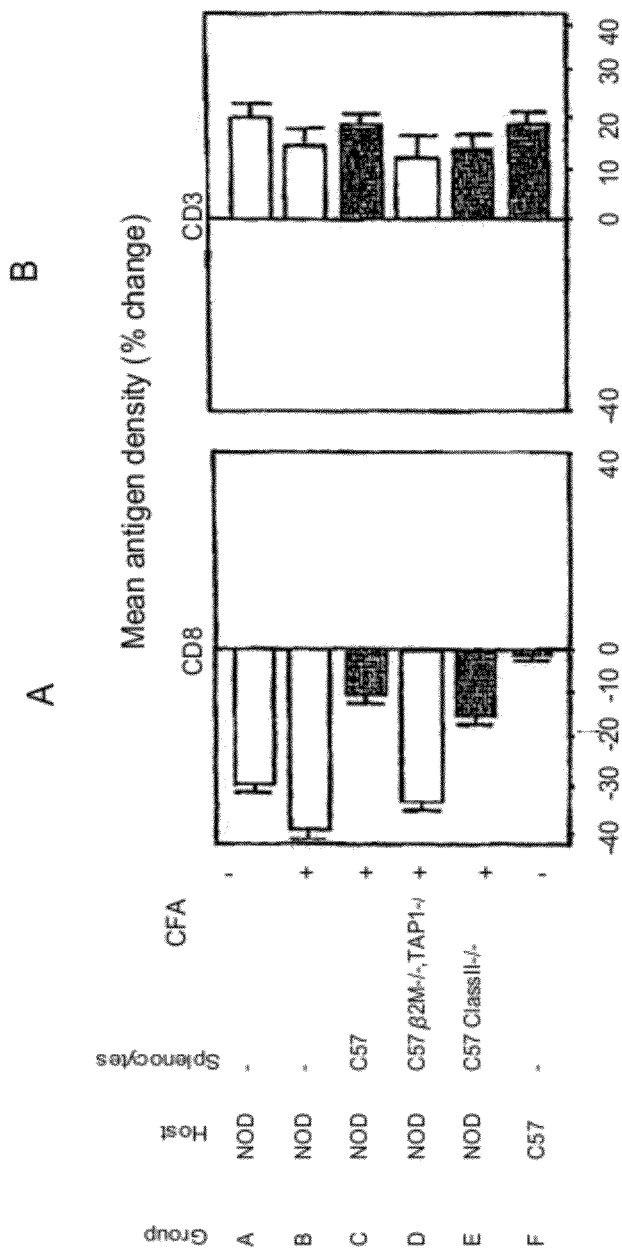
FIGS. 3A and 3B are graphs of the percent change in the mean antigen density in mice treated with or without CFA and with or without donor splenocytes.

Previously published data supports the concept that CD8 gene expression is maintained by proper peripheral MHC class I presentation. If class I education is interrupted, treatment of CD8 cells with 0.4% pronase followed by 48 hours of culture results in low surface re-expression of CD8 levels (Pestano, Science 284:1187-1191, 1999). Indeed, C57BL/6 splenocytes fully recovered CD8 levels after in vitro pronase treatment: no change in CD8 density was observed after pronase (FIGS. 3A and 3B). In contrast, NOD splenocytes after pronase treatment did not adequately re-express CD8 surface levels (FIGS. 3A and 3B). This result confirms previously published studies of interrupted MHC class I presentation in the NOD mouse. Splenocytes from NOD mice, whose diabetes was successfully treated in vivo with C57BL/6 or C57BL/6 class II$^{-/-}$ splenocytes and CFA, had improved CD8 re-synthesis after pronase treatment in vitro. In contrast, NOD mice treated only with CFA or class I deficient C57BL/6 splenocytes with CFA had persistent problems with CD8 re-synthesis similar to untreated NOD mice, confirming the persistence of interrupted T-cell selection by MHC class I structure. Simultaneously performed control experiments confirmed splenocytes from NOD mice of diverse treatment groups and splenocytes from C57BL/6 mice re-synthesize CD3 surface proteins at comparable rates (FIGS. 3A and 3B). Therefore, four established parameters of interrupted CD8 education (CD45RB$^{high}$ CD62L, cD95, and CD8 resynthesis) due to faulty MHC class I presentation, confirm that NOD mice with disease reversal have partial to complete correction of CD8 phenotypes of T-cell selection.

Example 6

Both Subrenally Transplanted Islets and Endogenous Pancreatic Islets Show Equivalent In Situ Islet Regeneration at Both Sites In the present studies, we demonstrate that an effective therapy can utilize TNF-alpha induction of CFA combined with irradiated or live MHC class I-matched cells. This combination cures diabetes in over 78% of treated NOD hosts. In addition, we demonstrate below that functional pancreatic recovery was slower in the pancreas of cohorts receiving irradiated cells expressing MHC class I self-peptide, although long-term and stable recovery occurs at equal frequency with follow-up in excess of 120 days. To assess the long-term resistance of transplanted islets compared to re-grown endogenous pancreas islets to disease, additional sets of diabetic NOD cohorts received either live or dead MHC class I and peptide expressing splenocytes combined with syngeneic islet transplants, which served as a glucose clamp. The ectopic islet transplants under the renal capsule allowed us to evaluate disease recurrence and ectopic islet regeneration compared to that seen in the pancreas. Fluorescence immunocytochemistry was used to compare the pancreatic islets to the subrenally placed islets. In these experiments, we utilized a combination of staining to insulin and BrdU to quantify the proliferating islet mass at the two sites and to determine a possible difference in resistance of transplanted islets and endogenous pancreatic islets to recurrent disease. We can also quantify possible proliferation of islet cells and/or their precursors at the two sites in two successful therapy versions. Since there is speculation that transplanted islets without their locally adjacent pancreatic precursor cells are end stage cells, these experiments tested the hypothesis that long-term islet survival might be an exclusive pancreatic trait. These long-term NOD cohorts were compared to severely diabetic NOD mice which had received subrenal syngeneic islet transplants 8 days prior to the experiment, but without the desirable CFA and MHC Class I and self-peptide therapy. Hematoxylin and eosin staining of both subrenal and pancreatic islets of a recently diabetic NOD mouse showed impressive and large lymphoid infiltrates, almost totally obliterating the newly transplanted NOD islets, and similarly invasive lymphoid obliteration of the pancreatic islets. Moreover, the corresponding inspection of both the renal and pancreatic sites for insulin positive cells revealed an almost totally negative result. The staining for proliferating cells assessed by BrdU at both sites also showed the lack of islets in the pancreas and a lack of any proliferation, which suggested that invasive and autoaggressive insulinitis have recurred or, alternatively, that the ongoing disease was not due to local lymphoid proliferation, but rather a migration of these autoaggressive cells to the islet site. In other words, the BrdU positive cells were not more highly positive in an active rejection response, suggesting the active cells migrated to the site.

As presented above, each pancreatic section showed that NOD hosts receiving irradiated MHC class I and self-peptide expressing cells have healthy pancreatic and subrenal islet cells that are surrounded with impressive circumferential lymphoid infiltrates. These lymphoid accumulations do not progress to an invasive islet pattern even with long-term follow-up, nor do they appear to enlarge in the long-term. The immunocytochemistry of the islet shows that successfully treated NOD mice have insulin positive cells subrenally and in the pancreas. Furthermore, within the islet mass of both the pancreas and subrenal site of long-term corrected NOD hosts, infrequent but proliferating insulin positive cells were observed as demonstrated by the yellow cells clearly indicating co-staining with insulin and BrdU. Since we used two different dyes to co-stain insulin and BrdU (i.e., red and green, respectively) a co-staining cell is yellow. In addition, based on the reported belief that fully differentiated islet beta cells do not proliferate, and instead are generated from progenitor cells, the insulin co-staining with BrdU (i.e., the yellow color seen by immunocytochemistry) likely represents a precursor cell in a proliferative phase. These results demonstrate that long-term endogenous and ectopic subrenal islet survival is possible after the underlying autoimmunity is reversed. Importantly, in view of our analysis of this very late stage after the successful reversal of disease, islet regeneration defined by BrdU and insulin co-staining can occur, although at a low frequency, in the pancreas and in subrenally transplanted syngeneic islets.

Using similar immunohistochemical techniques, we also examined the pancreata from long-term corrected cohorts to determine if the insulin secreting beta cells in the pancreas were solely due to regeneration of the pancreas from endogenous cells or if the regenerated pancreatic islets could also have originated from a donor source (e.g., from the injected splenocytes). In these experiments, we used formerly diabetic NOD mice cohorts that, after the onset of severe hyperglycemia, (i) were treated with CFA and fresh F1 splenocytes from male donors administered in biweekly injections for 40 days, (ii) were implanted with a subrenal syngeneic islet transplant for 120 days, and (iii) remained normoglycemic in the long-term when the transplant was removed. These mice were subsequently sacrificed at varying time intervals of stable normoglycemia, usually greater than 60 days. The pancreata of these animals were compared to the pancreata of animals that received the same treatment regimen, except that they received irradiated male donor splenocytes administered in biweekly injections for the 40-day treatment period. These pancreata were then stained with two-color immunofluorescence in which insulin was tagged with a red fluorochrome and a Y chromosomal marker was tagged with a green marker. All splenocyte donors were of male origin; therefore this fluorescence assay was used to determine if any of the insulin positive cells in the pancreas were of male Y chromosome origin. We furthermore performed insulin co-staining to prove that the Y chromosomes that can be seen in the islet were of islet origin, and were not of donor lymphoid origin (FIG. 1). Yellow cells indicated the co-staining of insulin and the Y chromosome marker in a single positive cell: yellow cells were only seen in cohorts that received live F1 splenocytes and not seen in the pancreatic islets of cohorts that received irradiated donor stem cells.

Furthermore, the double-positive (yellow) islet cells of donor origin with Y chromosome staining were only seen in the endocrine tissues of the pancreas, and not in the exocrine tissues, suggesting that the regeneration had occurred only in the target tissue that was injured. Moreover, in the animals that received irradiated cells, no green positive cells (i.e., Y chromosome containing cells) were seen either in the insulin secreting tissues of the pancreas or in the exocrine tissues of the pancreas. Furthermore, the cohorts that received irradiated cells also never expressed yellow cells in the exocrine or endocrine tissues of the pancreas, therefore confirming that Y chromosome positive cells were not present in animals that have received irradiated cells as part of their curative regimen.

Histological analysis of the islets that contained cells of donor origin revealed that, at times, whole islets were of donor origin and at other times the peripheral beta cells of the islets were mostly of donor origin. Overall, in a typical pancreas, up to 30% to 50% of the entire islet population of the pancreas appeared to be of donor origin suggesting that this was not an occasional phenomenon of differentiation of blood into islet origin, but was actually quite a dramatic finding. All these immunohistochemical data were derived from cohorts with long-term normoglycemia, as determined usually around 120 days after the original islet transplant or after the original splenocyte injection.

Experiments performed on NOD mice for the regeneration of pancreatic islets have revealed a number of transcription factors that are beneficial for the methods of the invention and a number of protein expression patterns that are signatures of organ/tissue regeneration. NOD mice have at the site of vigorous islet regeneration increased VEGF expression, increased Flk-1 expression, and locally high levels of proteasome function, including high levels of LMP-2 and INF-gamma. To accelerate the regeneration process, agents such as TNF-, TNFR agonists, or gamma interferon can be administered to the host prior to the initiation of regeneration. The administration of cytokines that induce TNF-expression, IL-1 expression, HAT, NF-B, AP-2, EGF-1, Sp1, AP-1, GATA, PECAM-1, activator protein-2, CT-rich Sp1 binding activity, PDGF-A, PDGF-B, monocyte chemoattractant protein-1, TF, Ets1, SCL/Tal-1, FGF, HATs P/CAF, PDGF, CBP/p300 and HIF-2-alpha (HRF, EPAS, HLF) can also be useful for the acceleration of islet regeneration. In certain cases, islet regeneration can be aided by the administration of VEGF, VEGF fragments, FGF, IGF-1, or by BV endothelium differentiation or tissue regrowth.

In other cases, one or more death receptors (e.g., the death receptors listed in FIG. 5) are inactivated on the donor cells or one or more intracellular signaling proteins that mediate cell death are inactivated in the donor cell to prevent death of the transplanted cells. For example, FLIP can be used to down regulate Fas/FasL expression. In other embodiments, extracellular inhibition or reduction in IL2 (e.g., inhibition due to chemicals or antibodies) is used to upregulate FLIP which then down regulates FAS. In other embodiments, the donor cells have a blockage of IL2R, such as the binding of a chemical (e.g., a non-lytic antibody fragment) to IL2R to inhibit binding of IL2 to IL2R and thus IL2-mediated upregulation of FAS. In other embodiments, one or more members of the intracellular pathway for FAS activation are inhibited in the donor cells prior to transfer. Examples include the inhibition of the translation of transcription factors such as cFOS, cJAN, PKC, Lck, Zap70, MAPK, Itk (IL-2 inducible T cell kinase) and JNK. In particular embodiments, the transcription or translation of transcription factors is transiently inhibited with antisense oligonucleotides or by RNA interference (RNAi).

Promotion of islet regeneration can be accomplished using one agent, or more than one agent, administered with or without pluripotent cells. The progress of islet regeneration can be monitored using sequential RT-PCR analysis to probe for the induction or suppression of transcription factors after agent administration.

Example 7

Donor Derived Cells are Also Present in the Blood

Because of our dramatic findings in the pancreas of donor origin F1 cells turning into pancreatic islets, we also serially examined both the blood and splenocytes from these cohorts to see if the blood and splenocytes were also of donor origin. Approximately eight cohorts of this long-term description were examined for the presence of $K^b$ positive lymphoid cells in the peripheral blood; splenocytes at the time of sacrifice were also examined. As is noted above, $K^b$ cells must be of B6 origin because the NOD mouse is of $K^d$ origin. We analyzed peripheral blood lymphocytes from these cohorts using flow cytometry analysis and found that in the peripheral blood 12.6%, 8.3%, 10%, 0.9%, 4.4%, and 5.8% of the lymphocytes were of donor origin. In contrast, a cohort that received irradiated cells, in which staining would only represent endogenous staining (i.e., background staining), had 2.9% of lymphocytes of donor cell origin. Thus, many of these cohorts had a percentage of donor origin lymphocytes in the peripheral blood that was significantly above background and had long term co-existence of blood cells of two different genetic origins and pancreas cells of two distinct genetic origins.

To better define this co-existence of donor derived and endogenous cells without immunosuppression, skin transplants were also performed on these long-term cohorts from the B6 donor. We had presumed that since there was blood chimerism and now pancreatic chimerism, the skin graft would survive long-term. To our surprise, skin graft survival from the B6 cohorts was not prolonged, or not visibly prolonged, in cohorts that retain stable blood and pancreatic islet chimerism, indicating that this sort of chimerism is distinct from the chimerism that results from total body irradiation followed by bone marrow reconstitution.

Nonetheless, the methods described herein provide a remarkable way to transplant cells without the need for immunosuppression. In view of the standard knowledge in the field of transplantation prior to the present invention, donor cells that not only are chimeric—being of donor male origin bearing disparate MHC genes and remarkably turning into pancreatic islets—but also are semi-allogeneic would be expected to be rejected because, while the host received CFA or TNF-alpha, the host did not receive immunosuppressive treatment. However, as is shown by our results, we were able to maintain long-term chimerism. In many ways the stable chimerism that could persist beyond 180 days after therapy termination mimics pregnancy where fetal origin F1 cells can survive long-term in mothers, long after the fetus has been removed.

Example 8

Organ Regeneration in GFP C57BL/6 Mice

As noted above, the data described herein using mice with established diabetes (e.g., NOD mice) demonstrate the ability to re-grow islet cells in the pancreas. The experimental results are excellent and demonstrate a robust and sustained ability to achieve engraftment. To try to duplicate these results, and to determine the parameters that allow this remarkable phenomenon to occur, we set up a test system to define the parameters that allow the NOD mouse to re-grow its islets from donor blood cells. The test model used cells from GFP BL/6 (B6) mice expressing green fluorescent protein (GFP) in all tissues as donor cells for introduction into B6 cohorts. Initially, we used GFP B6 splenocytes injected into normoglycemic hosts. We then examined these hosts at varying intervals for pancreatic, lung, and blood chimerism. After 90 days, no chimerism of the donor origin was visible. Based on these findings, we decided to test the possibility that the host pancreas needs to have an insult (e.g., the co-administration of streptozotocin to allow the GFP positive B6 donor lymphocyte cells to target the pancreas and also regenerate it). Therefore, GFP positive B6 cells from splenocytes and bone marrow (Hoechst 33342/ SP positive cells) obtained by flow cytometry and hepatocyte origin cells were administered at doses of $5 \times 10^5$ to $5 \times 10^7$ cells over a 40-day period, and the cohorts were then examined after 40 to 195 days either by eye bleeds or by sacrifice followed by examination of splenocytes.

In these experiments, although there was injury to the pancreas, there was little persistence of long-term chimerism in the host animals. Occasionally, a pancreas positive cell of GFP origin was observed, but the data were in large part negative suggesting that we had not properly duplicated the experiments that were so successful in the NOD mouse. One potential reason for the lack of success of this experiment or for the success of the experiments in NOD mice is that although we had induced injury in the pancreatic islets, these animals were severely hyperglycemic. Based on our previous data, severe hyperglycemia hampered regeneration.

To determine if severe hyperglycemia was interfering with the regeneration of the pancreas, we repeated the experiments using streptozotocin induced damage and a glucose clamp with subrenal islets and then used donor splenocytes or donor bone marrow from GFP positive B6 donors. In response to this treatment, the chimerism was still partial, not long-term, and did not represent the striking regeneration of the islet tissue.

We further optimized the treatment by administering streptozotocin to another set of B6 cohorts, inducing the glucose clamp with subrenally transplanted syngeneic islets, and co-administering TNF-alpha or CFA concurrent with the donor lymphoid cell injection. We used this protocol because we thought that we needed injury to islets to result in high TNF Receptor 2 expression on the islets or growth receptors to perhaps promote regeneration of the endogenous pancreatic islets. Furthermore, we thought that TNF Receptor 2 and progenitor cells from the blood might also promote endogenous GFP positive B6 islet regeneration and that CFA and TNF-alpha might be beneficial in another manner. We had previously obtained data indicating that CFA or TNF-alpha induces severe transient lymphopenia in the host, which is similar to data obtained in human clinical trials. Therefore, we injected the six hosts, not only with streptozotocin and an islet transplant, but also with CFA or TNF-alpha to induce the severe transient lymphopenia that might promote the peripheral blood chimerism. In addition, we injected splenocytes biweekly for 40 days. The results of these experiments looked much more promising, as 2-10% chimerism was detected in the peripheral blood 180 days after the completion of the injection and, furthermore, GFP positive cells of donor origin, although rare, were vividly expressed in the islets of the pancreas.

In short, in the syngeneic situation, splenocytes differentiated into insulin secreting beta cells, fused with beta cells, or provided factors for regeneration. We determined that, in the C57BL/6 host, CFA or TNF-alpha is desirably not administered concurrently with the donor cells. Therefore, these experiments using syngeneic transplants instead of allogeneic transplants and using an artificial model of islet injury suggest that target organ injury or active disease promotes the regenerative process after the elimination of the disease. A metabolically normal state is also important and may need to be maintained, as severe hyperglycemia appeared to interfere with the effectiveness of this treatment. Our results also indicate that TNF-alpha or CFA may facilitate the effectiveness of the treatment. These results likely represent a dual effect, not only of CFA's elimination of autoimmunity in the NOD mouse, but also of CFA's induction of severe lymphopenia, which, in turn may promote the chimerism of donor cells, as well as the subsequent chimerism and differentiation in the pancreas. Also, induction or administration of TNF-alpha has a beneficial effect on the target tissue or precursor cells promoting regeneration. Furthermore, it is known that the best induction of host regeneration, based on percentage success rate (92% vs. 72%), as well as the percent degree of chimerism/regeneration (approx. 87% vs. 54%), is still obtained from the administration of CFA, which is somewhat superior to the administration of TNF-alpha alone. It should be noted that once animals are successfully treated with either agent, the stability of disease reversal is equivalent. Although these results could be due to dose response phenomena, it is also observed that the simultaneous induction of INF-gamma with CFA is of direct benefit in conditioning the host vascular endothelium for recapitulating a regenerative program. Indeed, INF-gamma induces both high LMP2 and other proteasome subunits that promote vascular leakiness, a necessary step to presumed mesodermal cell migration and differentiation.

While the above experiments relate to the treatment of diabetes, these techniques obviously also are applicable to other diseases where host repair is desirable, providing new ways to transplant cells without the need for immunosuppression.

Example 9

Organ Regeneration in GFP C57BL/6 Mice

As noted in Example 7, additional experiments were performed using normal mice that are not of the NOD genotype to further understand and characterize the remarkable re-growth of islet cells observed in NOD mice.

FIG. 9 summarizes the many C57BL/6 mice that were treated with various therapies to achieve similar donor cell engraftment and possible re-growth of an adult organ/organelle such as the islets of Langerhans. All of these C57BL/6 hosts were made diabetic with streptozotocin using standard methods. In these experiments, glucose levels were not regulated using insulin injections or a temporary glucose clamp. If desired, insulin injections or a temporary glucose clamp may be used in any of the methods described below to optimized islet cell regeneration. It has been observed by us that in the NOD host, diabetes or late stage islet destruction is necessary for islet regrowth and thus to create a similar model of injury of the pancreatic islet, injury was induced with streptozotocin prior to the introduction of donor cells.

The Group 1 mouse was a female C57BL/6 mouse that received donor male splenocytes from a syngeneic C57BL/6 donor with GFP-actin fluorescence (C57BL/6-GFP). Thus, the donor cells can be distinguished from endogenous cells because the donor cells are of male origin (i.e., have XY chromosomes) and the endogenous cells are of female origin (i.e., have XX chromosomes). Additionally, the cells exhibit GFP fluorescence that is easily detectable using flow cytometric analysis. Removal of blood from this host and analysis of PBLs revealed that the peripheral blood only had 0.59% GFP cells. This demonstrates that the introduction of cells of splenocyte origin was not sufficient for establishing high levels of chimerism under the conditions tested. Also, the 0.59% value represents the degree of chimerism approximately four days after the final bi-weekly injection of donor splenocytes expressing GFP suggesting low levels of C57BL/6-GFP cells remained.

Group 2 C57BL/6 mice were treated as described for the Group 1 host. The spleen and the PBL of the treated mice were analyzed 150 days after treatment began. This treatment regimen involved bi-weekly injections of $10^7$ cells for the first 40 days after treatment. The PBLs of the group 2 hosts also had low levels of donor cells. The spleen had slightly higher but still low levels of C57BL/6-GFP cells. A subset analysis seemed to suggest the blood cells expressing GFP were not confined to any select lineage. Group 2 910, 911, and 903 NOD hosts were reanalyzed by regating the flow pictures of fluorescence and had similar trends of low levels of chimerism.

Group 2 mice 931, 939, 932, and 933 were also studied 87-98 days after transplantation of C57BL/6 splenocytes. The spleen of these animals had slightly higher degrees of chimerism with ranges of 4.7-13.3%. Although this result suggests a detectable level of chimerism, this chimerism was not long lasting because by an additional 100 days, the degree of chimerism was again low.

Group 3 and 4 C57BL/6 mice only differed from Group 2 and 3 mice in that Group 3 and 4 mice received donor bone marrow cells instead of splenocytes. Splenocytes were better able to engraft into the host than bone marrow donor cells. Group 5 C57BL/6 hosts received Hoechst333242 positive splenocytes; a cell type that is alleged by the scientific literature to poses stem cell traits. The transfer of these cells into the C57BL/6 hosts was only minimally successful and less successful than donor bone marrow or bone splenocytes.

Lastly, Group 7 and Group 9 C57BL/6 hosts received $10^7$ CNS precursor cells or hepatocytes (HC), and the hosts were killed approximately 100 days after cell transplantation. The spleen of hosts demonstrated more engraftment than the PBL, and donor CNS cells or donor hepatocytes may be better able to engraft into the host than bone marrow or Hoecchst33342 cells.

It should be noted for all these experiments in all groups we never saw with donor cell treatment reversal of the diabetes and we did not observe above background levels a clear regeneration of the islets in the pancreas. The pancreases possible regrowth, even temporary, would probably not have been detected with this experimental design because the killing of the mice was late in most cases. Future experiments were thus conducted to see if like the NOD a simultaneous tight control of blood sugars was necessary to promote islet regrowth during the experimental observation period and to perpetuate the chimerism in a target organ.

In the NOD model of disease reversal and islet re-growth, the data show that diabetic NOD mice that receive both CFA and donor F1 splenocytes exhibit islet regeneration (FIG. 10). A glucose clamp was used to regulate glucose levels and enhance islet regeneration. The data show that even very low dose TNF-alpha (e.g., doses of 2 ug/bi-weekly) can also promote the reversal of disease process. Further experiments revealed that the substitution of CFA with TNF-alpha required TNF dosing of 10-20 ug/bi-weekly. The NOD data also clearly shows that CFA alone or donor splenocytes alone were without long lasting effect at either disease elimination or islet regrowth at the time periods examined.

The second part of FIG. 10 now attempts to translate the NOD success story of organ regeneration into a C57BL/6 model of regeneration. This has helped to define the critical elements that promote regeneration. In all of the C57BL/6 mice in these groups, streptozotocin was used to induce tissue injury and to make the mice diabetic. As noted above, tissue injury promotes re-growth. Again, the groups that appear to have target organ regeneration are the groups that receive donor splenocytes plus TNF-alpha. In these experiments we try to map the pathway or receptor for regeneration as involving receptor I or II. At least for receptor II stimulation with the use of a C57BL/6 mouse with a mutation that inactivates TNF-α receptor I, we can see the persistence of the islet regeneration to a certain degree suggesting the islet regeneration may be promoted by this later pathway. The complete experiment could not be done in the reciprocal fashion because even very low dose TNF-alpha administered to a C57BL/6 RII−/− mouse resulted in immediate death; TNF-alpha toxicity may be through this receptor I, at least in control mice.

The last portion of FIG. 10 examines the effect of TNF in NOD mice in transiently promoting islet regrowth and the rapid elimination of invasive insulitis. With escalating doses of TNF, one can see not only the elimination of invasive insulitis but also islet regeneration. These NOD cohorts were typically examined about 40-50 days at the end of the TNF treatment course. Based on examinations of histological sections for TNFR11 expression, regenerating islets demonstrated up-regulation of this receptor while there was still some tissue injury. This up-regulation of TNFR11 may promote the beneficial effect of TNF in regeneration. For example, 20 ug dosing of TNF eliminated all the insulitis and resulted in regeneration of the islets to the most significant degree. Examination of NOD mice being treated with 20 ug TNF at earlier times prior to the end of the 40-day period would like reveal high TNFR11 expression that is eliminated by the end of the 40-day period because islet regeneration is complete. Also, treatment of NOD mice with human-TNF-, an agonist of only TNFR1 in the mouse, resulted in no islet regeneration, suggesting the beneficial effect of TNF- on organ regeneration was a function of the effect of TNF- as an agonist of TNFRII.

FIG. 11 summarizes the diverse experiments and outcomes depending upon the host representing an NOD mouse or a normal C57BL/6 host. The use of cells of splenocyte origin, blood origin or HC may offer an advantage because these organs contain diverse cell types and the re-introduction of mobilized, but not yet fully differentiated, endothelium, mesoderm, or ectoderm may promote, facilitate, or speed the necessary recapitulation of fetal tissue interactions that promote organ regeneration in an adult. The following data support the above hypothesis. During normal embryonic pancreatic islet development, the mesoderm interacts with the BV endothelium (endoderm). This interaction may promote VEGF expression, as well as the upregulation of Flk-1 receptors. To promote this process of organ specific regeneration in an adult, a number of steps are desirably followed. First, cells of the original developmental contact are desirably administered by IV injections or applied directly to the site of regeneration. For regenerating islet cells, blood vessel (BV) endothelium is desirably primed at the regeneration site by promoting the embryonic expression of VEFG, NF-B or associated events, such as increased proteasome activity or TNFR2 expression, and then contacted with administered mesodermal cells, even if of adult origin. For example, injected mesodermal cells may contact endogenous endoderm (e.g., endodermal cells within the pancreas or within other areas of the body), which promotes the recapitulation of the fetal patterning, i.e. the BV endothelium plus endoderm budding produces islets of liver cells. Indeed, in this particular clinical setting, the power of donor splenocyte origin cells in promoting regeneration may be more attributable to the mesodermal cells of the spleen than the more abundant blood cells. For re-growth of other tissues, administration of ectoderm, mesoderm, and/or endoderm may be desirable. Furthermore, for target organ re-growth, transient up-regulation of VEGF may be desirable. This up-regulation may be induced, e.g., by administering TNF-alpha, INF-gamma, or inhibiting cAMP. Also, administration of IL-2 may promote TNF-alpha that subsequently binds to BV endothelium, triggering VEGF up-regulation and NF B up-regulation, and thus target organ regeneration. Since TNFR2 is preferentially expressed on endothelial cells, this receptor is desirably manipulated for target organ regeneration. The ability of the NOD mouse to regenerate islets as demonstrated herein may be attributable, at least in part, to the islet specific up-regulation of the LMP2 subunits of the proteasome. Up-regulation of LMP2 is very influential in promoting VEGF/Flk-1/TNF-effects, with NF-B upregulation, as we now demonstrate by its diminished effect in LMP2−/− mice. We have demonstrated this regenerative process to be promoted in the NOD mouse and eliminated in the LMP2−/− mouse, thus verifying this pathway.

If desired any of the above regeneration methods may be enhanced by administering the donor cells more frequently and/or for a longer length of time.

Example 10

Assay Development of Human Diabetic Peripheral Blood Lymphocytes

As the relative efficiency of donor NOD splenocytes in transferring autoimmune disease is well known and NOD blood is very inefficient as a source of lymphoid cells in transferring disease to naïve cohorts, the magnitude of apoptosis induced by TNF-α in pathogenic NOD T cells from peripheral blood compared with the effect in T-cells from NOD splenocytes was quantified.

As Table 4 shows, accelerated cell death in NOD splenocytes, measured as both early and late apoptosis, resulted in 46% cell death. The effect on peripheral blood lymphocytes (PBLs) in the same NOD mouse was only 12% induced apoptosis. The distribution of pathogenic apoptotic sensitive cells appears to be lower in peripheral blood and higher in the spleen.

TABLE 4

TNF- sensitivity of PBLs vs. splenocytes in NOD mice*

| | Apoptosis of T Cells (%) | | | |
|---|---|---|---|---|
| TNF- | Spleen | | PBLs | |
| 0 ng/mL | 12.1 | 12.1 | 12.2 | 15.6 |
| 20 ng/mL | 11.8 | 22.6 | 11.5 | 17.7 |

*Apoptosis of T cells represents early and late apoptosis defined as Annexin V+ PI+ and Annexin V+ PI− cells on CD3+ T cells using flow cytometric studies The data in Table 5 show the degree of accelerated T cell death of human diabetic PBLs with culture and with TNF-α, as measured by flow cytometry. Apoptosis was quantified by flow cytometric monitoring of Annexin V, with or without propidium iodine staining, after a 12 hour in vitro culture or exposure to TNF-(20 ng/mL), TNF-with Act D (1 ng/mL), or other protein synthesis inhibitors known to amplify pro-apoptotic pathways of TNF-signaling by inhibiting the rapid synthesis of proteins that are anti-apoptotic. All assays were performed on freshly isolated PBLs and simultaneously prepared control samples. Both early and late apoptosis results were pooled for these data, but early and late apoptosis each was sufficient by itself in each category in Type I diabetics to yield highly statistically significant values of accelerated death through culture with TNF-. With flow cytometric data, profound changes in the relative mean death can be observed on any given day, so patient samples were always simultaneously studied and compared to paired t tests to control samples. The magnitude of the TNF-α induced apoptotic defect in humans is detectable with current flow cytometry techniques (8-10%) and is consistent with the results in PBLs in the NOD mouse. The 55 type 1 diabetic patients had higher death of naïve T cells (with culture) compared to 55 paired random (no history or family history of autoimmune disease) controls (p=0.0008). Actinomycin D is an accelerator of apoptosis when used with TNF-α. As shown in FIG. 5, TNF-α and TNF-α plus actinomycin D (p=0.0007) induced apoptosis were also significantly greater in the human diabetic T cells than in the control T cells (p=0.0154 and p=0.0007, respectively). The data suggest that the defect is widespread in Type 1 diabetes, with the majority of patients showing a detectable abnormality in T-cells (with a relatively larger fraction of T-cells with heightened TNF-α sensitivity).

It should also be mentioned that, similar to the NOD mouse, there appears to be two death-mediated events, a spontaneous death of cells with tissue culture preparation and a direct TNF-induced death of select T cell subpopulations. The spontaneous cell death maps to the monocyte/macrophage lineage of cells and the direct TNF-death maps in both species of T cells. The spontaneous death could be due to receptor activation of a death receptor due to shear stress or, alternatively, the elimination in the autoimmune patient of an abnormal serum factor that is abnormally pro-life or anti-apoptotic.

TABLE 5

TNF-induced apoptosis of peripheral blood lymphocytes of Type I and Type II diabetics compared to controls

| Comparison | Paired Samples | Conditions | Mean (patient) | Mean (control) | % Change | Paired t test |
|---|---|---|---|---|---|---|
| Type I diabetic vs. Control | 55 | Culture - 12 hrs | 28.8 | 26 | 10% | 0.0008 |
| Type I diabetic vs. Control | 55 | TNF | 29.6 | 27.2 | 8% | 0.0154 |
| Type I diabetic vs. Control | 55 | TNF + Actinomycin D | 42.8 | 39.2 | 10% | 0.0007 |
| Type II diabetic vs. Control | 18 | TNF | 26.5 | 26.9 | 1% | 0.9422 |
| Type II diabetic vs. Control |  | TNF + Actinomycin D | 38.8 | 38.1 | −2% | 0.5702 |

Example 11

Treatment, Stabilization, or Prevention of Disease Other than Diabetes

NOD mice also suffer from other autoimmune diseases in addition to diabetes, such as rheumatoid arthritis, lupus, multiple sclerosis, Sjögren's syndrome, multiple sclerosis, and autoimmune hemolytic anemia. In particular, the methods of the invention also improved symptoms associated with these other autoimmune disease and/or stopped progression of these diseases in NOD mice. The following treatments have been tested and shown to enhance regrowth of salvary glands, decrease hemopoetic abnormalities, stop the progression of multiple sclerosis and rheumatoid arthritis, and reduce levels of lupus autoantibodies: (i) biweekly injections (i.v.) of $10^7$ splenocytes expressing MHC class I and peptide for 40 days, (ii) biweekly injections (i.p.) of 2, 4, 10, or 20 μg TNFα or IL-1 for 40 days, (iii) a single injection of 5 μL in one footpad of 1 mg/mL solution of BCG, (iv) a single injection of CFA, (v) combined treatment with splenocytes and TNFα at the above doses, and (vi) combined treatment of splenocytes and CFA at the above doses.

Mice such as C57BL6 mice can also be used as animal models for the regeneration of other cells, tissues, or organs such as skin, liver, or brain cells.

Example 12

Factors Affecting the Efficiency of Organ Regeneration

Our data using GFP mice also demonstrated that, as we repeated these experiments with many different types of injected donor cells, differences exist not only in the degree of peripheral blood chimerism, but also in the persistence of peripheral blood chimerism induced by these different donor cells. As is noted above, the GFP positive donor cells that we obtained and injected included splenocytes, bone marrow derived cells, Hoechst 33342 positive cells obtained by cell-sorting, brain cells, CNS derived cells, and hepatocytes. Based on analysis of peripheral blood lymphocytes after sacrificing the animals for analysis of splenocytes, the duration of the chimerism in the absence of CFA treatment was dramatically different for different cell types. It turns out that, of the different cell types tested, splenocytes maintained the highest degree of chimerism for time periods greater than 100 days. In comparison, donor bone marrow cells were less effective, and the other cell types were least effective, suggesting that the donor cell origin even from the adult donors may also have an impact in the persistence of the chimerism.

In autoimmune hosts, the administration of any of a multitude of cytokines induce death or apoptosis of a subpopulation of pathologic lymphoid cells due to these cells having intrinsic errors in resistance to apoptosis or cell death. Accordingly, this treatment eliminates the pathologic cells from the host without harming the endogenous cells. In addition, introduced and endogenous cytokines promote the regeneration process of a damaged target organ. If a target organ is inflamed, is exposed to exogenous cytokines, or has increased proteasome activity, such as increased activity due to the overexpression of the LMP2, LMP7, or LMP10 subunits, a gamma responsive gene, or a TNF-alpha responsive gene, the target organ regenerates at an exponential rate. An increase in proteasome activity is likely to play a role in the action of VEGF, which together with the VEGF receptors Flk and Flt, functions in organ regeneration. Studies have shown that VEGF binds to developing organs and that this promotes end organ regeneration, possibly by binding to Flk or Flt receptors. We have shown that augmented proteasome activity results in augmented VEGF activity. In view of these results, in an autoimmune host, it is likely that, once disease is removed and in situ proliferation is desired, stem cells home to the target organ that had been under autoimmune attack and preferentially proliferate in this organ. The upregulation of proteasome activity and/or the upregulation of proteasome subunits with gamma interferon may promote this. In addition, gamma interferon may be used in a non-autoimmune host with tissue damage to promote targeting of this damaged tissue by stem cells. Furthermore, other chemicals and cytokines that also promote proteasome activity may be used in methods of organ regeneration. For example, in such methods, a promoter of proteasome activity may be administered concurrently with, prior to, or after administering stem cells or lymphocytes obtained from adult blood. After the addition of stem cells, local regeneration may be promoted by increasing Flk-1 receptors via CREB inhibition or by TNF-, HAT or NF B activation, or by administration of VEGF inhibitors. VEGF secretion may be promoted by proteasome augmentation, TNF-administration, cAMP inhibition, by the administration of IL-1 or IL-2, or by the application of sheer stress.

Example 13

Exemplary Agents for Use in the Methods of the Present Invention

Select autoimmune cell death can be achieved by administering agents that disrupt the pathways that normally protect autoimmune cells from cell death, including soluble forms of antigen receptors such as CD28 on autoreactive T-cells, CD40 on B-cells that are involved in protection of autoimmune cells, and CD95 or CD95L (i.e., FasL) on T-lymphocytes. Other such agents include p75N TNF and lymphotoxin Beta receptor (LtbetaR). Also, antibodies or fragments of antibodies reactive with these receptors are useful therapeutics. Such agents are described in the literature.

The present invention is not limited to a combined TNF-inducing therapy or direct compound administration that includes the combination of TNF-alpha and IL-1, but includes, e.g., any combination of TNF-alpha-including therapies, e.g., vaccination with BCG, viral infection, LPS, activation of cells that normally produce TNF-alpha (i.e., macrophages, B-cells, and T-cells), administration of the chemotactic peptide fMet-Leu-Phe, administration of bacterial and viral proteins that activate $NF_\kappa B$, administration of agents that induce signaling pathways involved in adaptive immune responses (i.e., antigen receptors on B- and T-cells, CD28 on T-cells, CD40 on B-cells), agents that stimulate specific autoreactive cell death receptors (i.e., TNF, Fas (CD95), CD40, p75NF, and lymphotoxin Beta-receptor (LtbetaR), and administration of substances that stimulate TNF-alpha converting enzyme (TACE) which cleaves the TNF-alpha precursor (i.e., to provide biological activity capable of stimulating enhanced production or enhanced cytokine life after secretion). Such agents are described in the literature.

In a preferred embodiment, monoclonal antibodies that serve as TNF-agonists can be administered. Such antibodies can be made using tumor necrosis factor-alpha receptor 1 (TNFR1) or tumor necrosis factor-alpha receptor 2 (TNFR2) as immunogens in mice using the hybridoma method first described by Kohler & Milstein, *Nature* 256:495 (1975). Such antibodies can also be made by recombinant DNA methods [Cabilly, et al., U.S. Pat. No. 4,816,567]. Such antibodies have been prepared and described by Brockhaus, et al., in *Proc. Nat. Acad. Sci. USA* 87:3127-31 (1990). Among the antibodies produced, those with agonist activity are identified by screening for TNF-like activity in assays measuring cytotoxicity, fibroblast growth, interleukin-6 secretion, or activation of the transcription factor NF-B. Alternatively, such antibodies can be screened in vitro using assays in which agonists are identified by their ability to kill activated T-cells obtained, for example, from a patient with lymphoma or newly diagnosed type-2 diabetes.

Methods for humanizing non-human antibodies are well known in the art. Generally, a humanized antibody has one or more amino acid residues introduced into it from a non-human source. These non-human amino acid residues are often referred to as "import" residues, which are typically taken from an "import" variable domain. In antibodies used in the methods of the invention, the import variable domain is from the TNFR1 and TNFR2 antibodies produced above.

Humanization can be performed, for example, following the method of Winter and co-workers [Jones et al., *Nature* 321: 522-525 (1986); Riechmann et al., *Nature* 332:323-327 (1988); and Verhoeyen et al., *Science* 239:1534-1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and, in some cases, some FR residues are substituted by residues from analogous sites in rodent antibodies.

Humanized antibodies desirably retain high affinity for the immunizing antigen, and thus are desirably prepared by known processes involving analysis of the parental and humanized sequences by three-dimensional modeling. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that desired antibody characteristics, such as increased affinity for the target antigen(s), are achieved. In general, the CDR residues are directly and most substantially involved in influencing antigen binding. For further details see U.S. Pat. No. 5,821,337.

Alternatively, it is possible to produce transgenic animals (e.g., mice) that are capable, upon immunization, of producing a full repertoire of human antibodies in the absence of endogenous immunoglobulin production. For example, the homozygous deletion of the antibody heavy chain joining region ($J_H$) gene in chimeric and germ-line mutant mice, resulting in complete inhibition of endogenous antibody production has been described. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551-255 (1993); Jakobovits et al., *Nature* 362: 255-258 (1993).

In the use of a TNF-receptor agonist antibody, patients are dosed such that enough is administered to elicit a TNF-like effect. The effective dose of such an antibody, or mixture of antibodies, is determined by starting at a low dose to ascertain tolerance, followed by dose escalation to produce the desired changes in circulating lymphocytes. For example, therapeutic dosing can be weekly or bi-weekly at levels of 0.025 mg/kg, 0.075 mg/kg, or 0.150 mg/kg (antibody/patient). Subsequent to antibody administration, disease activity is monitored in each patient category. For diabetes, monitoring may involve the tabulation of the amounts of insulin necessary to maintain normoglycemia or a positive trend in the reappearance of C-peptide levels. All patients during and after monoclonal antibody therapy are monitored for the presence of a human anti-murine antibody response to the anti-TNFR antibodies, as well as a human anti-human response.

In another preferred embodiment, the invention allows for the identification of drugs that induce cell death or selectively hamper the autoimmune cells by binding to cell surface receptors or interacting with intracellular proteins. For example, drugs that stimulate the IL-1 pathway or drugs that interact with converging pathways such as Fas, FasL, TACI, ATAR, RANK, DR5, DR4, DCR2, DCR1, DR3, TALL-4, or THANK. Also accelerated cell death of autoimmune cells maybe potentiated by adding protein synthesis or kinase inhibitors. For instance, accelerated TNF or FAS death is potentiated by brief exposure to a protein synthesis inhibitor (e.g., ActD) that blocks a rapidly made TNF-alpha mediated intercellular inhibitor(s). Similarly, kinase inhibitors also potentate TNF-alpha mediated events. The drugs of the present invention can be characterized in that they only kill autoimmune cells having a selective defect in a cell death pathway which can be characterized by two distinct phenotypes, (1) defects in lymphoid education and (2) susceptibility to apoptosis.

Other host treatment methods can be used as well to ablate autoimmune cells, for example, administration of CFA, interleukin-1 (IL-1), proteasome inhibitors, TNF superfamily agonists, NFκB inhibitors, anti-inflammatory drugs, tissue plasminogen activator (TPA), lipopolysaccharide, UV light, or an intracellular mediator of the TNF-alpha signaling pathway.

Example 14

Treatment

While the therapies described herein are likely to be effective in treating pre-diabetics, i.e., patients diagnosed as progressing to type I diabetes, but who are not yet hyperglycemic, we note that the methods of the inventions also may be used to treat a mammal, for example, a human with type I diabetes or any other autoimmune disease. The ability to treat patients who already have hyperglycemia and therefore have significant or total islet destruction is a significant advantage of the current therapy.

In general, before treating a patient, one may optionally obtain blood from the patient to determine that the patient has two disease phenotypes. The first disease phenotype is an increase in the number of circulating CD45RA positive cells in the blood (also defined as alterations in the number of cells positive for CD95, CD62L, or other markers of naïve or unstimulated cells). CD45, CD95, and CD62L are all cell surface antigens that can be monitored by flow cytometry and compared to age matched controls. We expect to see an abundance of these naïve or unstimulated cells in the peripheral blood of subjects with diabetes or any other autoimmune disease. The second phenotype is the presence of a subpopulation of lymphocytes with augmented sensitivity to cell death through apoptosis or necrosis. For example, subpopulations of cells may have augmented sensitivity to cell death caused by TNF-alpha, TCR receptor cross-linking agents, T-cell specific antibodies (e.g., αTCR or αCD3), or nonspecific stimulation with BCG. We may assay for the presence of such cells by isolating lymphocytes from these patients, treating them in vitro with TNF-alpha, and showing that the lymphocytes contain a subpopulation that undergoes apoptosis or necrosis when exposed to TNF-alpha, other cytokines, chemical reagents, or antibodies to select surface proteins. Desirably, control donor lymphocytes do not exhibit sensitivity to these agents. This phenotype is a result of lymphoid cells predominantly of pathogenic origin that have altered intercellular signaling pathways, alterations which result in a heightened death sensitivity. Elimination or conversion of all cells with this phenotype is desirable for the permanent reversal of autoimmunity. The penetrance of these defects is likely to be relatively high in diabetic or other autoimmune patients, with the first phenotype likely having a penetrance of over 95%, and the second phenotype likely having a penetrance of over 50% in type I diabetics.

Accordingly, before beginning to treat a subject with type I diabetes or any other autoimmune condition, we may determine from blood analysis alone whether the subject has either or both of these two phenotypes and, therefore, is amenable to therapy. To treat the first phenotype (i.e., an increase in the number of circulating CD45RA positive cells) tolerance to MHC class I and self-peptide may have to be re-established. We conclude from our results that the lack of functional MHC class I and self-peptide complexes causes the overabundance of naïve T-cells in the periphery or at least results in one of the phenotypes that causes this. So for treating this phenotype, we can administer blood or bone marrow that is a semi-allogeneic or fully-allogeneic match to the MHC class I and self-peptide complex. Furthermore, the blood or bone marrow derived cells, or even fibroblasts that have been immortalized, desirably may have normal MHC class I and self-peptide complex presentation; in other words, they should not come from diseased patients. Those phenotypes are easily monitored prior to treatment to determine the suitability of the donor cells in this therapy. For example, conformationally specific MHC class I and self-peptide antibodies may be used to show that the complexes are properly filled. In addition, we know that, in this aspect of the treatment, an increased number of matches to the HLA class I alleles of the host results in an increase in the duration of the reversal of the disease. Desirably, at least two, and desirably all four HLA class I alleles (e.g., the HLA A and HLA B alleles) from the donor cells are matched. Accordingly, these donor cells may be perfectly matched or they may be semi-allogeneic (i.e., with only partial matches on individual cells).

Treatment may involve intravenous biweekly infusions of $1 \times 10^7$ cells of any given donor of any given class I haplotype. It is desirable for the administered cells to be freshly isolated and not processed with preservatives or frozen. Cells that may be used in the methods of the invention may be obtained, for example, from a bloodbank. In addition, semi-allogeneic cells may be obtained from a close relative of the patient, such as a parent or a sibling. Furthermore, it would be advantageous to have the red blood cells eliminated from the preparations to decrease the volume of blood and lymphocytes administered. We also determined that semi-allogeneic or fully-allogeneic irradiated cells may be used in this therapy, but the use of irradiated cells results in a longer time course for correction.

As an alternative to administering MHC class I and peptide, another agent that inactivates or kills naïve T-cells can be administered. Exemplary agents include antibodies that bind and inactivate the T-cell receptor on naïve T-cells or by binding and triggering the selective death of only pathologic cells. In some embodiments, the antibodies inhibit the activity of or naïve T-cells by at least 2, 5, 10, or 15-fold more than they inhibit the activity of memory T-cells.

Simultaneously with the administration of donor cells, it is also desirable to induce endogenous TNF-alpha production either through stimulation with *Bacillus* Clamette-Guerin (BCG) or other immune adjuvants such as CFA, or by the direct administration of TNF-alpha. For example, one may administer BCG at least biweekly or, desirably, three times a week. Again, one skilled in the art can determine individually the dosing of the cells and TNF-alpha or BCG by analyzing a blood sample twice a week for evidence of the elimination of the phenotype of the pathogenic cell. For instance, to determine the correct dose of donor MHC class I expressing cells, we may look for the elimination of the abundant naïve cells in the peripheral blood and to determine the correct dose of TNF-alpha or BCG, we may look for the elimination of TNF-alpha in vitro sensitivity.

With regard to the second aspect of the therapy, TNF-alpha, BCG, or another nonspecific form of immune stimulation may promote the induction of endogenous TNF-alpha. For example, TNF-alpha may be administered intramuscularly, intravesicularly, or intravenously. Moreover, recombinant human TNF-alpha or new drugs such as a TNF receptor 2 agonist may be used. Such compounds have two effects, one is the elimination of apoptosis or death sensitive cells in the periphery which can be monitored, and the other is the promotion of endogenous beta cell regeneration, as well as possibly differentiation from the new donor blood. Exemplary doses of TNF-alpha that may be administered to a patient are approximately 40 $\mu g/m^2$ or 200 $\mu g/m^2$. Other exemplary doses include doses between $2 \times 10^6$ and $5 \times 10^6$ mg daily for two doses in one week. Patients with an autoimmune disease may tolerate higher doses of TNF-alpha and/or may require lower doses for treatment. As an alternative to TNF-alpha, tolerance can be gained by cross-linking the TCR or by non-specific vaccination through the same pathway (e.g., BCG vaccination). As an alternative to administering an inducer of lymphopenia (e.g., TNF-alpha) directly to a patient, the inducer of lymphopenia can be administered to blood obtained from the patient (e.g., blood obtained during electrophoresis), and the treated blood can be re-administered to the patient. For induces of lymphopenia with a short half-life (e.g., TNF-alpha) little, if any, functional compound remains in the blood that is re-introduced into the patient. Thus, this method should decrease the incidence or severity of any potential adverse, side-effects of the compound.

Any combination therapy described herein, e.g. a therapy which uses MHC class I expressing cells and TNF-alpha induction, may be administered until the disease is successfully treated. For example, this therapy may be continued for approximately 40 days; however, this time-period may readily be adjusted based on the observed phenotypes. Additionally, the dose of TNF-alpha can be adjusted based on the percentage of cells in blood samples from the patient that have increased sensitivity to TNF-alpha, indicating the amount of remaining autoimmune cells. In addition, in treating type I diabetes, it may be desirable that the patient maintains as close to normoglycemia as possible. The murine data have demonstrated that marked fluctuation in blood sugars hamper the normal regenerative potential of the pancreas. Therefore, these patients may be placed on an insulin pump for not only the exemplary 40 days of disease reversing therapy, but also for a 120 day period to optimize the regenerative process. The pancreas of long-term diabetics (i.e., ones having diabetes for more than 15 years) may have the regenerative potential of the pancreas diminished to such a degree that the precursor cells are no longer present. In these patients, the therapy may be identical except for the length of the treatment. For instance, the donor blood or bone marrow cells have to be alive for these cells to convert to the correct tissue type, such as into beta cells of the pancreas.

As is mentioned above, some embodiments of the invention employ mesodermal cells, which can be isolated from a normal donor (e.g., from the bone marrow, the spleen, or the peripheral blood). Typically, this cell expresses, to a detectable degree, $CD90^+$, $CD44^+$, or $CD29^+$, but does not express appreciable amounts of CD45 or CD34. This normal donor cell is administered to a person, preferably intravenously or intraperitoneally, to allow for rapid transport to the site of inflammation, injury, or disease. Desirably, this cell is administered to a person with active autoimmunity. Alternatively, the cell may be administered to a person without autoimmunity or to a person with quiescent autoimmunity. The absence of active autoimmunity in a person (host) may require pretreatment of the host to initiate an inflammatory response or injury at the regenerative site. In addition, pretreatment of the donor cell may also be required. The host may be treated with TNF-, IFN-, IL-2, VEGF, FGF, or IGF-1 to prepare the blood vessel endothelium for optimal interactions with the mobilized mesodermal cell. Additionally, the pathway of VEGF-stimulated expression on endothelial cells can be enhanced with a selective inhibitor of PI-3'-kinase. Alternatively, the host can be pretreated with platelet-derived growth factor derived from mural cells (e.g., from the neural crest or epicardium) for optimal interactions with the mobilized mesodermal cell. Additionally, the mesodermal cell can be pretreated to optimize adherence to the endothelium. This type of therapy is envisioned to be beneficial for the regeneration of diverse organs or organelles, including brain, skin, islets of Langerhans, heart, lung, liver, muscle, intestine, pancreas, bone, cartilage, and fat.

It may also be possible to optimize the fresh mesenchymal cell prior to injection into the host. This can be accomplished with TNF-exposure, IL-1 exposure, or other chemical/drug treatments to increase neogenesis.

For patients that have organ or tissue damage, but no underlying autoimmunity, it may be beneficial to avoid prolonged administration of an immune adjuvant, e.g., TNF-alpha, as such agents may result in the depletion of stem cells. Instead, desirably, one may induce transient lymphopenia with TNF-alpha or any other nonspecific reagent, remove this reagent, and add cells (e.g., stem cells) to regenerate the organ or tissue. In addition, the added stem or precursor cells may be altered to have reduced TNF-alpha sensitivity or may have increased proteasome activity or decreased death sensitivity through TNF or Fas. Furthermore, the host may be preconditioned with an agent that increases LMP2, LMP7, or proteasome activity (e.g., gamma interferon) prior to, concurrent with, or after the administration of stem cells. Compounds that increase Flt, Flk, VEGF expression or activity, hypoxia, GATA-2, hypoglycemia, IL-1, or inhibition of cAMP can also be used. Moreover, since administration of TNF-alpha results in cell death due to the upregulation of Fas or FasL, it may be beneficial to precondition a host with an inhibitor of Fas/FasL expression or function during TNF-alpha or other immune adjuvant therapy in both patients with and without underlying autoimmunity.

In contrast, administration of TNF-alpha during treatment of autoimmune conditions typically increases the number of stem cells and thus does not require steps to inhibit destruction of stem cells or to replace stem cells. TNF-alpha does not deplete stem cells is in NOD mice because many of the stem cells in these mice have intrinsic defects in Fas and FasL expression. In contrast to normal cells, which may die due to Fas/FasL upregulation that is induced by TNF-alpha, NOD stem cells survive. In a variety of human autoimmune diseases, the Fas/FasL downregulation enables these human cells to survive, or even expand, in the presence of TNF-alpha.

In a host with autoimmune disease, the signaling pathways are deranged and the administration of cytokines may have multiple effects. First, administered cytokines induce apoptosis of a subpopulation of pathologic lymphoid cells due to intrinsic errors in apoptosis resistance, thus identifying these cells as pathogenic. Furthermore, the introduced and endogenous cytokines also promote the regeneration process presumably on the target organ. Furthermore, if the target organ has inflammation and is exposed to the administered cytokines or processes endogenous errors in the overexpression of proteasome function (e.g., LMP2/7 subunit expression, a gamma responsive gene, or a TNF responsive gene), the organ regeneration will be promoted. While not meant to limit the invention to a particular theory, a possible mechanism of in situ regeneration is that activation of the proteasome is critical for the action of VEGF, and VEGF action is critical for Flk activity. Endothelial cells may promote this process and, with activation of the proteasome, VEGF action is accelerated thus allowing augmented Flk action. Exogenously added stem cells may exponentially promote this process, e.g., by independent proliferation or fusion with the cells or by differentiation to lineage-specific cell types. Therefore, to promote in situ organ regeneration, proteasome inhibitors are desirably avoided. A spontaneous autoimmune host in which target organ hyperexperession of LMP2 and/or LMP7 is frequent may also have accelerated organ regeneration. Organ regeneration can also be accelerated by promoting LMP2/7 hyperexpression with, e.g., gamma interferon, TNF, or a compound that activates the promoters of these genes, e.g., Stat1, agonists of the ICS-2/GAS elements in the LMP2 promoter, interferon regulatory factor 1(IRF1), TNF-alpha, or NFkB promoters.

Conversely, the administration of proteasome inhibitors may serve as a treatment for proliferative diseases. That is, a proteasome inhibitor can be administered that affects an autoimmune response for proliferative cells, such as, for example, cancer cells, while generating a relatively diminished autoimmune response for normal cells. Most desirably, the anti-proliferative proteasome inhibitor generates no autoimmunity to normal cells upon administration. In an additional example, anti-autoimmune therapy can be administered concurrent or subsequent to the administration of proteasome inhibitors. Other diseases that can be treated by proteasome inhibitors include acute inflammatory processes, such as, for example, sepsis or atherosclerosis.

Vascular endothelial growth factor (VEGF) is a potent angiogenic protein that enhances vascular permeability and promotes endothelial cell proliferation. VEGF stimulate two types of tyrosine kinase receptors, namely, the fms-like tyrosine kinase-1 (Flt-1) and the fetal liver kinase-1/kinase domain region (Flk-1/KDR). FGF (fibroblast growth factor), TNF, and highly confluent cell culture induce Flk-1/FDR expression in cells, whereas transforming growth factor 1 (TGF-1) reduces it. Thus, to promote regeneration, FGF and TNF are used, and TGF is desirably avoided. For regeneration in a normal host, the donor cells are desirably not exposed to TNF-like substances too early because these substances may accelerated death. In contrast, the host tissue may be exposed to TNF like substances or inducers of NF B or VEGF to increase Flk-1-like expression or signaling to promote the regeneration process and/or interactions that promote in situ regeneration. Therefore, normal donor cells may be pretreated prior to transfer to prevent death when exposed to endogenous TNF like substances. Alternatively, the host may be reconditioned with TNF-like substances (e.g., TNF, VEGF, FGF, or and NF B stimulator) prior to cell transfer to create an environment for optimal proliferation. As noted above, VEGF action is dependent upon a proteasome expressing LMP2, and thus agents that induce proteasome function are beneficial for regeneration. One such agent is INF (interferon), which upregulates the obligatory inducible proteasome subunits (e.g., LMP2) for optimal VEGF action.

Other Embodiments

From the foregoing description, it will be apparent that variations and modifications may be made to the invention described herein to adapt it to various usages and conditions. Such embodiments are also within the scope of the following claims.

All publications mentioned in this specification are herein incorporated by reference to the same extent as if each independent publication, patent, or patent application was specifically and individually indicated to be incorporated by reference.

What is claimed is:

1. A method for treating or stabilizing an autoimmune disorder selected from the group consisting of type I diabetes, celiac sprue-dermatitis, Crohn's disease, Graves' disease, hypothyroidism, lupus, multiple sclerosis, psoriasis, rheumatoid arthritis, sarcoidosis, Sjogren's syndrome, and ulcerative colitis in a mammal comprising administering to said mammal a composition comprising a tumor necrosis factor (TNF)-alpha receptor agonist that specifically binds or activates TNF-alpha receptor II but not TNF-alpha receptor I.

2. The method of claim 1, wherein said mammal is a human.

3. The method of claim 1, wherein said TNF-alpha receptor agonist treats or stabilizes said autoimmune disorder by selectively killing blood cells with increased sensitivity to cell death, and wherein killing of said blood cells treats or stabilizes said disorder.

4. The method of claim 1, wherein said TNF-alpha receptor agonist treats or stabilizes said autoimmune disorder by promoting cellular regeneration, wherein said regeneration treats or stabilizes said disorder.

5. The method of claim 2, wherein said disorder is type I diabetes.

6. The method of claim 2, wherein said disorder is celiac sprue-dermatitis.

7. The method of claim 2, wherein said disorder is Crohn's disease.

8. The method of claim 2, wherein said disorder is Graves' disease.

9. The method of claim 2, wherein said disorder is hypothyroidism.

10. The method of claim 2, wherein said disorder is lupus.

11. The method of claim 2, wherein said disorder is multiple sclerosis.

12. The method of claim 2, wherein said disorder is psoriasis.

13. The method of claim 2, wherein said disorder is rheumatoid arthritis.

14. The method of claim 2, wherein said disorder is sarcoidosis.

15. The method of claim 2, wherein said disorder is Sjogren's syndrome.

16. The method of claim 2, wherein said disorder is ulcerative colitis.

17. The method of claim 3, wherein said blood cells are T-cells, B-cells, or macrophages.

18. The method of claim 1, wherein said mammal already has symptoms of said disorder.

19. The method of claim 1, wherein said TNF-alpha receptor agonist is formulated for intramuscular, intravenous, intraperitoneal, intravesicular, intraarticular, intralesional, or subcutaneous administration.

20. The method of claim 1, wherein said TNF-alpha receptor agonist is administered in a single dose.

21. The method of claim 1, wherein said TNF-alpha receptor agonist is administered in multiple doses.

22. The method of claim 4, wherein said cellular regeneration comprises regeneration of an organ or tissue that is injured, damaged, or deficient in said mammal, wherein said organ or tissue is, or is part of, bladder, brain, nervous system tissue, blood vessels, skin, eye structures, gut, bone, muscle, ligament, cartilage, esophagus, heart, pancreas, intestines, gallbladder, bile duct, kidney, liver, lung, fallopian tubes, ovaries, prostate, spinal cord, spleen, stomach, testes, thymus, thyroid, trachea, ureter, urethra, uterus, or fat.

\* \* \* \* \*